United States Patent
Choi et al.

(10) Patent No.: US 11,217,329 B1
(45) Date of Patent: Jan. 4, 2022

(54) METHODS AND SYSTEMS FOR DETERMINING BIOLOGICAL SAMPLE INTEGRITY

(71) Applicant: Veracyte, Inc., South San Francisco, CA (US)

(72) Inventors: Yoonha Choi, South San Francisco, CA (US); Joshua Babiarz, South San Francisco, CA (US); Giulia C. Kennedy, San Francisco, CA (US); Jing Huang, South San Francisco, CA (US)

(73) Assignee: Veracyte, Inc., South San Francisco, CA (US)

( * ) Notice: Subject to any disclaimer, the term of this patent is extended or adjusted under 35 U.S.C. 154(b) by 671 days.

(21) Appl. No.: 16/017,899

(22) Filed: Jun. 25, 2018

Related U.S. Application Data

(60) Provisional application No. 62/524,393, filed on Jun. 23, 2017.

(51) Int. Cl.
*C12Q 1/6869* (2018.01)
*G16B 25/00* (2019.01)
*C12Q 1/6886* (2018.01)
*G16B 40/00* (2019.01)

(52) U.S. Cl.
CPC .......... *G16B 25/00* (2019.02); *C12Q 1/6869* (2013.01); *C12Q 1/6886* (2013.01); *G16B 40/00* (2019.02); *C12Q 2600/156* (2013.01)

(58) Field of Classification Search
CPC ............... C12Q 1/6869; C12Q 1/6886; C12Q 2600/156
See application file for complete search history.

(56) References Cited

U.S. PATENT DOCUMENTS

| | | |
|---|---|---|
| 3,645,691 A | 2/1972 | Guenter et al. |
| 3,687,808 A | 8/1972 | Thomas, Jr. et al. |
| 5,130,238 A | 7/1992 | Malek et al. |
| 5,143,854 A | 9/1992 | Pirrung et al. |
| 5,288,514 A | 2/1994 | Ellman |
| 5,384,261 A | 1/1995 | Winkler et al. |
| 5,399,491 A | 3/1995 | Kacian et al. |
| 5,455,166 A | 10/1995 | Walker |
| 5,494,810 A | 2/1996 | Barany et al. |
| 5,538,848 A | 7/1996 | Livak et al. |

(Continued)

FOREIGN PATENT DOCUMENTS

| | | |
|---|---|---|
| CA | 2712773 A1 | 7/2009 |
| CN | 101014720 A | 8/2007 |

(Continued)

OTHER PUBLICATIONS

US 5,962,233 A, 10/1999, Livak et al. (withdrawn)

(Continued)

*Primary Examiner* — Joseph G. Dauner
(74) *Attorney, Agent, or Firm* — Wilson Sonsini Goodrich & Rosati

(57) ABSTRACT

The methods disclosed herein can be used to determine sample integrity, such as sample identity, by using kinship coefficients. Kinship coefficients between two samples can be determined by measuring genetic relatedness in order to determine whether the samples are related or not related.

19 Claims, 6 Drawing Sheets
(4 of 6 Drawing Sheet(s) Filed in Color)

(56) References Cited

U.S. PATENT DOCUMENTS

| | | |
|---|---|---|
| 5,677,195 A | 10/1997 | Winkler et al. |
| 5,705,365 A | 1/1998 | Ryder et al. |
| 5,710,029 A | 1/1998 | Ryder et al. |
| 5,830,711 A | 11/1998 | Barany et al. |
| 5,846,717 A | 12/1998 | Brow et al. |
| 5,854,033 A | 12/1998 | Lizardi |
| 5,888,779 A | 3/1999 | Kacian et al. |
| 5,965,360 A | 10/1999 | Zain et al. |
| 5,985,557 A | 11/1999 | Prudent et al. |
| 5,989,815 A | 11/1999 | Skolnick et al. |
| 5,994,069 A | 11/1999 | Hall et al. |
| 6,001,567 A | 12/1999 | Brow et al. |
| 6,022,692 A | 2/2000 | Coulie et al. |
| 6,027,887 A | 2/2000 | Zavada et al. |
| 6,090,543 A | 7/2000 | Prudent et al. |
| 6,136,182 A | 10/2000 | Dolan et al. |
| 6,225,051 B1 | 5/2001 | Sugiyama et al. |
| 6,251,639 B1 | 6/2001 | Kurn |
| 6,268,142 B1 | 7/2001 | Duff et al. |
| 6,410,278 B1 | 6/2002 | Notomi et al. |
| 6,436,642 B1 | 8/2002 | Gould-Rothberg et al. |
| 6,723,506 B2 | 4/2004 | Fletcher et al. |
| 7,186,514 B2 | 3/2007 | Zavada et al. |
| 7,211,390 B2 | 5/2007 | Rothberg et al. |
| 7,244,559 B2 | 7/2007 | Rothberg et al. |
| 7,264,929 B2 | 9/2007 | Rothberg et al. |
| 7,280,922 B2 | 10/2007 | Mei et al. |
| 7,300,788 B2 | 11/2007 | Matsuzaki et al. |
| 7,319,011 B2 | 1/2008 | Riggins et al. |
| 7,323,305 B2 | 1/2008 | Leamon et al. |
| 7,335,762 B2 | 2/2008 | Rothberg et al. |
| 7,358,061 B2 | 4/2008 | Yamamoto et al. |
| 7,361,488 B2 | 4/2008 | Fan et al. |
| 7,378,233 B2 | 5/2008 | Sidransky et al. |
| 7,407,755 B2 | 8/2008 | Lubinski et al. |
| 7,541,169 B2 | 6/2009 | Freimuth et al. |
| 7,598,052 B2 | 10/2009 | Giordano et al. |
| 7,662,553 B2 | 2/2010 | Lenz |
| 7,767,391 B2 | 8/2010 | Scott et al. |
| 7,901,881 B2 | 3/2011 | Libutti et al. |
| 7,901,888 B2 | 3/2011 | Kebebew |
| 7,927,826 B2 | 4/2011 | Riggins et al. |
| 8,008,009 B2 | 8/2011 | Choquet-Kastylevsky et al. |
| 8,202,692 B2 | 6/2012 | Giordano et al. |
| 8,293,880 B2 | 10/2012 | Cote et al. |
| 8,354,228 B2 | 1/2013 | Ron |
| 8,465,914 B2 | 6/2013 | Brown et al. |
| 8,541,170 B2 | 9/2013 | Kennedy et al. |
| 8,568,971 B2 | 10/2013 | Brown et al. |
| 8,669,057 B2 | 3/2014 | Kennedy et al. |
| 8,802,599 B2 | 8/2014 | Aharonov et al. |
| 8,828,656 B2 | 9/2014 | Bullerdiek et al. |
| 8,877,445 B2 | 11/2014 | Shackney |
| 8,945,829 B2 | 2/2015 | Keutgen et al. |
| 9,040,286 B2 | 5/2015 | Zon et al. |
| 9,074,258 B2 | 7/2015 | Davicioni et al. |
| 9,096,906 B2 | 8/2015 | Aharonov et al. |
| 9,157,123 B2 | 10/2015 | Xing |
| 9,175,352 B2 | 11/2015 | Keutgen et al. |
| 9,206,482 B2 | 12/2015 | Davicioni et al. |
| 9,234,244 B2 | 1/2016 | Zeiger et al. |
| 9,495,515 B1 | 11/2016 | Kennedy et al. |
| 9,587,279 B2 | 3/2017 | Fahey, III et al. |
| 9,617,604 B2 | 4/2017 | Davicioni et al. |
| 9,708,667 B2 | 7/2017 | Barnett-Itzhaki et al. |
| 9,714,452 B2 | 7/2017 | Davicioni et al. |
| 9,856,537 B2 | 1/2018 | Kennedy et al. |
| 9,994,907 B2 | 6/2018 | Davicioni et al. |
| 10,114,924 B2 | 10/2018 | Kennedy et al. |
| 10,236,078 B2 | 3/2019 | Kennedy et al. |
| 10,422,009 B2 | 9/2019 | Davicioni et al. |
| 10,446,272 B2 | 10/2019 | Wilde et al. |
| 10,672,504 B2 | 6/2020 | Kennedy et al. |
| 10,731,223 B2 | 8/2020 | Kennedy et al. |
| 2001/0051344 A1 | 12/2001 | Shalon et al. |
| 2002/0076735 A1 | 6/2002 | Williams et al. |
| 2002/0169137 A1 | 11/2002 | Reiner et al. |
| 2003/0186248 A1 | 10/2003 | Erlander et al. |
| 2003/0190602 A1 | 10/2003 | Pressman et al. |
| 2003/0194734 A1 | 10/2003 | Jatkoe |
| 2004/0019466 A1 | 1/2004 | Minor et al. |
| 2004/0058378 A1 | 3/2004 | Kong et al. |
| 2005/0042222 A1 | 2/2005 | Yamamoto et al. |
| 2005/0048533 A1 | 3/2005 | Sidransky et al. |
| 2005/0137805 A1 | 6/2005 | Lewin et al. |
| 2005/0240357 A1 | 10/2005 | Minor |
| 2005/0250125 A1 | 11/2005 | Novakoff |
| 2005/0266443 A1 | 12/2005 | Croce et al. |
| 2006/0019256 A1 | 1/2006 | Clarke et al. |
| 2006/0019615 A1 | 1/2006 | Ditmer |
| 2006/0035244 A1 | 2/2006 | Riggins et al. |
| 2006/0083744 A1 | 4/2006 | Chen et al. |
| 2006/0088851 A1 | 4/2006 | Erlander et al. |
| 2006/0094061 A1 | 5/2006 | Brys et al. |
| 2006/0105360 A1 | 5/2006 | Croce et al. |
| 2006/0127907 A1 | 6/2006 | Matsubara et al. |
| 2006/0265138 A1 | 11/2006 | Bowtell et al. |
| 2007/0020657 A1 | 1/2007 | Grebe et al. |
| 2007/0031873 A1 | 2/2007 | Wang et al. |
| 2007/0037186 A1 | 2/2007 | Jiang et al. |
| 2007/0048738 A1 | 3/2007 | Donkena et al. |
| 2007/0065833 A1 | 3/2007 | Gupta |
| 2007/0099209 A1 | 5/2007 | Clarke et al. |
| 2007/0105133 A1 | 5/2007 | Clarke et al. |
| 2007/0148667 A1 | 6/2007 | Williams et al. |
| 2007/0148687 A1 | 6/2007 | Bedingham et al. |
| 2007/0161004 A1 | 7/2007 | Brown et al. |
| 2007/0172844 A1 | 7/2007 | Lancaster et al. |
| 2007/0220621 A1 | 9/2007 | Clarke et al. |
| 2007/0238119 A1 | 10/2007 | Yu et al. |
| 2008/0028302 A1 | 1/2008 | Meschkat |
| 2008/0044824 A1 | 2/2008 | Giordano et al. |
| 2008/0124344 A1 | 5/2008 | Combs et al. |
| 2008/0131892 A1 | 6/2008 | Becker et al. |
| 2008/0145841 A1 | 6/2008 | Libutti et al. |
| 2008/0254470 A1 | 10/2008 | Berlin |
| 2008/0274457 A1 | 11/2008 | Eng et al. |
| 2008/0280302 A1 | 11/2008 | Kebebew |
| 2008/0281568 A1 | 11/2008 | Kao et al. |
| 2009/0020433 A1 | 1/2009 | Cohen et al. |
| 2009/0191535 A1 | 7/2009 | Connelly et al. |
| 2009/0204333 A1 | 8/2009 | Friend et al. |
| 2009/0280490 A1 | 11/2009 | Baker et al. |
| 2010/0055704 A1 | 3/2010 | Giordano et al. |
| 2010/0075384 A1 | 3/2010 | Kong et al. |
| 2010/0099093 A1 | 4/2010 | Weaver et al. |
| 2010/0131286 A1 | 5/2010 | Houlgatte et al. |
| 2010/0131432 A1 | 5/2010 | Kennedy et al. |
| 2010/0178653 A1 | 7/2010 | Aharonov et al. |
| 2010/0273674 A1 | 10/2010 | Kamalakaran et al. |
| 2010/0285979 A1 | 11/2010 | Zeiger et al. |
| 2011/0092375 A1 | 4/2011 | Zamore et al. |
| 2011/0152110 A1 | 6/2011 | Vierlinger et al. |
| 2011/0212855 A1 | 9/2011 | Rafnar et al. |
| 2011/0229894 A1 | 9/2011 | Levy et al. |
| 2011/0230372 A1 | 9/2011 | Willman et al. |
| 2011/0287946 A1 | 11/2011 | Gudmundsson et al. |
| 2011/0312520 A1 | 12/2011 | Kennedy et al. |
| 2011/0312530 A1 | 12/2011 | Aharonov et al. |
| 2012/0015839 A1 | 1/2012 | Chinnaiyan |
| 2012/0015843 A1 | 1/2012 | Von Hoff et al. |
| 2012/0115735 A1 | 5/2012 | Vogelstein et al. |
| 2012/0115743 A1 | 5/2012 | Davicioni et al. |
| 2012/0122698 A1 | 5/2012 | Stacey et al. |
| 2012/0122718 A1 | 5/2012 | Reisman |
| 2012/0157334 A1 | 6/2012 | Beaudenon-Huibregtse et al. |
| 2012/0172243 A1 | 7/2012 | Davicioni et al. |
| 2012/0214165 A1 | 8/2012 | Walfish et al. |
| 2012/0220474 A1 | 8/2012 | Kennedy et al. |
| 2013/0023434 A1 | 1/2013 | Van Laar |
| 2013/0142728 A1 | 6/2013 | Beaudenon-Huibregtse et al. |
| 2013/0150257 A1 | 6/2013 | Abdueva et al. |
| 2013/0172203 A1 | 7/2013 | Yeatman et al. |
| 2013/0184999 A1 | 7/2013 | Ding |

(56) References Cited

U.S. PATENT DOCUMENTS

| | | |
|---|---|---|
| 2013/0225662 A1 | 8/2013 | Kennedy et al. |
| 2013/0231258 A1 | 9/2013 | Wilde et al. |
| 2013/0273543 A1 | 10/2013 | Gudmundsson et al. |
| 2013/0302810 A1 | 11/2013 | Latham et al. |
| 2013/0303826 A1 | 11/2013 | Jurisica et al. |
| 2014/0030714 A1 | 1/2014 | Paschke et al. |
| 2014/0080731 A1 | 3/2014 | Davicioni et al. |
| 2014/0087961 A1 | 3/2014 | Sulem et al. |
| 2014/0099261 A1 | 4/2014 | Keutgen et al. |
| 2014/0121126 A1 | 5/2014 | Bivona et al. |
| 2014/0143188 A1 | 5/2014 | Mackey et al. |
| 2014/0228237 A1 | 8/2014 | Kennedy et al. |
| 2014/0243240 A1 | 8/2014 | Soldin et al. |
| 2014/0302042 A1 | 10/2014 | Chin et al. |
| 2014/0315199 A1 | 10/2014 | Rhodes et al. |
| 2014/0315739 A1 | 10/2014 | Aharonov et al. |
| 2014/0349856 A1 | 11/2014 | Schnabel et al. |
| 2014/0349864 A1 | 11/2014 | Kennedy et al. |
| 2014/0371096 A1 | 12/2014 | Umbricht et al. |
| 2015/0038376 A1 | 2/2015 | Tian et al. |
| 2015/0099665 A1 | 4/2015 | Rosenfeld et al. |
| 2015/0141470 A1 | 5/2015 | Garraway et al. |
| 2015/0275306 A1 | 10/2015 | Bernards et al. |
| 2015/0299808 A1 | 10/2015 | Gonzalez Diaz et al. |
| 2015/0307947 A1 | 10/2015 | Basu et al. |
| 2015/0329915 A1 | 11/2015 | Davicioni et al. |
| 2015/0368724 A1 | 12/2015 | Aharonov et al. |
| 2016/0024586 A1 | 1/2016 | Delfour et al. |
| 2016/0032400 A1 | 2/2016 | Gomis et al. |
| 2016/0068915 A1 | 3/2016 | Kennedy et al. |
| 2016/0115546 A1 | 4/2016 | Rosenfeld et al. |
| 2016/0120832 A1 | 5/2016 | Rabinowitz et al. |
| 2016/0312305 A1 | 10/2016 | Kennedy et al. |
| 2016/0312306 A1 | 10/2016 | Kennedy et al. |
| 2016/0312307 A1 | 10/2016 | Kennedy et al. |
| 2016/0312308 A1 | 10/2016 | Kennedy et al. |
| 2017/0016076 A1 | 1/2017 | Barnett-Itzhaki et al. |
| 2017/0145513 A1 | 5/2017 | Kennedy et al. |
| 2017/0145514 A1 | 5/2017 | Kennedy et al. |
| 2017/0166980 A1 | 6/2017 | Fahey, III et al. |
| 2017/0329894 A1 | 11/2017 | Kennedy et al. |
| 2018/0016642 A1 | 1/2018 | Kennedy et al. |
| 2018/0030540 A1 | 2/2018 | Davicioni et al. |
| 2018/0068058 A1 | 3/2018 | Abdueva et al. |
| 2018/0112275 A1 | 4/2018 | Davicioni et al. |
| 2018/0122508 A1 | 5/2018 | Wilde et al. |
| 2018/0127832 A1 | 5/2018 | Kennedy et al. |
| 2018/0349548 A1 | 12/2018 | Walsh et al. |
| 2019/0080047 A1 | 3/2019 | Kennedy et al. |
| 2019/0100805 A1 | 4/2019 | Davicioni et al. |
| 2019/0100809 A1 | 4/2019 | Kennedy et al. |
| 2019/0172551 A1 | 6/2019 | Kennedy et al. |
| 2020/0143944 A1 | 5/2020 | Wilde et al. |
| 2020/0176078 A1 | 6/2020 | Kennedy et al. |
| 2020/0202974 A1 | 6/2020 | Kennedy et al. |
| 2020/0232046 A1 | 7/2020 | Kennedy |

FOREIGN PATENT DOCUMENTS

| | | |
|---|---|---|
| CN | 101501214 A | 8/2009 |
| CN | 103038635 A | 4/2013 |
| EP | 0684315 A1 | 11/1995 |
| EP | 1975245 A1 | 10/2008 |
| EP | 1975252 A1 | 10/2008 |
| EP | 2231874 A2 | 9/2010 |
| EP | 2366800 A1 | 9/2011 |
| EP | 3360978 A2 | 8/2018 |
| JP | 2004526154 A | 8/2004 |
| JP | 2005168432 A | 6/2005 |
| JP | 2005304497 A | 11/2005 |
| JP | 2007513635 A | 5/2007 |
| JP | 2008545400 A | 12/2008 |
| JP | 2008545431 A | 12/2008 |
| JP | 2013212052 A | 10/2013 |
| KR | 20080020083 A | 3/2008 |
| WO | WO-9015070 A1 | 12/1990 |
| WO | WO-9210092 A1 | 6/1992 |
| WO | WO-9309668 A1 | 5/1993 |
| WO | WO-9322684 A1 | 11/1993 |
| WO | WO-9515331 A1 | 6/1995 |
| WO | WO-0120035 A2 | 3/2001 |
| WO | WO-2004091383 A2 | 10/2004 |
| WO | WO-2005005601 A2 | 1/2005 |
| WO | WO-2005085471 A2 | 9/2005 |
| WO | WO-2005100608 A2 | 10/2005 |
| WO | WO-2005005601 A3 | 4/2006 |
| WO | WO-2006047484 A2 | 5/2006 |
| WO | WO-2006062118 A1 | 6/2006 |
| WO | WO-2006110593 A2 | 10/2006 |
| WO | WO-2006127537 A2 | 11/2006 |
| WO | WO-2007038792 A2 | 4/2007 |
| WO | WO-2007038792 A3 | 11/2007 |
| WO | WO-2007126882 A2 | 11/2007 |
| WO | WO-2008104380 A2 | 9/2008 |
| WO | WO-2008119776 A1 | 10/2008 |
| WO | WO-2008130887 A1 | 10/2008 |
| WO | WO-2008104380 A3 | 11/2008 |
| WO | WO-2009020905 A2 | 2/2009 |
| WO | WO-2009026605 A2 | 3/2009 |
| WO | WO-2009029266 A2 | 3/2009 |
| WO | WO-2009037337 A1 | 3/2009 |
| WO | WO-2006127537 A3 | 4/2009 |
| WO | WO-2009042728 A1 | 4/2009 |
| WO | WO-2009068591 A2 | 6/2009 |
| WO | WO-2009079450 A2 | 6/2009 |
| WO | WO-2009087139 A1 | 7/2009 |
| WO | WO-2009096903 A1 | 8/2009 |
| WO | WO-2009111881 A1 | 9/2009 |
| WO | WO-2009126271 A1 | 10/2009 |
| WO | WO-2009143603 A1 | 12/2009 |
| WO | WO-2010000907 A1 | 1/2010 |
| WO | WO-2010018600 A1 | 2/2010 |
| WO | WO-2010018601 A2 | 2/2010 |
| WO | WO-2010056374 A2 | 5/2010 |
| WO | WO-2010073248 A2 | 7/2010 |
| WO | WO-2010056374 A3 | 9/2010 |
| WO | WO-2010073248 A3 | 9/2010 |
| WO | WO-2010099598 A1 | 9/2010 |
| WO | WO-2010123626 A1 | 10/2010 |
| WO | WO-2010124372 A1 | 11/2010 |
| WO | WO-2010127322 A1 | 11/2010 |
| WO | WO-2010129934 A2 | 11/2010 |
| WO | WO-2011079846 A2 | 7/2011 |
| WO | WO-2011143361 A2 | 11/2011 |
| WO | WO-2012055565 A1 | 5/2012 |
| WO | WO-2013063544 A1 | 5/2013 |
| WO | WO-2013086429 A2 | 6/2013 |
| WO | WO-2013086522 A1 | 6/2013 |
| WO | WO-2013088457 A1 | 6/2013 |
| WO | WO-2014043803 A1 | 3/2014 |
| WO | WO-2014151764 A2 | 9/2014 |
| WO | WO-2015071876 A2 | 5/2015 |
| WO | WO-2016141127 A1 | 9/2016 |
| WO | WO-2017065959 A2 | 4/2017 |
| WO | WO-2019023517 A2 | 1/2019 |

OTHER PUBLICATIONS

Dou et al. PLOS Genetics. 2017. 13(9):e1007021. (Year: 2017).*
Kelmemi et al. BMC Medical Genetics. 2015. 16:50. (Year: 2015).*
Hu et al. Nature Protocols. 2006. 1(4):1743. (Year: 2006).*
Blower et al. PLOS One. 2013. 8(10):e77700. (Year: 2013).*
Speed et al. Nature Reviews. 2015. 16:33. (Year: 2015).*
Choi et al. Model Assisted Statistics and Applications. 2017. 12:265-273. (Year: 2017).*
Wessels, et al., A protocol for building and evaluating predictors of disease state based on microarray data, Bioinformatics, 2005, 21:3755-3762.
Abrosimov et al. The cytoplasmic expression of MUC1 in papillary thyroid carcinoma of different histological variants and its correlation with cyclin D1 overexpression. Endocr Pathol. 2007;18(2):68-75.

(56) References Cited

OTHER PUBLICATIONS

Abubaker et al. Clinicopathological analysis of papillary thyroid cancer with PIK3CA alterations in a Middle Eastern population. J Clin Endocrinol Metab. 2008;93(2):611-8.
Adapt, The Peterson Institute for Cancer Research, probesets for ARSG, printed Jan. 10, 2013.
Adapt, The Peterson Institute for Cancer Research, probesets for FREM2, printed Jan. 10, 2013.
Adapt, The Peterson Institute for Cancer Research, probesets for GIMAP2, printed Jan. 10, 2013.
Adapt, The Peterson Institute for Cancer Research, probesets for HRASLS3, printed Jan. 10, 2013.
Adapt, The Peterson Institute for Cancer Research, probesets for PIGN, printed Jan. 10, 2013.
Adapt website. Paterson Institute for Cancer Research. Probesets for AUTS2. Printed Jul. 1, 2014. 2 pages.
Adapt website. Paterson Institute for Cancer Research. Probesets for FXYD6. Printed Jul. 1, 2014. 1 page.
Affymetrix: "Data Sheet Affymetrix(R) Genome-Wide Human SNP Array 6.0", 2007, pp. 1-4, XP002525407. Retrieved from the Internet: URL:http://www.affymetrix.com/support/technical/datasheets/genomewide_snp6_datasheet.pdf.
Affymetrix Technical Note: GeneChip® Gene 1.0 ST Array Design (created Sep. 5, 2007; downloaded from http://media.affymetrix.com/support/technical/technotes/gene_1_0_st_technote.pdf).
Afink, et al. Molecular characterization of iodotyrosine dehalogenase deficiency in patients with hypothyroidism. J Clin Endocrinol Metab. Dec. 2008;93(12):4894-901.
Aggarwal et al. Thyroid carcinoma-associated genetic mutations also occur in thyroid lymphomas. Mod Pathol. vol. 25 No. 9. May 11, 2012. pp. 1203-1211.
Agrawal, et al. Cancer Genome Atlas Research Network. Integrated genomic characterization of papillary thyroid carcinoma. Cell. Oct. 23, 2014;159(3):676-90. doi: 10.1016/j.cell.2014.09.050.
Akester et al. Cancer in the thyroid is not always thyroid cancer. Hormones-Athens-2 (2003): 250-255.
Aldred et al. Caveolin-1 and caveolin-2, together with three bone morphogenetic protein-related genes, may encode novel tumor suppressors down-regulated in sporadic follicular thyroid carcinogenesis. Cancer Res. 2003;63(11):2864-71.
Aldred et al. Papillary and follicular thyroid carcinomas show distinctly different microarray expression profiles and can be distinguished by a minimum of five genes. J Clin Oncol. 2004;22(17):3531-9.
Alexander et al. Preoperative diagnosis of benign thyroid nodules with indeterminate cytology. N Engl J Med. Aug. 23, 2012;367(8):705-15.
Arnesen et al. Expression of N-acetyl transferase human and human Arrest defective 1 proteins in thyroid neoplasms. Thyroid. 2005;15(10):1131-6.
Ashley. Towards precision medicine. Nature Reviews Genetics 17.9 (2016): 507.
Asseroshn et al. The feasibility of using fine needle aspiration from primary breast cancers for cDNA microarray analyses. Clinical Cancer Research 8.3 (2002): 794-801.
Ausubel, et al. Current Protocols in Molecular Biology. Wiley & Sons, New York, 1995.
Auton et al. 1000 Genomes Project Consortium. A global reference for human genetic variation. Nature 526, 7571 (2015): 68.
Bai et al. Mutational analysis of thyroid transcription factor-1 gene (TTF-1) in lung carcinomas. In Vitro Cell Dev Biol Anim. 2008;44(1-2):17-25.
Baldi; et al., "DNA microarrays and gene expression: from experiments to data analysis and modeling. Cambridge university press, 2002."
Baloch, et al. Our approach to follicular-patterned lesions of the thyroid. J Clin Pathol. Mar. 2007;60(3):244-50. Epub Jun. 23, 2006.
Banito et al. Aneuploidy and RAS mutations are mutually exclusive events in the development of well-differentiated thyroid follicular tumours. Clin Endocrinol (Oxf). 2007;67(5):706-11.
Barden et al. Classification of follicular thyroid tumors by molecular signature: results of gene profiling. Clin Cancer Res. 2003;9(5):1792-800.
Baris et al. Transcriptional profiling reveals coordinated up-regulation of oxidative metabolism genes in thyroid oncocytic tumors. J Clin Endocrinol Metab. 2004;89(2):994-1005.
Beaudenon-Huibregtse, et al. Centralized molecular testing for oncogenic gene mutations complements the local cytopathologic diagnosis of thyroid nodules. Thyroid. Oct. 2014;24(10):1479-87. doi: 10.1089/thy.2013.0640. Epub Jun. 18, 2014.
Bessarabova, et al. Bimodal gene expression patterns in breast cancer. BMC Genomics. Feb. 10, 2010;11 Suppl 1:S8. doi: 10.1186/1471-2164-11-S1-S8.
Bolstad, et al. A comparison of normalization methods for high density oligonucleotide array data based on variance and bias. Bioinformatics. Jan. 22, 2003;19(2):185-93.
Boulesteix, et al. Evaluating microarray-based classifiers: an overview. Cancer Inform. 2008;6:77-97. Epub Feb. 29, 2008.
Byron et al. Translating RNA sequencing into clinical diagnostics: opportunities and challenges. Nature Reviews Genetics 17.5 (2016): 257.
Carroll et al. Promising Molecular Techniques for Discriminating Among Follicuar Thyroid Neoplasms. Surgical Oncology, Blackwell Scientific Publ., Oxford, GB, vol. 15, No. 2, Aug. 1, 2006, pp. 59-64.
Centeno et al. Classification of Human Tumors Using Gene Expression Profiles Obtained After Microarray Analysis of Fine-Needle Aspiration Biopsy Samples. Cancer Cytopathology, 2005, 105, 101-109.
Cerutti et al. A preoperative diagnostic test that distinguishes benign from malignant thyroid carcinoma based on gene expression. J Clin Invest. 2004;113(8):1234-42.
Cerutti et al. Diagnosis of suspicious thyroid nodules using four protein biomarkers. Clin Cancer Res. 2006;12(11 Pt 1):3311-8.
Chan, et al. Integrating Transcriptomics and Proteomics. Drug Discovery and Development. Apr. 1, 2006. 4 pages. Published in G&P magazine 2006 vol. 6 No. 3 pp. 20-26.
Chen et al. Restricted kappa/lambda light chain ratio by flow cytometry in germinal center B cells in Hashimoto thyroiditis. Am J Clin Pathol. 2006;125(1):42-8.
Cheng; et al., "A Multi-Cancer Mesenchymal Transition Gene Expression Signature Is Associated with Prolonged Time to Recurrence in Glioblastoma", Plos One, vol. 7, Issue 4, 1-8.
Cheung, et al. Immunohistochemical diagnosis of papillary thyroid carcinoma. Mod Pathol. Apr. 2001;14(4):338-42.
Chevillard et al. Gene expression profiling of differentiated thyroid neoplasms: diagnostic and clinical implications. Clin Cancer Res. 2004;10(19):6586-97.
Chiappetta et al. The antiapoptotic protein BAG3 is expressed in thyroid carcinomas and modulates apoptosis mediated by tumor necrosis factor-related apoptosis-inducing ligand. J Clin Endocrinol Metab. 2007;92(3):1159-63.
Choi et al. Case-control association testing in the presence of unknown relationships. Genetic epidemiology 33.8 (2009): 668-678.
Chung et al. Detection of BRAFV600E mutation on fine needle aspiration specimens of thyroid nodule refines cyto-pathology diagnosis, especially in BRAF600E mutation-prevalent area. Clin Endocrinol (Oxf). 2006;65(5):660-6.
Ciampi et al. BRAF copy number gains in thyroid tumors detected by fluorescence in situ hybridization. Endocr Pathol. 2005;16(2):99-105.
Cibas, et al. The Bethesda System for Reporting Thyroid Cytopathology. Am J Clin Pathol. Nov. 2009;132(5):658-65. doi: 10.1309/AJCPPHLWMI3JV4LA.
Cirulli Uncovering the roles of rare variants in common disease through whole-genome sequencing. Nature Reviews Genetics 11.6 (2010): 415.
Clark et al. Discovery of tissue-specific exons using comprehensive human exon microarrays. Genome Biol. 2007;8(4):R64.
Combined search report and examination report dated Oct. 1, 2013 for GB Application No. 1315760.7.

(56) References Cited

OTHER PUBLICATIONS

Cooper, et al. Management guidelines for patients with thyroid nodules and differentiated thyroid cancer. Thyroid. Feb. 2006;16(2):109-42.
Costa; et al., "New somatic mutations and WNK1-B4GALNT3 gene fusion in papillary thyroid carcinoma", Oncotarget, 2015, 6, 11242-11251.
Crescioli et al. Methimazole inhibits CXC chemokine ligand 10 secretion in human thyrocytes. J Endocrinol. 2007;195(1):145-55.
Cross et al. The promise of molecular profiling for cancer identification and treatment. Clinical medicine & research 2.3 (2004): 147-150.
Delellis et al. C-cell hyperplasia. An ultrastructural analysis. Lab Invest. 1977;36(3):237-48.
Derringer, et al. Malignant lymphoma of the thyroid gland: a clinicopathologic study of 108 cases. Am J Surg Pathol. May 2000;24(5):623-39.
Dettori et al. Aneuploidy in oncocytic lesions of the thyroid gland: diffuse accumulation of mitochondria within the cell is associated with trisomy 7 and progressive numerical chromosomal alterations. Genes Chromosomes Cancer. 2003;38(1):22-31.
Diaz-Uriarte et al. Gene selection and classification of microarray data using random forest. BMC Bioinformatics. 2006;7:3.
Dougherty. The fundamental role of pattern recognition for gene-expression/microarray data in bioinformatics. Pattern recognition. 2005; 38:2226-2228.
Druckenthaner et al. Evidence for Somatostatin receptor 2 in thyroid tissue. Regul Pept. 2007;138(1):32-9.
Durand et al. Evaluation of gene expression profiles in thyroid nodule biopsy material to diagnose thyroid cancer. J Clin Endocrinol Metab. 2008;93(4):1195-202.
Englisch, et al. Chemically Modified Oligonucleotides as Probes and Inhibitors. Angew. Chem. Int. Ed. Eng. 1991; 30:613-629.
Engstrom et al. Systematic evaluation of spliced alignment programs for RNA-seq data. Nature methods 10.12 (2013): 1185.
Erdogan et al. The prevalence of RET/PTC mutations in papillary thyroid cancers in Turkish population and its relation between tumor histopathology and prognostic factors. Exp Clin Endocrinol Diabetes. 2008;116(4):225-30.
Esperante, et al. Identification and characterization of four PAX8 rare sequence variants (p.T225M, p.L233L, p.G336S and p.A439A) in patients with congenital hypothyroidism and dysgenetic thyroid glands. Clin Endocrinol (Oxf). May 2008;68(5):828-35.
Eszlinger et al. Gene expression analysis reveals evidence for inactivation of the TGF-beta signaling cascade in autonomously functioning thyroid nodules. Oncogene. 2004;23(3):795-804.
Eszlinger et al. Meta- and reanalysis of gene expression profiles of hot and cold thyroid nodules and papillary thyroid carcinoma for gene groups. J Clin Endocrinol Metab. 2006;91(5):1934-42.
Eszlinger et al. Perspectives and limitations of microarray-based gene expression profiling of thyroid tumors. Endocr Rev. 2007;28(3):322-38.
Eszlinger, et al. Perspectives for Improved and More Accurate Classification of Thyroid Epithelial Tumors. J Clin Endocrinol Metab. Sep. 2008;93(9):3286-94. Epub Jul. 1, 2008.
European Search Report dated May 25, 2018 for EP172108505.
European search report and opinion dated Mar. 5, 2014 for EP Application No. 11781242.0.
European search report and opinion dated Apr. 28, 2016 for EP 16153243.7.
European search report and search opinion dated Jan. 28, 2013 for Application No. 10772919.6.
European search report and search opinion dated Nov. 27, 2012 for Application No. 09826462.5.
EP16759458.9 European Search Report dated Sep. 6, 2018.
Extended European Search Report dated Apr. 22, 2016 for European Patent Application No. 13838743.6.
Ferrari, et al. An approach to estimate between- and within-group correlation coefficients in multicenter studies: plasma carotenoids as biomarkers of intake of fruits and vegetables. Am J Epidemiol. Sep. 15, 2005;162(6):591-8. Epub Aug. 10, 2005.
Filicori, et al. Risk stratification of indeterminate thyroid fine-needle aspiration biopsy specimens based on mutation analysis. Surgery. Dec. 2011;150(6):1085-91. doi: 10.1016/j.surg.2011.09.009.
Final Office action dated Aug. 28, 2018 for U.S. Appl. No. 13/105,756.
Final Office action dated Sep. 10, 2018 for U.S. Appl. No. 15/694,157.
Finley et al. Advancing the molecular diagnosis of thyroid nodules: defining benign lesions by molecular profiling. Thyroid. 2005;15(6):562-8.
Finley et al. Discrimination of benign and malignant thyroid nodules by molecular profiling. Annals of surgery 240.3 (2004): 425.
Finley et al. Molecular analysis of Hurthle cell neoplasms by gene profiling. Surgery. 2004;136(6):1160-8.
Finley et al. Molecular profiling distinguishes papillary carcinoma from benign thyroid nodules. J Clin Endocrinol Metab. 2004;89(7):3214-23.
Finn, et al. Expression microarray analysis of papillary thyroid carcinoma and benign thyroid tissue: emphasis on the follicular variant and potential markers of malignancy. Virchows Arch. Mar. 2007;450(3):249-60.
Fishel, et al. Meta-analysis of gene expression data: a predictor-based approach. Bioinformatics. Jul. 1, 2007;23(13):1599-606. Epub Apr. 26, 2007.
Fodor, et al. Light-directed, spatially addressable parallel chemical synthesis. Science. Feb. 15, 1991;251(4995):767-73.
Fontaine, et al. Increasing the number of thyroid lesions classes in microarray analysis improves the relevance of diagnostic markers. PLoS One. Oct. 29, 2009;4(10):e7632. doi: 10.1371/journal.pone.0007632.
Fontaine et al. Microarray analysis refines classification of non-medullary thyroid tumours of uncertain malignancy. Oncogene. 2008;27(15):2228-36.
Frampton, et al. Development and validation of a clinical cancer genomic profiling test based on massively parallel DNA sequencing. Nat Biotechnol. Nov. 2013;31(11):1023-31. doi: 10.1038/nbt.2696. Epub Oct. 20, 2013.
Fryknas et al. Molecular markers for discrimination of benign and malignant follicular thyroid tumors. Tumour Biol. 2006;27(4):211-20.
Fujarewicz, et al. A multi-gene approach to differentiate papillary thyroid carcinoma from benign lesions: gene selection using support vector machines with bootstrapping. Endocr Relat Cancer. Sep. 2007;14(3):809-26.
Gait. Chapter 16: Oligoribonucleotides. Antisense Research and Applications, Crookeand Lebleu Eds., CRC Press (pp. 289-302) (1993).
Garcia-Lopez et al. Thyrocytes from autoimmune thyroid disorders produce the chemokines IP-10 and Mig and attract CXCR3+ lymphocytes. J Clin Endocrinol Metab. 2001;86(10):5008-16.
Gardina et al. Alternative splicing and differential gene expression in colon cancer detected by a whole genome exon array. BMC Genomics. 2006;7:325.
Gene Annot Website. Array Probesets for HOMER2, printed Jan. 2016.
Gene Annot website. Probesets for ALDH1B1. Printed Feb. 2018.
Gene Annot website. Probesets for AUTS2. Printed Feb. 2018.
Gene Annot website. Probesets for CFHR1. Printed Feb. 2018.
Gene Annot website. Probesets for CPE. Printed Feb. 2018.
Gene Annot website. Probesets for FN1. Printed Feb. 2018.
Gene Annot website. Probesets for GABRB2. Printed Feb. 2018.
Gene Annot website. Probesets for PLCB1. Printed Feb. 2018.
Gene Annot website. Probesets for PYGL. Printed Feb. 2018.
Gene Annot website. Probesets for ROS1. Printed Feb. 2018.
GeneAnnot website. Probesets for KRAS. Printed Feb. 7, 2017. 2 pages.
GeneAnnot website. Probesets for PROS1. Printed Nov. 8, 2016. 1 page.
GeneAnnot website. Probesets for RXRG. Printed Nov. 8, 2016. 1 page.
Gerstung, et al. Combining gene mutation with gene expression data improves outcome prediction in myelodysplastic syndromes. Nat Commun. Jan. 9, 2015;6:5901. doi: 10.1038/ncomms6901.

(56) References Cited

OTHER PUBLICATIONS

Gill, et al. Nucleic acid isothermal amplification technologies: a review. Nucleosides Nucleotides Nucleic Acids. Mar. 2008;27(3):224-43. doi: 10.1080/15257770701845204.
Giordano et al. Distinct transcriptional profiles of adrenocortical tumors uncovered by DNA microarray analysis. Am J Pathol. 2003;162(2):521-31.
Giordano; et al., "Molecular Classification of Papillary Thyroid Carcinoma; distinct BRAF, RAS and RET/PTC mutation-specific gene expression profiles discovered by DNA microarray Analysis Oncogene", Oncogene, 2005, 24, 6646-6656.
Giordano et al. Organ-specific molecular classification of primary lung, colon, and ovarian adenocarcinomas using gene expression profiles. Am J Pathol. 2001;159(4):1231-8.
Giordano. Genome-wide studies in thyroid neoplasia. Endocrinol Metab Clin North Am. 2008;37(2):311-31, vii-viii.
Gombos, et al. Characterization of microarray gene expression profiles of early stage thyroid tumours. Cancer Genomics Proteomics. Nov.-Dec. 2007;4(6):403-9.
Gonzalez-Campora et al. Blood group antigens in differentiated thyroid neoplasms. Arch Pathol Lab Med. 1998;122(11):957-65.
Greenbaum, et al. Comparing protein abundance and mRNA expression levels on a genomic scale. Genome Biol. 2003;4(9):117. Epub Aug. 29, 2003.
Greenbaum, et al. Interrelating different types of genomic data, from proteome to secretome: 'oming in on function. Genome Res. Sep. 2001;11(9):1463-8.
Griffith, et al. Biomarker panel diagnosis of thyroid cancer: a critical review. Expert Rev Anticancer Ther. Sep. 2008;8(9):1399-413. doi: 10.1586/14737140.8.9.1399.
Griffith et al. Meta-analysis and meta-review of thyroid cancer gene expression profiling studies identifies important diagnostic biomarkers. J Clin Oncol. 2006;24(31):5043-51.
Ha et al. Localized non-Hodgkin lymphoma involving the thyroid gland. Cancer91.4 (2001): 629-635.
Hadd, et al. Targeted, high-depth, next-generation sequencing of cancer genes in formalin-fixed, paraffin-embedded and fine-needle aspiration tumor specimens. J Mol Diagn. Mar. 2013;15(2):234-47. doi: 10.1016/j.jmoldx.2012.11.006. Epub Jan. 13, 2013.
Hamada, et al. Diagnostic usefulness of PCR profiling of the differentially expressed marker genes in thyroid papillary carcinomas. Cancer Lett. Jun. 28, 2005;224(2):289-301. Epub Nov. 18, 2004.
Hartigan, et al. The dip test of unimodality. Annals of Statistics. 1985; 13(1):70-84.
Haugen, et al. Development of a novel molecular classifier to accurately identify benign thyroid nodules in patients with indeterminate FNA cytology. Abstract presented at 14th International Thyroid Congress. Sep. 15, 2010.
Haugen et al. Increased expression of genes encoding mitochondrial proteins in papillary thyroid carcinomas. Thyroid. 2003;13(7):613-20.
Hawthorn, et al. TIMP1 and SERPIN-A overexpression and TFF3 and CRABP1 underexpression as biomarkers for papillary thyroid carcinoma. Head Neck. Dec. 2004;26(12):1069-83.
Hellwig, et al. Comparison of scores for bimodality of gene expression distributions and genome-wide evaluation of the prognostic relevance of high-scoring genes. BMC Bioinformatics. May 25, 2010;11:276. doi: 10.1186/1471-2105-11-276.
Hemmer, et al. DNA copy number changes in thyroid carcinoma. Am J Pathol. May 1999;154(5):1539-47.
Heuer et al. Different cytokine mRNA profiles in Graves' disease, Hashimoto's thyroiditis, and nonautoimmune thyroid disorders determined by quantitative reverse transcriptase polymerase chain reaction (RT-PCR). Thyroid. 1996;6(2):97-106.
Hoshikawa, et al. Hypoxia induces different genes in the lungs of rats compared with mice. Physiol Genomics. Feb. 6, 2003;12(3):209-19.

Hou et al. Genetic alterations and their relationship in the phosphatidylinositol 3-kinase/Akt pathway in thyroid cancer. Clin Cancer Res. 2007;13(4):1161-70.
Huang et al. A genome-wide approach to identify genetic variants that contribute to etoposide-induced cytotoxicity. Proc Natl Acad Sci USA. 2007;104(23):9758-63.
Huang et al. A tool for RNA sequencing sample identity check. Bioinformatics 29.11 (2013): 1463-1464.
Huang et al. Gene expression in papillary thyroid carcinoma reveals highly consistent profiles. Proc Natl Acad Sci USA. 2001;98(26):15044-9.
Hunt, et al. A microdissection and molecular genotyping assay to confirm the identity of tissue floaters in paraffin-embedded tissue blocks Arch Pathol Lab Med. 2003; 127(2):213-217.
International Search Report for PCT/CA2010/000621, completed Jul. 14, 2010.
International search report and written opinion dated Jan. 19, 2012 for PCT Application No. US2011/36143.
International search report and written opinion dated Feb. 25, 2011 for PCT Application No. US2010/034140.
International search report and written opinion dated Feb. 25, 2013 for PCT Application No. US2012/068804.
International Search Report and Written Opinion dated Apr. 4, 2017 for International PCT Patent Application No. PCT/US2016/053578.
International search report and written opinion dated Apr. 17, 2015 for PCT/US2014/026411.
International search report and written opinion dated May 8, 2013 for PCT Application No. US2012/068587.
International Search Report and Written Opinion dated Jun. 2, 2016 for International PCT Patent Application No. PCT/US2016/020583.
International Search Report and Written Opinion dated Nov. 18, 2013 for International PCT Patent Application No. PCT/CA2013/050686.
International search report dated Jul. 29, 2010 for PCT Application No. US2009/06162.
International Search Report for PCT/CA2010/000266, dated Jul. 12, 2010.
Irizarry, et al. Exploration, normalization, and summaries of high density oligonucleotide array probe level data. Biostatistics. Apr. 2003;4(2):249-64.
Ito, et al. Distant and lymph node metastases of thyroid nodules with no pathological evidence of malignancy: a limitation of pathological examination. Endocr J. Oct. 2008;55(5):889-94. Epub Jun. 14, 2008.
Jacques et al. Two-step differential expression analysis reveals a new set of genes involved in thyroid oncocytic tumors. J Clin Endocrinol Metab. 2005;90(4):2314-20.
Jarzab et al. Gene Expression Profile of Papillary Thyroid Cancer: Sources of Variability and Diagnostic Implications. Cancer Res. 2005;65(4):1587-1597.
Joseph et al. Lack of mutations in the thyroid hormone receptor (TR) alpha and beta genes but frequent hypermethylation of the TRbeta gene in differentiated thyroid tumors. J Clin Endocrinol Metab. 2007;92(12):4766-70.
Jovanovic et al. Most multifocal papillary thyroid carcinomas acquire genetic and morphotype diversity through subclonal evolution following the intra-glandular spread of the initial neoplastic clone. J Pathol. 2008;215(2):145-54.
Jun et al. Detecting and estimating contamination of human DNA samples in sequencing and array-based genotype data. The American Journal of Human Genetics 91.5 (2012): 839-848.
Kanehisa. Use of statistical criteria for screening potential homologies in nucleic acid sequences. Nucleic Acids Res. Jan. 11, 1984;12(1 Pt 1):203-13.
Kapadia, et al. Malignant lymphoma of the thyroid gland: a clinicopathologic study. Head Neck Surg. Mar.-Apr. 1982;4(4):270-80.
Kasraeian, et al. A comparison of fine-needle aspiration, core biopsy, and surgical biopsy in the diagnosis of extremity soft tissue masses. Clin Orthop Relat Res. Nov. 2010;468(11):2992-3002. doi: 10.1007/s11999-010-1401-x.

(56) References Cited

OTHER PUBLICATIONS

Katoh et al. Thyroid transcription factor-1 in normal, hyperplastic, and neoplastic follicular thyroid cells examined by immunohistochemistry and nonradioactive in situ hybridization. Mod Pathol. 2000;13(5):570-6.
Kebebew et al. Diagnostic and extent of disease multigene assay for malignant thyroid neoplasms. Cancer. 2006;106(12):2592-7.
Kebebew, et al. The prevalence and prognostic value of BRAF mutation in thyroid cancer. Ann Surg. Sep. 2007;246(3):466-70; discussion 470-1.
Koshkin et al. LNA (locked nucleic acids): An RNA mimic forming exceedingly stable LNA: LNA duplexes. J Am Chem Soc 120:13252-13253 (1998).
Koshkin et al. LNA (locked nucleic acids): synthesis of the adenine, cytosine, guanine 5-methylcytosine, thymine and uracil bicyclonucleoside monomers, oligomerisation, and unprecedented nucleic acid recognition. Tetrahedron 54(14):3607-3630 (1998).
Krause, et al. Characterisation of DEHAL1 expression in thyroid pathologies. Eur J Endocrinol. Mar. 2007;156(3):295-301.
Krawczak, et al. The mutational spectrum of single base-pair substitutions in mRNA splice junctions of human genes: causes and consequences. Hum Genet. Sep.-Oct. 1992;90(1-2):41-54.
Kreula, et al. Sample size in fine needle aspiration biopsy. Br J Surg. Dec. 1989;76(12):1270-2.
Kristensen, et al. Genetic variation in putative regulatory loci controlling gene expression in breast cancer. Proc Natl Acad Sci U S A. May 16, 2006;103(20):7735-40. Epub May 9, 2006.
Kroese et al. Genetic tests and their evaluation: Can we answer the key questions? Genetics in Medicine 6:475-480 (2004).
Kroschwitz. The Concise Encyclopedia of Polymer Science and Engineering. (pp. 858-859) (1990).
Kumar, et al. The first analogues of LNA (locked nucleic acids): phosphorothioate-LNA and 2'-thio-LNA. Bioorg Med Chem Lett. Aug. 18, 1998;8(16):2219-22.
Kwan, et al. Heritability of alternative splicing in the human genome. Genome Res. Aug. 2007;17(8):1210-8.
Lacroix, et al. PAX8 and peroxisome proliferator-activated receptor gamma 1 gene expression status in benign and malignant thyroid tissues. Eur J Endocrinol. Sep. 2004;151(3):367-74.
Lau et al. Thyroid transcription factor-1: a review. Appl Immunohistochem Mol Morphol. 2002;10(2):97-102.
Lee et al. NGSCheckMate: software for validating sample identity in next-generation sequencing studies within and across data types. Nucleic acids research 45.11 (2017).
Lima et al. Thyroid Peroxidase and Thyroglobulin Expression in Normal Human Thyroid Glands. Endocr Pathol. 1998;9(1):333-338.
Lin, et al. Thyroid ultrasonography with fine-needle aspiration cytology for the diagnosis of thyroid cancer. J Clin Ultrasound. Mar.-Apr. 1997;25(3):111-8.
Liu et al. Highly prevalent genetic alterations in receptor tyrosine kinases and phosphatidylinositol 3-kinase/akt and mitogen-activated protein kinase pathways in anaplastic and follicular thyroid cancers. J Clin Endocrinol Metab. 2008;93(8):3106-16.
Love, et al. Moderated estimation of fold change and dispersion for RNA-seq data with DESeq2. Genome Biol. Dec. 5, 2014;15(12):550.
Lubitz et al. 2006;Microarray analysis of thyroid nodule fine-needle aspirates accurately classifies benign and malignant lesions. J Mol Diagn. 8(4):490-8; quiz 528.
Lubitz et al. Molecular analysis of minimally invasive follicular carcinomas by gene profiling. Surgery. 2005;138(6):1042-8; discussion 1048-9.
Lucentini. Gene Association Studies Typically Wrong. The Scientist, 18(24):20 (2004).
Machens et al. Genotype-phenotype based surgical concept of hereditary medullary thyroid carcinoma. World J Surg. 2007;31(5):957-68.
Manichaikul, et al. Robust relationship inference in genome-wide association studies. Bioinformatics. Nov. 15, 2010;26(22):2867-73. doi: 10.1093/bioinformatics/btq559. Epub Oct. 5, 2010.
Marsh, et al. Genome-wide copy number imbalances identified in familial and sporadic medullary thyroid carcinoma. J Clin Endocrinol Metab. Apr. 2003;88(4):1866-72.
Martin. A New Access to 2'-O-Alkylated Ribonucleosides and Properties of 2'-O-Alkylated Oligoribonucleotides. Helv. Chim. Acta. 1995; 78:486-504. (in German with English abstract).
Masini-Repiso et al. Ultrastructural localization of thyroid peroxidase, hydrogen peroxide-generating sites, and monoamine oxidase in benign and malignant thyroid diseases. Hum Pathol. 2004; 35(4):436-46.
Mason, et al. Bimodal distribution of RNA expression levels in human skeletal muscle tissue. BMC Genomics. Feb. 7, 2011;12:98. doi: 10.1186/1471-2164-12-98.
Mazzanti, et al. Using gene expression profiling to differentiate benign versus malignant thyroid tumors. Cancer Res. Apr. 15, 2004;64(8):2898-903.
McCarroll, et al. Integrated detection and population-genetic analysis of SNPs and copy number variation. Nature Genetics 40, 1166-1174 (2008).
Mineva, et al. Differential expression of alphaB-crystallin and Hsp27-1 in anaplastic thyroid carcinomas because of tumor-specific alphaB-crystallin gene (CRYAB) silencing. Cell Stress Chaperones. 2005 Autumn;10(3):171-84.
Mitomo et al. Downregulation of miR-138 is associated with overexpression of human telomerase reverse transcriptase protein in human anaplastic thyroid carcinoma cell lines. Cancer Sci. 2008;99(2):280-6.
Miyamoto; et al., "Potential Marker of Oral Squamous Cell Carcinoma Aggressiveness Detected by Fluorescence in Situ Hybridization in Fine-Needle Aspiration Biopsies", Cancer, American Cancer Society, Jun. 6, 2002, vol. 95, No. 10, 2152-2159.
Mizukami, et al. Late bone metastasis from an encapsulated follicular carcinoma of the thyroid without capsular and vascular invasion. Pathol Int. Jun. 1996;46(6):457-61.
Montero-Conde et al. Molecular profiling related to poor prognosis in thyroid carcinoma. Combining gene expression data and biological information. Oncogene. 2008;27(11):1554-61.
Moreno, et al. Mutations in the iodotyrosine deiodinase gene and hypothyroidism. N Engl J Med. Apr. 24, 2008;358(17):1811-8. doi: 10.1056/NEJMoa0706819.
Murphy et al. Identification of immunohistochemical biomarkers for papillary thyroid carcinoma using gene expression profiling. Hum Pathol. 2008;39(3):420-6.
Nakano et al. Apoptosis-induced decrease of intrathyroidal CD4(+)CD25(+) regulatory T cells in autoimmune thyroid diseases. Thyroid. 2007;17(1):25-31.
Nakashima et al. Foci formation of P53-binding protein 1 in thyroid tumors: activation of genomic instability during thyroid carcinogenesis. Int J Cancer. 2008;122(5):1082-8.
Nakashima et al. RET oncogene amplification in thyroid cancer: correlations with radiation-associated and high-grade malignancy. Hum Pathol. 2007;38(4):621-8.
Nakayama et al. High molecular weight caldesmon positive stromal cells in the capsule of thyroid follicular tumours and tumour-like lesions. J Clin Pathol. 2002;55(12):917-20.
National Cancer Institute web page: "Common Cancer Types", captured by WayBack machine on Dec. 4, 2011, http://www.cancer.gov/cancertopics/types/commoncancers.
NCBI gene report for LOC100131599. Printed Feb. 2018.
Neonakis et al. Expression of calcitonin and somatostatin peptide and mRNA in medullary thyroid carcinoma. World J Surg. 1994;18(4):588-93.
Nielsen, et al. Sequence-selective recognition of DNA by strand displacement with a thymine-substituted polyamide. Science. 254:1497-1500 (1991).
Nikiforova, et al. Highly accurate diagnosis of cancer in thyroid nodules with follicular neoplasm/suspicious for a follicular neoplasm cytology by ThyroSeq v2 next-generation sequencing assay. Cancer. Dec. 1, 2014;120(23):3627-34. doi: 10.1002/cncr.29038. Epub Sep. 10, 2014.
Nikiforova et al. MicroRNA expression profiling of thyroid tumors: biological significance and diagnostic utility. J Clin Endocrinol Metab. 2008;93(5):1600-8.

(56) References Cited

OTHER PUBLICATIONS

Nikiforova, et al. Molecular diagnostics and predictors in thyroid cancer. Thyroid. Dec. 2009;19(12):1351-61. doi: 10.1089/thy.2009.0240.
Nikiforova, et al. Targeted Next-Generation Sequencing Panel (ThyroSeq) for Detection of Mutations in Thyroid Cancer. J Clin Endocrinol Metab. Nov. 2013; 98(11): E1852-E1860.
Notice of allowance dated Mar. 27, 2015 for U.S. Appl. No. 13/254,571.
Notice of Allowance dated Mar. 30, 2017 for U.S. Appl. No. 14/727,801.
Notice of allowance dated Jul. 30, 2015 for U.S. Appl. No. 13/258,429.
Notice of Allowance dated Aug. 21, 2017 for U.S. Appl. No. 15/274,492.
Notice of allowance dated Sep. 13, 2016 for U.S. Appl. No. 12/964,666.
Notice of allowance dated Nov. 28, 2016 for U.S. Appl. No. 14/926,349.
Notice of allowance dated Sep. 13, 2018 for U.S. Appl. No. 15/851,377.
Oerntoft, et al. Genome-wide study of gene copy numbers, transcripts, and protein levels in pairs of non-invasive and invasive human transitional cell carcinomas. Mol Cell Proteomics. Jan. 2002;1(1):37-45.
Office action dated Jan. 5, 2015 for U.S. Appl. No. 14/086,716.
Office Action dated Jan. 12, 2018 for U.S. Appl. No. 13/589,022.
Office action dated Jan. 16, 2013 for U.S. Appl. No. 12/592,065.
Office action dated Jan. 16, 2015 for U.S. Appl. No. 13/258,429.
Office action dated Jan. 16, 2018 for U.S. Appl. No. 13/105,756.
Office action dated Jan. 22, 2016 for U.S. Appl. No. 13/708,439.
Office Action dated Feb. 13, 2017 for U.S. Appl. No. 15/164,241.
Office action dated Feb. 26, 2016 for U.S. Appl. No. 14/926,349.
Office action dated Feb. 27, 2015 for U.S. Appl. No. 13/710,134.
Office Action dated Mar. 2, 2018 for U.S. Appl. No. 13/589,022.
Office action dated Mar. 9, 2016 for U.S. Appl. No. 13/589,022.
Office Action dated Mar. 9, 2017 for U.S. Appl. No. 13/710,134.
Office action dated Mar. 11, 2014 for U.S. Appl. No. 13/254,571.
Office Action dated Mar. 21, 2017 for U.S. Appl. No. 15/164,217.
Office Action dated Mar. 21, 2017 for U.S. Appl. No. 15/164,230.
Office Action dated Mar. 23, 2017 for U.S. Appl. No. 15/164,220.
Office Action dated Mar. 23, 2017 for U.S. Appl. No. 15/274,492.
Office Action dated Mar. 27, 2018 for U.S. Appl. No. 114/153,219.
Office action dated Mar. 29, 2018 for U.S. Appl. No. 14/086,716.
Office action dated Apr. 6, 2012 for U.S. Appl. No. 12/964,666.
Office action dated Apr. 8, 2014 for U.S. Appl. No. 13/258,429.
Office action dated Apr. 18, 2013 for U.S. Appl. No. 13/318,751.
Office action dated Apr. 27, 2015 for U.S. Appl. No. 12/964,666.
Office Action dated May 5, 2017 for U.S. Appl. No. 14/020,183.
Office action dated May 8, 2014 for U.S. Appl. No. 13/105,756.
Office action dated May 9, 2016 for U.S. Appl. No. 12/964,666.
Office action dated May 16, 2016 for U.S. Appl. No. 14/153,219.
Office action dated May 27, 2015 for U.S. Appl. No. 13/105,756.
Office action dated Jun. 6, 2012 for U.S. Appl. No. 12/592,065.
Office action dated Jun. 10, 2014 for U.S. Appl. No. 13/708,439.
Office action dated Jun. 12, 2017 for U.S. Appl. No. 13/105,756.
Office action dated Jun. 15, 2018 for U.S. Appl. No. 15/661,496.
Office action dated Jun. 15, 2018 for U.S. Appl. No. 15/851,377.
Office action dated Jun. 20, 2014 for U.S. Appl. No. 12/964,666.
Office Action dated Jun. 23, 2017 for U.S. Appl. No. 14/153,219.
Office action dated Jun. 29, 2018 for U.S. Appl. No. 15/702,126.
Office Action dated Jul. 5, 2017 for U.S. Appl. No. 14/086,716.
Office action dated Jul. 6, 2011 for U.S. Appl. No. 12/964,666.
Office action dated Jul. 10, 2014 for U.S. Appl. No. 13/589,022.
Office action dated Jul. 26, 2016 for U.S. Appl. No. 13/710,134.
Office action dated Jul. 30, 2014 for U.S. Appl. No. 13/710,134.
Office action dated Aug. 10, 2016 for U.S. Appl. No. 14/086,716.
Office Action dated Aug. 29, 2017 for U.S. Appl. No. 15/185,960.
Office action dated Sep. 2, 2015 for U.S. Appl. No. 14/086,716.
Office action dated Sep. 10, 2018 for U.S. Appl. No. 15/702,217.
Office action dated Sep. 11, 2012 for U.S. Appl. No. 13/318,751.
Office action dated Sep. 11, 2013 for U.S. Appl. No. 13/258,429.
Office action dated Sep. 19, 2016 for U.S. Appl. No. 15/164,217.
Office action dated Sep. 19, 2016 for U.S. Appl. No. 15/164,220.
Office action dated Sep. 19, 2016 for U.S. Appl. No. 15/164,230.
Office Action dated Oct. 12, 2017 for U.S. Appl. No. 13/589,022.
Office action dated Oct. 17, 2013 for U.S. Appl. No. 13/105,756.
Office action dated Nov. 7, 2016 for U.S. Appl. No. 13/105,756.
Office action dated Nov. 17, 2016 for U.S. Appl. No. 13/589,022.
Office action dated Nov. 18, 2016 for U.S. Appl. No. 14/153,219.
Office action dated Nov. 19, 2015 for U.S. Appl. No. 13/710,134.
Office action dated Nov. 29, 2013 for U.S. Appl. No. 13/710,134.
Office action dated Nov. 30, 2016 for U.S. Appl. No. 13/708,439.
Office action dated Dec. 4, 2014 for U.S. Appl. No. 13/254,571.
Office action dated Dec. 17, 2015 for U.S. Appl. No. 13/105,756.
Office Action dated Dec. 26, 2017 for U.S. Appl. No. 15/185,960.
Owens, et al. Metastatic breast carcinoma involving the thyroid gland diagnosed by fine-needle aspiration: a case report. Diagn Cytopathol. Aug. 2005;33(2):110-5.
Pallante et al. MicroRNA deregulation in human thyroid papillary carcinomas. Endocr Relat Cancer. 2006;13(2):497-508.
Pankratz et al. Usual interstitial pneumonia can be detected in transbronchial biopsies using machine learning. Annals of the American Thoracic Society 14.11 (2017): 1646-1654.
Pavelic, et al. Molecular genetic alterations of FHIT and p53 genes in benign and malignant thyroid gland lesions. Mutat Res. Jul. 25, 2006;599(1-2):45-57. Epub May 15, 2006.
Penland, et al. RNA expression analysis of formalin-fixed paraffin-embedded tumors. Lab Invest. Apr. 2007;87(4):383-91.
Phenekos et al. Th1 and Th2 serum cytokine profiles characterize patients with Hashimoto's thyroiditis (Th1) and Graves' disease (Th2). Neuroimmunomodulation. 2004;11(4):209-13.
Pita et al. Gene expression profiling associated with the progression to poorly differentiated thyroid carcinomas. Br J Cancer. 2009;101(10):1782-1791.
Prasad et al. Identification of genes differentially expressed in benign versus malignant thyroid tumors. Clin Cancer Res. 2008;14(11):3327-37.
Puskas, et al. Gene profiling identifies genes specific for well-differentiated epithelial thyroid tumors. Cell Mol Biol (Noisy-le-grand). Sep. 5, 2005;51(2):177-86.
Qian, et al. Renal cell carcinoma metastatic to Hurthle cell adenoma of thyroid. Ann Diagn Pathol. Oct. 2004;8(5):305-8.
Ramzy; Ibrahim., "Clinical cytopathology and aspiration biopsy: Fundamental principles and practice. McGraw Hill Professional, 2001."
Reyes, et al. Identification of kallikrein 7, kallikrein 10 and secreted frizzled-related protein 2 as candidate molecular markers for papillary thyroid carcinoma using microarray analysis. Proc Amer Assoc Cancer Res. 2005, vol. 46, Abstract #38.
Ringel et al. Expression of the sodium iodide symporter and thyroglobulin genes are reduced in papillary thyroid cancer. Mod Pathol. 2001;14(4):289-96.
Robinson et al. A comparison of Affymetrix gene expression arrays. BMC bioinformatics 8.1 (2007): 449.
Robinson et al. A dynamic programming approach for the alignment of signal peaks in multiple gas chromatography-mass spectrometry experiments. BMC bioinformatics 8.1 (2007): 419.
Rodrigues-Serpa, et al. Loss of heterozygosity in follicular and papillary thyroid carcinomas. Cancer Genet Cytogenet. Feb. 2003;141(1):26-31.
Roque, et al. Chromosome imbalances in thyroid follicular neoplasms: a comparison between follicular adenomas and carcinomas. Genes Chromosomes Cancer. Mar. 2003;36(3):292-302.
Ros et al. Thyroid-specific Gene Expression in the Multi-Step Process of Thyroid Carcinogenesis, Biochimie, Masson, Paris, FR, vol. 81, No. 4, Apr. 1, 1999, pp. 389-396.
Roura-Mir et al. Single-cell analysis of intrathyroidal lymphocytes shows differential cytokine expression in Hashimoto's and Graves' disease. Eur J Immunol. 1997;27(12):3290-302.
Saeys, et al. A review of feature selection techniques in bioinformatics. Bioinformatics. Oct. 1, 2007;23(19):2507-17. Epub Aug. 24, 2007.

(56) References Cited

OTHER PUBLICATIONS

Saiz et al. Immunohistochemical expression of cyclin D1, E2F-1, and Ki-67 in benign and malignant thyroid lesions. J Pathol. 2002;198(2):157-62.
Salvatore et al. A cell proliferation and chromosomal instability signature in anaplastic thyroid carcinoma. Cancer Res. 2007;67(21):10148-58.
Sambrook; et al., "Molecular Cloning: A Laboratory Manual. Second edition, Cold Spring Harbor Laboratory Press, 1989."
Sanghvi. Heterocyclic base modifications in nucleic acids and their applications in antisense oligonucleotides. in Antisense Research and Applications. Crooke, S. T. and Lebleu, B., ed., CRC Press. 1993; Ch 15 274-285.
Santarpia et al. Phosphatidylinositol 3-kinase/akt and ras/raf-mitogen-activated protein kinase pathway mutations in anaplastic thyroid cancer. J Clin Endocrinol Metab. 2008;93(1):278-84.
Sapio, et al., Detection of RETIPTC, TRK and BRAF mutations in preoperative diagnosis of thyroid nodules with indeterminate cytological findings, C]Jnical Endocrjnology, 2007, 66: 678-683.
Savagner et al. Defective mitochondrial ATP synthesis in oxyphilic thyroid tumors. J Clin Endocrinol Metab. 2001;86(10):4920-5.
Savagner et al. PGC-1-related coactivator and targets are upregulated in thyroid oncocytoma. Biochem Biophys Res Commun. 2003;310(3):779-84.
Schroeder, et al. The RIN: an RNA integrity number for assigning integrity values to RNA measurements. BMC Mol Biol. Jan. 31, 2006;7:3.
Sheu et al. The C allele of the GNB3 C825T polymorphism of the G protein beta3-subunit is associated with an increased risk for the development of oncocytic thyroid tumours. J Pathol. 2007;211(1):60-6.
Shi, et al. Combined analysis of gene expression, DNA copy number, and mutation profiling data to display biological process anomalies in individual breast cancers. Breast Cancer Res Treat. Apr. 2014;144(3):561-8. doi: 10.1007/s10549-014-2904-z. Epub Mar. 12, 2014.
Shibru, et al. Does the 3-gene diagnostic assay accurately distinguish benign from malignant thyroid neoplasms? Cancer. Sep. 1, 2008;113(5):930-5. doi: 10.1002/cncr.23703.
Shirasawa, S. Susceptibility genes for the development of autoimmune thyroid disease. Nippon Rinsho. Dec. 2006;64(12):2208-14. (Abstract only).
Shvero et al. Immunohistochemical profile and treatment of uncommon types of thyroid carcinomas. Oncol Rep. 2003;10(6):2075-8.
Singh et al. LNA (locked nucleic acids): synthesis and high-affinity nucleic acid recognition. Chem Commun 4:455-456 (1998).
Singh et al. Screening for genetic aberrations in papillary thyroid cancer by using comparative genomic hybridization. Surgery. 2000;128(6):888-93;discussion 893-4.
Singh et al. Synthesis of 2'-amino-LNA: A novel conformationally restricted high-affinity oligonucleotide analogues with a handle. J Bio Chem 63:10035-10039 (1998).
Siragusa et al. MUC1 oncoprotein promotes refractoriness to chemotherapy in thyroid cancer cells. Cancer Res. 2007;67(11):5522-30.
Smith et al. Methylation status of genes in papillary thyroid carcinoma. Arch Otolaryngol Head Neck Surg. 2007;133(10):1006-11.
Smyth. Limma: Linear Models for Microarray Data. In: Bioinformatics and Computational Biology Solutions using R and Bioconductor, R. Gentleman, V. Carey, S. Dudoit, R. Irizarry, W. Huber (eds.), Springer, New York. 2005; pp. 397-420.
Smyth. Linear models and empirical bayes methods for assessing differential expression in microarray experiments. Stat Appl Genet Mol Biol. 2004;3:Article3. Epub Feb. 12, 2004.
Spargo, et al. Detection of M. tuberculosis DNA using thermophilic strand displacement amplification. Mol Cell Probes. Aug. 1996;10(4):247-56.
Stanta et al. The biochemical and immunohistochemical profile of thyroid neoplasia. Pathol Annu. 1988;23 Pt 1: 129-57.

Symmans, et al. Total RNA Yield and Microarray Gene Expression Profiles from Fine-Needle Aspiration Biopsy and Core-Needle Biopsy Samples of Breast Carcinoma. 2003; Cancer 97(12): 2960-2971.
Takano et al. Expression of oncofetal fibronectin messenger ribonucleic acid in fibroblasts in the thyroid: a possible cause of false positive results in molecular-based diagnosis of thyroid carcinomas. J Clin Endocrinol Metab. 2000;85(2):765-8.
Takano et al. Preoperative diagnosis of thyroid papillary and anaplastic carcinomas by real-time quantitative reverse transcription-polymerase chain reaction of oncofetal fibronectin messenger RNA. Cancer Res. 1999;59(18):4542-5.
Tamir et al. Expression and development of a functional plasmalemmal 5-hydroxytryptamine transporter by thyroid follicular cells. Endocrinology. 1996;137(10):4475-86.
Taniguchi et al. Differentiation of follicular thyroid adenoma from carcinoma by means of gene expression profiling with adapter-tagged competitive polymerase chain reaction. Oncology. 2005;69(5):428-35.
Terada. Brain metastasis from thyroid adenomatous nodules or an encapsulated thyroid follicular tumor without capsular and vascular invasion: a case report. Cases J. Jul. 17, 2009;2:7180. doi: 10.4076/1757-1626-2-7180.
Thornton et al. Estimating kinship in admixed populations. The American Journal of Human Genetics 91.1 (2012): 122-138.
Trovisco et al. Molecular Genetics of Papillary Thyroid Carcinoma—Great Expectations . . . Arq Bras Endocrinol Metab, Jul. 1, 2007, pp. 643-653.
Tukey. Exploratory Data Analysis: Past, Present, and Future. Technical Report No. 302. Department of Statistics, Princeton University. 1971-1977. 1993.
Tzen, et al. Is atypical follicular adenoma of the thyroid a preinvasive malignancy? Hum Pathol. Jul. 2003;34(7):666-9.
Ueda, et al. Analysis of PAX8 Gene in Congenital Hypothyroidism Mass Screening Positive Subjects. Folia Endocrinologica Japonica. Mar. 30, 2007, vol. 82, No. 4, p. 859. (in Japanese with English translation).
Ullmannová, et al. The use of housekeeping genes (HKG) as an internal control for the detection of gene expression by quantitative real-time RT-PCR. Folia Biol (Praha). 2003;49(6):211-6.
U.S. Appl. No. 14/020,183 Notice of Allowance dated Apr. 3, 2018.
U.S. Appl. No. 15/626,401 Office Action dated Jan. 25, 2018.
Van Allen et al. Whole-exome sequencing and clinical interpretation of formalin-fixed, paraffin-embedded tumor samples to guide precision cancer medicine. Nature medicine 20.6 (2014): 682.
Van Der Laan, et al. A new algorithm for hybrid hierarchical clustering with visualization and the bootstrap. Journal of Statistical Planning and Inference. Dec. 2003. 117(2):275-303.
Visone et al. MicroRNAs (miR)-221 and miR-222, both overexpressed in human thyroid papillary carcinomas, regulate p27Kip1 protein levels and cell cycle. Endocr Relat Cancer. 2007;14(3):791-8.
Visone et al. Specific microRNAs are downregulated in human thyroid anaplastic carcinomas. Oncogene. 2007;26(54):7590-5.
Wang Et al,, "RNA-seq: a revolutionary tool for transcriptomics", Nature Reviews Genetics, 2009, 10, 57-63.
Wattel, et al. Gene expression in thyroid autonomous adenomas provides insight into their physiopathology. Oncogene. Oct. 20, 2005;24(46):6902-16.
Weber et al. A limited set of human MicroRNA is deregulated in follicular thyroid carcinoma. J Clin Endocrinol Metab. 2006;91(9):3584-91. Epub Jul. 5, 2006.
Weber et al. Genetic classification of benign and malignant thyroid follicular neoplasia based on a three-gene combination. J Clin Endocrinol Metab. 2005;90(5):2512-21.
Weber et al. Silencing of the maternally imprinted tumor suppressor ARHI contributes to follicular thyroid carcinogenesis. J Clin Endocrinol Metab. 2005;90(2):1149-55.
Wessagowit, et al. Normal and abnormal mechanisms of gene splicing and relevance to inherited skin diseases. J Dermatol Sci. Nov. 2005;40(2):73-84. Epub Jul. 27, 2005.

(56) References Cited

OTHER PUBLICATIONS

Wharam, et al. Specific detection of DNA and RNA targets using a novel isothermal nucleic acid amplification assay based on the formation of a three-way junction structure. Nucleic Acids Res. Jun. 1, 2001;29(11):E54-4.
Whitehead, et al. Variation in tissue-specific gene expression among natural populations. Genome Biol. 2005;6(2):R13. Epub Jan. 26, 2005.
Wiseman et al. Molecular phenotyping of thyroid tumors identifies a Marker panel for differentiated thyroid cancer diagnosis. Ann Surg Oncol. 2008;15(10):2811-26.
Wreesmann et al. Genome-wide profiling of papillary thyroid cancer identifies MUC1 as an independent prognostic marker. Cancer Res. 2004;64(11):3780-9.
Written Opinion of the International Searching Authority for PCT/CA2010/000621, dated Aug. 11, 2010.
Wu, et al. A comparative study of 200 fine needle aspiration biopsies performed by clinicians and cytopathologists. Laryngoscope. Jul. 2006;116(7):1212-5.
Xu et al. Differential expression of galectin-1 and galectin-3 in thyroid tumors. Potential diagnostic implications. Am J Pathol. 1995;147(3):815-22.
Yan, et al. Isothermal amplified detection of DNA and RNA. Mol Biosyst. May 2014;10(5):970-1003. doi: 10.1039/c3mb70304e.
Yano et al. Gene expression profiling identifies platelet-derived growth factor as a diagnostic molecular marker for papillary thyroid carcinoma. Clin Cancer Res. 2004;10(6):2035-43.
Yatabe et al. Epidermal growth factor receptor gene amplification is acquired in association with tumor progression of EGFR-mutated lung cancer. Cancer Res. 2008;68(7):2106-11.
Yeh et al. Differentiated thyroid cancer cell invasion is regulated through epidermal growth factor receptor-dependent activation of matrix metalloproteinase (MMP)-2/gelatinase A. Endocr Relat Cancer. 2006;13(4):1173-83.
Yeh et al. Somatic mitochondrial DNA (mtDNA) mutations in papillary thyroid carcinomas and differential mtDNA sequence variants in cases with thyroid tumours. Oncogene. 2000;19(16):2060-6.
Yousefi et al. A SNP panel for identification of DNA and RNA specimens. BMC genomics 19.1 (2018): 90.
Yukinawa, et al. A multi-class predictor based on a probabilistic model: application to gene expression profiling-based diagnosis of thyroid tumors. BMC Genomics. Jul. 27, 2006;7:190.
Zhang, et al. Association between single-nucleotide polymorphisms of BRAF and papillary thyroid carcinoma in a Chinese population. Thyroid. Jan. 2013;23(1):38-44. doi: 10.1089/thy.2012.0228.
Zhang et al. Regulation of tumor necrosis factor-related apoptosis-inducing ligand-induced apoptosis by DJ-1 in thyroid cancer cells. Endocr Relat Cancer. 2008;15(2):535-44.
Zhou et al. RET proto-oncogene mutations are restricted to codons 634 and 918 in mainland Chinese families with MEN2A and MEN2B. Clin Endocrinol (Oxf). 2007;67(4):570-6.
Abratani, Hiroyuki. Characteristic Diagnosis of Cancer by Gene Expression Profiling. Personalized Diagnosis of Cancer by Gene Expression Profiling. English Translation. Journal of Clinical and Experimental Medicine (Igaku No Ayumi), Jun. 1, 2002, vol. 201, No. 9, p. 687-692.
Affymetrix website for HG-U133A probe set list version 2004, Archived NetAffx Annotation Files (http://www.affymetrix.com/estore/catalog/131537/AFFY/Human+Genome+U133A+2.0+Array#1_3) printed Mar. 2015.
Ali et al. Use of the Afirma® Gene Expression Classifier for Preoperative Identification of Benign Thyroid Nodules with Indeterminate Fine Needle Aspiration Cytopathology. PLoS Currents 5:pp. 1-7 (2013).
Bonora et al. Novel germline variants identified in the inner mitochondrial membrane transporter TIMM44 and their role in predisposition to oncocytic thyroid carcinomas. Br J Cancer. 2006;95(11):1529-36.
Brasseur et al. Papillary thyroid carcinoma in a 9-year-old girl with ataxia-telangiectasia. Pediatr Blood Cancer. 2008;50(5):1058-60.
Brozek et al. Thyroid cancer in two siblings with FAP syndrome and APC mutation. Int J Colorectal Dis. 2008;23(3):331-2.
Bugalho et al. Mutation analysis of the RET proto-oncogene and early thyroidectomy: results of a Portuguese cancer centre. Surgery. 2007;141(1):90-5.
Cameselle-Teijeiro et al. Follicular thyroid carcinoma with an unusual glomeruloid pattern of growth. Hum Pathol. 2008;39(10):1540-7.
Carda et al. Anaplastic carcinoma of the thyroid with rhabdomyosarcomatous differentiation: a report of two cases. Virchows Arch. 2005;446(1):46-51.
Castro et al. Adenomas and follicular carcinomas of the thyroid display two major patterns of chromosomal changes. J Pathol. 2005;206(3):305-11.
Castro et al.PAX8-PPARgamma rearrangement is frequently detected in the follicular variant of papillary thyroid carcinoma. J Clin Endocrinol Metab. 2006;91(1):213-20.
Chudova, et al. Molecular classification of thyroid nodules using high-dimensionality genomic data. J Clin Endocrinol Metab. Dec. 2010;95(12):5296-304. doi: 10.1210/jc.2010-1087. Epub Sep. 8, 2010.
Cohen et al. Mutational Analysis of BRAF in Fine Needle Aspiration Biopsies of the Thyroid: A Potential Application for the Preoperative Assessment of Thyroid Nodules. Clinical Cancer Research 10:2761-2765 (Apr. 2004).
De Lellis et al. The pathobiology of the human calcitonin (C)-cell: a review. Pathol Annu. 1981;16(Pt 2):25-52.
Del Senno et al. c-myc oncogene alterations in human thyroid carcinomas. Cancer Detect Prev. 1987;10(3-4):159-66.
Durante, et al. BRAF mutations in papillary thyroid carcinomas inhibit genes involved in iodine metabolism. J Clin Endocrinol Metab. Jul. 2007;92(7):2840-3. Epub May 8, 2007.
Elisei et al. RET genetic screening in patients with medullary thyroid cancer and their relatives: experience with 807 individuals at one center. J Clin Endocrinol Metab. 2007;92(12):4725-9.
Erkkila et al. Probabilistic analysis of gene expression measurements from heterogeneous tissues. Bioinformatics 26(20):2571-2577 (2010).
Foppiani et al. Uncommon association of germline mutations of RET proto-oncogene and CDKN2A gene. Eur J Endocrinol. 2008;158(3):417-22.
Frattini, et al. Alternative mutations of BRAF, RET and NTRK1 are associated with similar but distinct gene expression patterns in papillary thyroid cancer. Oncogene. Sep. 23, 2004;23(44):7436-40.
Gasparre et al. Disruptive mitochondrial DNA mutations in complex I subunits are markers of oncocytic phenotype in thyroid tumors. Proc Natl Acad Sci USA. 2007;104(21):9001-6.
GeneAnnot website. Probesets for AKT1. Printed Aug. 30, 2016. 1 page.
GeneAnnot website. Probesets for ALK. Printed Aug. 30, 2016. 1 page.
GeneAnnot website. Probesets for BRAF. Printed Aug. 30, 2016. 1 page.
GeneAnnot website. Probesets for CALCA. Printed Aug. 30, 2016. 1 page.
GeneAnnot website. Probesets for CTNNB1. Printed Aug. 30, 2016. 1 page.
GeneAnnot website. Probesets for EIF1AY. Printed Aug. 30, 2016. 1 page.
GeneAnnot website. Probesets for IGF2BP2. Printed Aug. 30, 2016. 1 page.
GeneAnnot website. Probesets for KRT7. Printed Aug. 30, 2016. 1 page.
GeneAnnot website. Probesets for MET. Printed Aug. 30, 2016. 1 page.
GeneAnnot website. Probesets for NTRK2. Printed Aug. 30, 2016. 1 page.
GeneAnnot website. Probesets for NTRK3. Printed Aug. 30, 2016. 2 pages.
GeneAnnot website. Probesets for PIK3CA. Printed Aug. 30, 2016. 1 page.

(56) References Cited

OTHER PUBLICATIONS

GeneAnnot website. Probesets for PPARGC1A. Printed Aug. 30, 2016. 1 page.
GeneAnnot website. Probesets for PTEN. Printed Aug. 30, 2016. 2 pages.
GeneAnnot website. Probesets for PTH. Printed Aug. 30, 2016. 1 page.
GeneAnnot website. Probesets for RASA1. Printed Aug. 30, 2016. 1 page.
GeneAnnot website. Probesets for RET. Printed Aug. 30, 2016. 1 page.
GeneAnnot website. Probesets for TP53. Printed Aug. 30, 2016. 1 page.
GeneAnnot website. Probesets for TSHR. Printed Aug. 30, 2016. 1 page.
GeneAnnot website. Probesets for TTF1. Printed Aug. 30, 2016. 1 page.
Gereben et al. Pretranslational regulation of type 2 deiodinase. Thyroid. 2005;15(8):855-64.
Giordano et al. Delineation, functional validation, and bioinformatic evaluation of gene expression in thyroid follicular carcinomas with the PAX8-PPARG translocation. Clin Cancer Res. 2006;12(7 Pt 1):1983-93.
Gould et al. (1987). Synaptophysin expression in neuroendocrine neoplasms as determined by immunocytochemistry. Am J Pathol. 126(2):243-57.
Harach et al. Histology of familial thyroid tumours linked to a gene mapping to chromosome 19p13.2. J Pathol. 1999;189(3):387-93.
He, et al. A susceptibility locus for papillary thyroid carcinoma on chromosome 8q24. Cancer Res. Jan. 15, 2009;69(2):625-31.
He et al. The role of microRNA genes in papillary thyroid carcinoma. Proc Natl Acad Sci USA. 2005;102(52):19075-80.
Hemmer et al. Comparison of benign and malignant follicular thyroid tumours by comparative genomic hybridization. Br J Cancer. 1998;78(8):1012-7.
Holden et al. Tyrosine kinase activating mutations in human malignancies: implications for diagnostic pathology. Exp Mol Pathol. 2008; 85(1):68-75.
Hsu et al. Characterization of a novel tripartite nuclear localization sequence in the EGFR family. J Biol Chem. 2007;282(14):10432-40.
Inaji et al. Demonstration and diagnostic significance of pro-gastrin-releasing peptide in medullary thyroid carcinoma. Oncology. 2000;59(2):122-5.
Ito et al. Simultaneous expression of keratan sulphate epitope (a sulphated poly-N-acetyllactosamine) and blood group ABH antigens in papillary carcinomas of the human thyroid gland. Histochem J. 1996;28(9):613-23.
Jazdzewski et al. Common SNP in pre-miR-146a decreases mature miR expression and predisposes to papillary thyroid carcinoma. Proc Natl Acad Sci USA. 2008;105(20):7269-74.
Jo, et al. Influence of the BRAF V600E mutation on expression of vascular endothelial growth factor in papillary thyroid cancer. J Clin Endocrinol Metab. Sep. 2006;91(9):3667-70. Epub Jun. 13, 2006.
Johansson, et al. Confirmation of a BRAF mutation-associated gene expression signature in melanoma. Pigment Cell Res. Jun. 2007;20(3):216-21.
Kakudo et al. Immunohistochemical study of substance P-like immunoreactivity in human thyroid and medullary carcinoma of the thyroid. J Submicrosc Cytol. 1983;15(2):563-8.
Kang et al. High prevalence of RET, RAS, and ERK expression in Hashimoto's thyroiditis and in papillary thyroid carcinoma in the Korean population. Thyroid. 2007;17(11):1031-8.
Kannengiesser, et al. Gene expression signature associated with BRAF mutations in human primary cutaneous melanomas. Mol Oncol. Apr. 2008;1(4):425-30. doi: 10.1016/j.molonc.2008.01.002. Epub Jan. 12, 2008.
Kawai, et al. Recent Advances of DNA chip application. Latest Situation in DNA Chip Applications. English Translation. Protein Nucleic Acid and Enzyme, Aug. 1, 2000, vol. 45, No. 11, p. 47-53.
Kebebew et al. Diagnostic and prognostic value of angiogenesis-modulating genes in malignant thyroid neoplasms. Surgery. Dec. 2005;138(6):1102-9; discussion 1109-10.
Lauter et al. Mutational analysis of CDKN1B, a candidate tumor-suppressor gene, in refractory secondary/tertiary hyperparathyroidism. Kidney Int. 2008;73(10):1137-40.
Lin et al. Expression of sodium iodide symporter in benign and malignant human thyroid tissues. Endocr Pathol. 2001;12(1):15-21.
Lui et al. 2008;CREB3L2-PPARgamma fusion mutation identifies a thyroid signaling pathway regulated by intramembrane proteolysis. Cancer Res. 68(17):7156-64.
Matsubayashi et al. Gastrin-releasing peptide immunoreactivity in medullary thyroid carcinoma. Cancer. 1984;53(11):2472-7.
Maximo et al. Somatic and germline mutation in GRIM-19, a dual function gene involved in mitochondrial metabolism and cell death, is linked to mitochondrion-rich (Hurthle cell) tumours of the thyroid. Br J Cancer. 2005;92(10):1892-8.
Nam, et al. BRAF V600E mutation analysis of thyroid nodules needle aspirates in relation to their ultrasongraphic classification: a potential guide for selection of samples for molecular analysis. Thyroid. Mar. 2010;20(3):273-9. doi: 10.1089/thy.2009.0226.
Nikolova et al. Genome-wide gene expression profiles of thyroid carcinoma: Identification of molecular targets for treatment of thyroid carcinoma. 2008;Oncol Rep. 20(1):105-21.
Notice of allowance dated Jun. 13, 2013 for U.S. Appl. No. 12/592,065.
Notice of allowance dated Oct. 18, 2013 for U.S. Appl. No. 13/318,751.
Notice of allowance dated Oct. 24, 2018 for U.S. Appl. No. 15/661,496.
Nucera, et al. BRAF(V600E) mutation and the biology of papillary thyroid cancer. Endocr Relat Cancer. Mar. 2008;15(1):191-205. doi: 10.1677/ERC-07-0212.
Office action dated Feb. 4, 2014 for U.S. Appl. No. 13/708,439.
Office action dated Mar. 23, 2015 for U.S. Appl. No. 13/589,022.
Office action dated Sep. 7, 2016 for U.S. Appl. No. 14/727,801.
Office action dated Sep. 8, 2016 for U.S. Appl. No. 15/164,241.
Office action dated Sep. 19, 2018 for U.S. Appl. No. 15/096,739.
Oler, et al. Gene expression profiling of papillary thyroid carcinoma identifies transcripts correlated with BRAF mutational status and lymph node metastasis. Clin Cancer Res. Aug. 1, 2008;14(15):4735-42. doi: 10.1158/1078-0432.CCR-07-4372.
Panicker et al. A common variation in deiodinase 1 gene DIO1 is associated with the relative levels of free thyroxine and triiodothyronine. J Clin Endocrinol Metab. 2008;93(8):3075-81.
Pavey, et al. Microarray expression profiling in melanoma reveals a BRAF mutation signature. Oncogene. May 20, 2004;23(23):4060-7.
Pinto et al. mRNA expression of tachykinins and tachykinin receptors in different human tissues. Eur J Pharmacol. 2004;494(2-3):233-9.
Rosai et al. Pitfalls in the diagnosis of thyroid neoplasms. Pathol Res Pract. 1987;182(2):169-79.
Rosen et al. A six-gene model for differentiating benign from malignant thyroid tumors on the basis of gene expression. Surgery. 2005;138(6):1050-6; discussion 1056-7.
Rowe et al. Utility of BRAF V600E Mutation Detection in Cytologically Indeterminate Thyroid Nodules. CytoJoural 3(10):1-10 (Apr. 2006).
Satake et al. Overview of the primary structure, tissue-distribution, and functions of tachykinins and their receptors. Curr Drug Targets. 2006;7(8):963-74.
Schiff, et al. Epidermal growth factor receptor (EGFR) is overexpressed in anaplastic thyroid cancer, and the EGFR inhibitor gefitinib inhibits the growth of anaplastic thyroid cancer. Clin Cancer Res. Dec. 15, 2004;10(24):8594-602.
Subramaniam et al. Clonal characterization of sporadic cribriform-morular variant of papillary thyroid carcinoma by laser microdissection-based APC mutation analysis. Am J Clin Pathol. 2007;128(6):994-1001.
Supplementary European search report and opinion dated Oct. 12, 2016 for EP Application No. 14770813.
Takakura et al. Oncogenic role of miR-17-92 cluster in anaplastic thyroid cancer cells. Cancer Sci. 2008;99(6):1147-54.

(56) References Cited

OTHER PUBLICATIONS

Tetzlaff et al. Differential expression of miRNAs in papillary thyroid carcinoma compared to multinodular goiter using formalin fixed paraffin embedded tissues. Endocr Pathol. 2007;18(3):163-73.
Thompson et al. Primary smooth muscle tumors of the thyroid gland. Cancer. 1997;79(3):579-87.
Tian, et al. A combined oncogenic pathway signature of BRAF, KRAS and PI3KCA mutation improves colorectal cancer classification and cetuximab treatment prediction. Gut. Apr. 2013;62(4):540-9. doi: 10.1136/gutjnl-2012-302423. Epub Jul. 14, 2012.
Tian, et al. Effects of Gender on Gene Expression in the Blood of Ischemic Stroke Patients. Journal of Cerebral Blood Flow & Metabolism. J Cereb Blood Flow Metab. May 2012;32(5):780-91. doi: 10.1038/jcbfm.2011.179. Epub Dec. 14, 2011.
Todaro et al. Autocrine production of interleukin-4 and interleukin-10 is required for survival and growth of thyroid cancer cells. Cancer Res. 2006;66(3):1491-9.
Unger et al. Array CGH demonstrates characteristic aberration signatures in human papillary thyroid carcinomas governed by RET/PTC. Oncogene. 2008;27(33):4592-602.
U.S. Appl. No. 14/851,864 Office Action dated Nov. 9, 2018.
Vasko, et al. Gene expression and functional evidence of epithelial-to-mesenchymal transition in papillary thyroid carcinoma invasion. Proc Natl Acad Sci U S A. Feb. 20, 2007;104(8):2803-8. Epub Feb. 12, 2007.
Viale et al. Coexpression of cytokeratins and vimentin in normal and diseased thyroid glands. Lack of diagnostic utility of vimentin immunostaining. Am J Surg Pathol. 1989;13(12):1034-40.
Viney et al. Regulation of the cell-specific calcitonin/calcitonin gene-related peptide enhancer by USF and the Foxa2 forkhead protein. J Biol Chem. 2004;279(48):49948-55.
Wang et al. Association of the T1799A BRAF mutation with tumor extrathyroidal invasion, higher peripheral platelet counts, and overexpression of platelet-derived growth factor-B in papillary thyroid cancer. Endocr Relat Cancer. 2008;15(1):183-90.
Wang et al. The expression analysis of ICOS-L on activated T cells and immature dendritic cells as well as malignant B cells and Grave's-disease-derived thyroid tissues by two novel mAbs against human ICOS-L. Tissue Antigens. 2007;69(1):62-72.
Watanabe et al. Decrease of intrathyroidal CD161+Valpha24+Vbeta11+ NKT cells in Graves' disease. Endocr J. 2008; 55(1):199-203.
Wu et al. Uncommon mutation, but common amplifications, of the PIK3CA gene in thyroid tumors. J Clin Endocrinol Metab. 2005;90(8):4688-93.
Yang et al. C-myc, N-myc, N-ras, and c-erb-B: lack of amplification or rearrangement in human medullary thyroid carcinoma and a derivative cell line. Anticancer Res. 1990;10(1):189-92.
Yoon et al. Identification of a novel noncoding RNA gene, NAMA, that is downregulated in papillary thyroid carcinoma with BRAF mutation and associated with growth arrest. Int J Cancer. 2007;121(4):767-75.
Zabel et al. S-100 protein and neuron-specific enolase in parathyroid glands and C-cells of the thyroid. Histochemistry. 1987;86(4):389-92.
Zanna et al. Trop-1 are conserved growth stimulatory molecules that mark early stages of tumor progression. Cancer. 2007;110(2):452-64.
Zeng et al. The contributions of oestrogen receptor isoforms to the development of papillary and anaplastic thyroid carcinomas. J Pathol. 2008;214(4):425-33.
Zhang, et al. CDC23 Regulates Cancer Cell Phenotype and is Overexpressed in Papillary Thyroid Cancer. Endocr Relat Cancer. Endocr Relat Cancer. Nov. 28, 2011;18(6):731-42. doi: 10.1530/ERC-11-0181. Print 2011.
Zhu et al. U1 snRNP-dependent function of TIAR in the regulation of alternative RNA processing of the human calcitonin/CGRP pre-mRNA. Mol Cell Biol. 2003;23(17):5959-71.
Accession N M_000441. 2008. *Homo sapiens* solute carrier family 26, member 4 (SLC26A4), mRNA (Year: 2008).

Adams, J.U., The Human Genome project set out to sequence all of the 3 billion nucleotides in the human genome. Exactly how was this daunting task done with such incredible speed and accuracy? DNA sequencing technologies. Nature Education, 2008; 1(1):193, pp. 1-6.
Chung KW. et al., Gene expression profiling of papillary thyroid carcinomasin Korean patients by oligonucleotide microarrays. Journal of the Korean Surgical Society, Apr. 26, 2012, vol. 82, No. 5, pp. 271-280whole document.
Co-pending U.S. Appl. No. 15/096,739, inventors Giulia; C. Kennedy et al., filed Apr. 12, 2016.
Co-pending U.S. Appl. No. 16/279,252, inventors Kennedygiulia; C. et al., filed Feb. 19, 2019.
Co-pending U.S. Appl. No. 16/422,109, inventors Kennedygiulia; C. et al., filed May 24, 2019.
Co-pending U.S. Appl. No. 16/534,889, inventors Kennedygiulia; C. et al., filed Aug. 7, 2019.
Co-pending U.S. Appl. No. 16/541,041, inventors Kennedygiulia; C. et al., filed Sep. 5, 2019.
Co-pending U.S. Appl. No. 16/594,586, inventors Kennedygiulia; C. et al., filed Oct. 7, 2019.
Co-pending U.S. Appl. No. 16/721,783, inventors Kennedygiulia; C. et al., filed Dec. 19, 2019.
Co-pending U.S. Appl. No. 16/820,537, inventors Kennedygiulia; C. et al., filed Mar. 16, 2020.
Co-pending U.S. Appl. No. 16/820,599, inventors Kennedy; Giulia C. et al., filed Mar. 16, 2020.
Co-pending U.S. Appl. No. 16/886,477, inventors Kennedy; Giulia C. et al., filed May 28, 2020.
Co-pending U.S. Appl. No. 16/910,039, inventors Kennedy; Giulia C. et al., filed Jun. 23, 2020.
Co-pending U.S. Appl. No. 17/003,228, inventors Kennedygiulia; C. et al., filed Aug. 26, 2020.
Co-pending U.S. Appl. No. 17/084,593, inventors Kennedygiulia; C. et al., filed Oct. 29, 2020.
Co-pending U.S. Appl. No. 17/084,622, inventors Kennedygiulia; C. et al., filed Oct. 29, 2020.
Co-pending U.S. Appl. No. 17/145,563, inventors Kennedygiulia; C. et al., filed Jan. 11, 2021.
Co-pending U.S. Appl. No. 17/157,876, inventors Kennedygiulia; C. et al., filed Jan. 25, 2021.
Co-pending U.S. Appl. No. 17/169,397, inventors Davicionielai et al., filed Feb. 5, 2021.
Co-pending U.S. Appl. No. 17/322,681, inventors Kennedygiulia; C. et al., filed May 17, 2021.
Co-pending U.S. Appl. No. 17/338,585, inventors Kennedygiulia; C. et al., filed Jun. 3, 2021.
Co-pending U.S. Appl. No. 17/338,587, inventors Kennedygiulia; C. et al., filed Jun. 3, 2021.
Cortes et al. Support-vector networks. Machine Learning. 1995; 20:273-297.
Delehaye, et al., Elevated levels of calcitonin mRNA: A marker for the spontaneous development of medullary thyroid carcinoma in rats. Biochemical and biophysical research communications, Mar. 15, 1989; 159(2): 528-535.
Delibasis, et al., "Computer-Aided Diagnosis of Thyroid Malignancy Using an Artificial Immune System Classification Algorithm," IEEE Transactions on Information Technology in Biomedicine, vol. 13, No. 5, pp. 680-686, Sep. 2009.
Endocrine website. http://www.endocrineweb.com/noduleus.html (Accessed Dec. 9, 2011) (last update Oct. 12, 2010).
EP18191806.1 European Search Report dated Jun. 28, 2019.
EP20178664.7 European Search Report dated May 3, 2021.
Eszlinger et al., Perspectives and Limitations of Microarray-Based Gene Expression Profiling of Thyroid Tumors. Endocrine Reviews, 2007; 28:322-338.
Frohman on Beyond Classic RACE (Rapid Amplification of eDNA Ends) PCR Methods and Applications vol. 4, pp. S40-S58 (Year: 1994).
GeneAnnot Search for Affymetrix HG-U 133A microarray pro besets for TIMP1, printed Dec. 2018.
GeneAnnot Search for Affymetrix HG-U 133A microarray probesets for SLCA4, printed Dec. 2018.

(56) References Cited

OTHER PUBLICATIONS

Geneloc CYP4F11. Geneloc Integrated Map for Chromosome 19: Exon structure for CYP4F11, https://genecards.weizmann.ac.il/geneloc-bin/exon_struct.pl?disp_name=CYP4F11&chr_nr=19, accessed Dec. 13, 2019, pp. 1-2 (Year: 2019).
Goy, A. et al., 'The feasibility of gene expression profiling generated in fine-needle aspiration specimensfrom patients with follicular lymphoma and diffuse large B-cell lymphoma', Cancer. 2006 vol. 108 pp. 10-20.
Human hg 19 chr5 (Human hg 19 chr5: 136368834-136368864 UCSC Genome Browser v410, 2009) (Year: 2009).
Human hg19 chr11 (Human hg19 chr11 :30509671-30509898 UCSC Genome Browser v410, 2009) (Year: 2009).
Ji et. al., Long-term impact of initial surgical and medical therapy on young patients with papillary thyroid cancer and bilateral cervical metastases. Chinese Medical Journal, 2008; 121 (1) :63-66.
Kim et al. Diagnostic use of molecular markers in the evaluation of thyroid nodules. Endocrine Practice Sep./Oct. 2012, vol. 18, No. 5, pp. 796-802 (Year: 2012).
Liu, Y. 'Active learning with support vector machine applied to gene expression data for cancer classification', J Chem Inf Comput Sci. 2004, vol. 44, pp. 1936-1941.
Lubitz, et al., The differentiation of Benign and malignant thyroid nodules. Advances in sur. Jan. 1, 2005; 39(1): 355-377.
Nikiforov et al. Impact of Mutational Testing on the Diagnosis and Management of Patients with Cytologically Indeterminate Thyroid Nodules: A Prospective Analysis of 1056 FNA Samples Journal of Clinical Endocrinology and Metabolism vol. 96, pp. 3390-3397 (Year: 2011).
Office Action dated Nov. 20, 2018 for U.S. Appl. No. 13/589,022.
Office Action dated Nov. 29, 2018 for U.S. Appl. No. 15/626,401.
Office Action dated Dec. 12, 2018 for U.S. Appl. No. 14/086,716.
Office action dated Dec. 13, 2018 for U.S. Appl. No. 14/153,219.
Oshlack et al. FRom RNA-seq reads to differential expression results Genome Biology vol. 11, article 220 (Year: 201 0).
Paull, D.E. et al., 'Gene expression profiles from needle biopsies provide useful signatures of non-smallcell lung carcinomas', Biomark Insights. 2007, vol. 2, pp. 253-259.
PCT/US2018/043984 International Search Report and Written Opinion dated Jan. 21, 2019.
Pusztai, L. et al., 'Gene expression profiles obtained from fine-needle aspirations of breast cancer reliablyidentify routine prognostic markers and reveal large-scale molecular differences between estrogen-negative andestrogen-positive tumors', Clin Cancer Res. 2003, vol. 9, pp. 2406-2415.
Ramaswamy, et al. "Multiclass cancer diagnosis using tumor gene expression signatures" Proceedings of the National Academy of Sciences Dec. 2001, 98 (26) 15149-15154.
Riley, et al., Ectopic synthesis of high-Mr calcitonin by the BEN lung carcinoma cell line reflects aberrant proteolytic processing. FEBS lettes, Mar. 17, 1986; 198(1): 71-79.
Shipp, et al. Diffuse large B-cell lymphoma outcome prediction by gene-expression profiling and supervised machine learning. Nat Med. Jan. 2002;8(1):68-74.
Siraj, et al., Genome-wide expression analysis of middle eastern papillary thyroid cancer reveals c-MET as a novel target for cancer therapy. The journal of pathology. Oct. 1, 2007; 213(2): 190-199.
Song Kim, et al., Phase II clinical and exploratory biomarker study of dacomitinib in recurrent and/or metastatic esophageal squamous cell carcinoma. Oncotarget, Oct. 9, 2015, vol. 6, No. 42, pp. 44971-44984.
Trovato, et al., Expression of the hepatocyte growth factor and c-met in normal thyroid, non-neoplastic, and neoplastic nodules. Thyroid, Jan. 1, 1998; 8(2): 125-131.
U.S. Appl. No. 14/153,219 Notice of Allowance dated Oct. 27, 2020.
U.S. Appl. No. 14/153,219 Office Action dated Apr. 17, 2020.
U.S. Appl. No. 14/153,219 Office Action dated Sep. 26, 2019.
U.S. Appl. No. 14/851,864 Office Action dated May 14, 2019.
U.S. Appl. No. 15/096,739 Office Action dated Jun. 6, 2019.
U.S. Appl. No. 15/096,739 Office Action dated Mar. 13, 2020.
U.S. Appl. No. 15/096,739 Office Action dated Sep. 24, 2020.
U.S. Appl. No. 15/185,960 Office Action dated Dec. 21, 2018.
U.S. Appl. No. 15/440,575 Office Action dated Apr. 9, 2019.
U.S. Appl. No. 15/440,575 Office Action dated Aug. 13, 2020.
U.S. Appl. No. 15/440,575 Office Action dated Dec. 23, 2019.
U.S. Appl. No. 15/440,575 Office Action dated Mar. 22, 2021.
U.S. Appl. No. 15/618,656 Office Action dated Aug. 18, 2020.
U.S. Appl. No. 15/618,656 Office Action dated Dec. 18, 2019.
U.S. Appl. No. 15/626,401 Notice of Allowance dated Jul. 15, 2019.
U.S. Appl. No. 15/626,401 Notice of Allowance dated May 10, 2019.
U.S. Appl. No. 15/661,496 Notice of Allowance dated Feb. 11, 2019.
U.S. Appl. No. 15/694,157 Office Action dated Mar. 7, 2019.
U.S. Appl. No. 15/702,126 Notice of Allowance dated Jun. 8, 2020.
U.S. Appl. No. 15/702,126 Office Action dated Apr. 19, 2019.
U.S. Appl. No. 15/702,217 Notice of Allowance dated Jun. 18, 2019.
U.S. Appl. No. 16/353,248 Notice of Allowance dated Apr. 20, 2020.
U.S. Appl. No. 16/353,248 Notice of Allowance dated Feb. 28, 2020.
U.S. Appl. No. 16/353,248 Office Action dated Oct. 28, 2019.
Xing et al. BRAF V600E and TERT Promoter Mutations Cooperatively Identify the Most Aggressive Papillary Thyroid Cancer With Highest Recurrence Journal of Clinical Oncology vol. 32, pp. 2718-2726 (Year: 2014).
Zhang, et al., Identifying driver mutations from sequencing data of heterogeneous tumors in the era of personalized genome sequencing. Briefings in bioinformatics 15.2 (2014): 244-255.

* cited by examiner

METHODS AND SYSTEMS FOR DETERMINING BIOLOGICAL SAMPLE INTEGRITY

CROSS-REFERENCE

This application claims priority to U.S. Provisional Application No. 62/524,393, filed Jun. 23, 2017, which is incorporated herein by reference in its entirety.

BACKGROUND

Precision medicine is an important paradigm in the clinical management of disease, particularly in oncology. Next generation sequencing (NGS) may allow sequencing of deoxyribonucleic acid (DNA) including: whole genomes, exomes, targeted genomic regions of interest. NGS may also allow the querying of ribonucleic acid (RNA), such as the transcriptome through RNA-seq. These technologies can reveal disease-related genomic alterations or aberrations, including single nucleotide variants (SNVs), copy number variants (CNVs), and genomic rearrangements. In addition to searching for disease-causing markers, numerous germline single nucleotide polymorphisms (SNPs) are queried as well.

SUMMARY

In the clinical setting, samples are processed in high throughput fashion, and are handled from accessioning through final output and patient report. Because treatment decisions can be based on a diagnostic test result, it is important to ensure that the sample associated with the report is the sample that was derived from the patient. Additionally, during the development of novel clinical tests, sample swaps can affect stated test performance by introducing errors into the validation set.

In an aspect, the present disclosure provides a method for processing or analysis of a biological sample of a subject. The method comprises (a) obtaining a plurality of biological samples comprising the biological sample from the subject, wherein the biological sample comprises a plurality of transcripts corresponding to at least one gene having one or more genetic aberrations; (b) subjecting the plurality of transcripts to nucleic acid amplification under conditions that are sufficient to amplify the plurality of transcripts, thereby generating amplification products; (c) subjecting the amplification products of (b) to a sequencing assay to generate an expression profile indicative of a detected presence of the plurality of transcripts; and (d) using a computer classifier to process the expression profile generated in (c) to identify the biological sample as belonging to the subject, wherein the computer classifier performs a kinship analysis of the biological sample from the subject against one or more other biological samples of the plurality of biological samples.

In some embodiments, the method further comprising, prior to (a), selecting the one or more genetic aberrations In some embodiments, the one or more genetic aberrations are selected to have a sequencing coverage of 20× or more. In some embodiments, the one or more genetic aberrations are preselected to have an average sequencing coverage of 200× or less. In some embodiments, the one or more genetic aberrations are preselected to have an average sequencing coverage of about 30× to about 700×. In some embodiments, the one or more genetic aberrations are preselected to have at least 10% heterozygosity.

In some embodiments, (d) comprises determining kinship coefficients based on at least a subset of the one or more genetic aberrations in the biological sample corresponding to genetic aberrations in one or more different biological samples in the plurality of biological samples. In some embodiments, the kinship coefficients are determined using a method of moment (MOM), a shared genotypes ratio (SGR), a maximum-likelihood estimator (MLE), or any of identity by descent sharing probabilities.

In some embodiments, the nucleic acid amplification comprises performing microarray, serial analysis of gene expression (SAGE), reverse transcription polymerase chain reaction (PCR), or quantitative PCR. In some embodiments, the method further using a probe set with a plurality of probes that specifically binds to the plurality of transcripts to enrich for the plurality of transcripts. In some embodiments, the plurality of probes comprises ribonucleic acid, synthetic nucleotides or a combination thereof. In some embodiments, the method further comprises extracting ribonucleic acid molecules from the biological sample. In some embodiments, the method further comprises purifying messenger ribonucleic acid molecules (mRNA) from the biological sample.

In some embodiments, when the biological sample is identified as belonging to the subject, repeating (a)-(d) with another biological sample that is suspected of being from the subject. In some embodiments, the method further comprises, upon identifying the biological sample as belonging to the subject, classifying the biological sample of the subject as being malignant, benign or normal for a disease. In some embodiments, when the biological sample is classified as malignant, further comprising using the expression profile generated in (d) to classify the biological sample as having a cancer subtype. In some embodiments, the cancer subtype comprises papillary thyroid cancer (PTC), follicular thyroid cancer (FTC), medullary thyroid cancer (MTC), or anaplastic thyroid cancer (ATC). In some embodiments, the disease is thyroid cancer or lung cancer.

In some embodiments, the method further comprises, prior to (b), subjecting a first portion of the biological sample to cytology to identify the biological sample as ambiguous or suspicious, wherein the plurality of transcripts in (a) is from a second portion of the biological sample. In some embodiments, the first portion is different from the second portion. In some embodiments, the biological sample is selected from a plurality of samples suspected as being from the subject. In some embodiments, the plurality of samples comprises from 2 to 200 samples. In some embodiments, the method further comprises obtaining the biological sample from the subject. In some embodiments, the biological sample comprises a needle aspirate or a tissue swab. In some embodiments, the biological sample comprises an epithelial tissue, a thyroid tissue, a lung tissue, or any combination thereof. In some embodiments, the plurality of biological samples comprises two or more biological samples from the subject. In some embodiments, identifying in (d) comprises identifying whether the biological sample is a biological replicate or a technical replicate.

In some embodiments, the one or more genetic aberrations comprise one or more single nucleotide polymorphisms (SNPs). In some embodiments, the computer classifier comprises a trained algorithm trained on another plurality of biological samples independent of the plurality of biological samples. In some embodiments, the biological sample is identified as belonging to the subject at an accuracy of at least 80%. In some embodiments, the biological sample is identified as belonging to the subject at an accuracy of at least 90%. In some embodiments, the biological sample is identified as belonging to the subject at an accuracy of at least 95%.

Additional aspects and advantages of the present disclosure will become readily apparent to those skilled in this art from the following detailed description, wherein only illustrative embodiments of the present disclosure are shown and described. As will be realized, the present disclosure is capable of other and different embodiments, and its several details are capable of modifications in various obvious respects, all without departing from the disclosure. Accordingly, the drawings and description are to be regarded as illustrative in nature, and not as restrictive.

INCORPORATION BY REFERENCE

All publications, patents, and patent applications mentioned in this specification are herein incorporated by reference to the same extent as if each individual publication, patent, or patent application was specifically and individually indicated to be incorporated by reference. To the extent publications and patents or patent applications incorporated by reference contradict the disclosure contained in the specification, the specification is intended to supersede and/or take precedence over any such contradictory material.

BRIEF DESCRIPTION OF THE DRAWINGS

The patent or application file contains at least one drawing executed in color. Copies of this patent or patent application publication with color drawings will be provided by the Office upon request and payment of the necessary fee.

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings (also "Figure" and "FIG." herein), of which:

DETAILED DESCRIPTION

Figure 1:
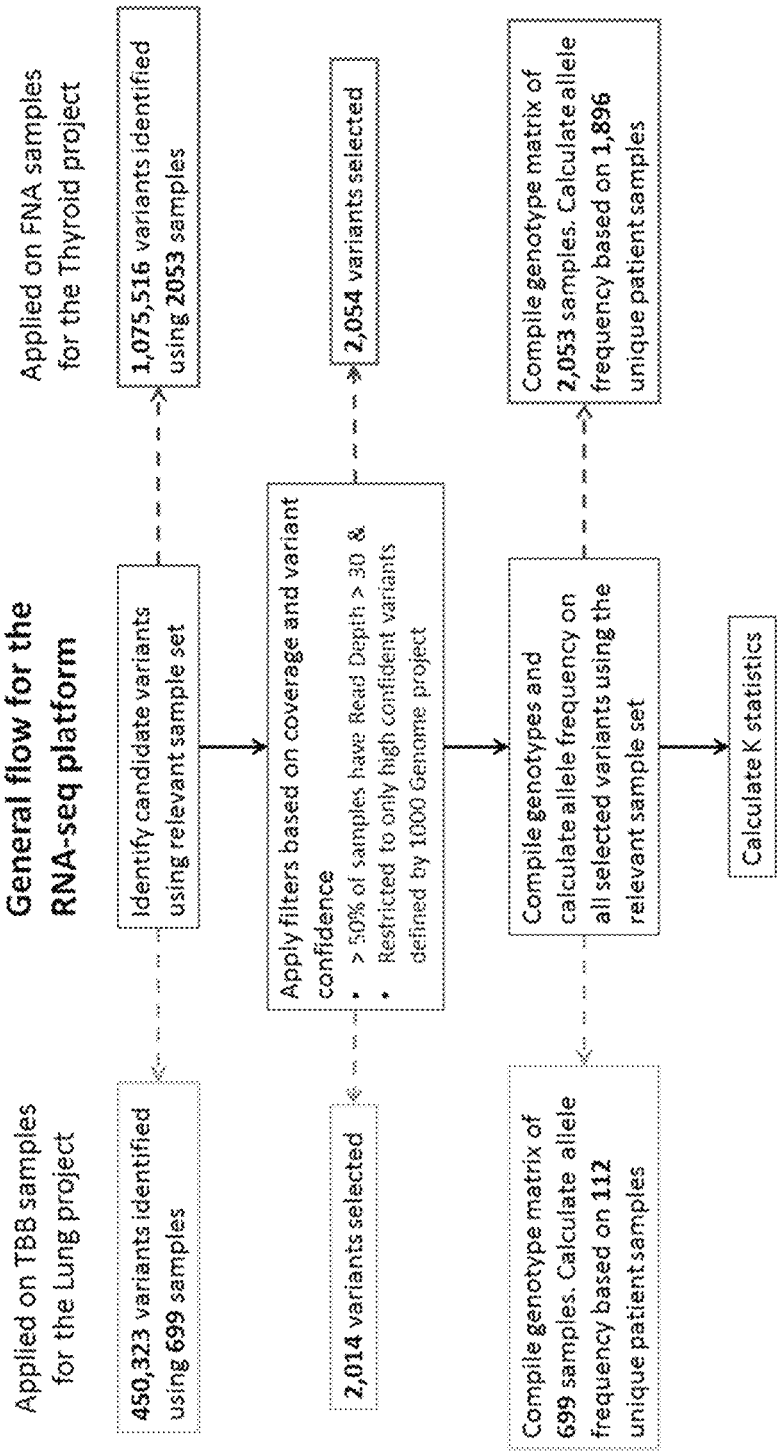
FIG. 1 shows a flow chart of variant selection.

While various embodiments of the invention have been shown and described herein, it will be obvious to those skilled in the art that such embodiments are provided by way of example only. Numerous variations, changes, and substitutions may occur to those skilled in the art without departing from the invention. It should be understood that various alternatives to the embodiments of the invention described herein may be employed.

The correct mapping of patient to sequencing file is important for, but not limited to, accurate patient diagnosis and assessment of diagnostic test accuracy. As such, several methods have been proposed to confirm the identity of samples. These methods have been primarily designed for deoxyribonucleic acid (DNA) sequencing data and/or require an orthogonal reference method, such as a single nucleotide polymorphism (SNP) microarray, which are not applicable where the samples are run on ribonucleic acid (RNA) sequencing platform and corresponding reference data may not be available. The disclosure provides novel methods for verifying sample identity and tracking samples in a clinical setting.

The disclosure provides methods for verifying sample identity by using genetic relatedness or kinship between two or more samples. Various methods can be used for determining kinship, such as by using pedigree information, linkage studies, and/or genome-wide genotype data. Such kinship methodologies can be used to determine sample integrity, for example, to determine whether one sample from an individual comes from the same individual as the other samples. The methods can be useful in determining whether or not there has been a sample mix-up. Molecular analysis of even a single biological sample can be a multistep process and can result in the generation of numerous sample intermediates. Sample mix-ups can occur at any step, ultimately causing analysis interpretation problems. While most laboratories implement procedures that minimize the risk of sample mix-ups, sometimes these mix-ups can occur. Samples can get mixed up during the sample gathering, transport, handling and/or analysis process, but it will appreciated that the same or similar methods may be used more generally, for example, to determine if a sample or samples in a group of samples is from the same individual. Disclosed herein are methods for evaluating a cohort of samples and determining whether a given sample was mixed-up with another.

In a microarray-enabled lab, sample mix-ups are generally discovered during unsupervised clustering analysis, which can be an early step in the data mining process meant to reveal the relative genetic distances between a cohort of samples. Any sample that clusters with another not belonging to the same patient suggests that a mix-up may have occurred. However, sometimes what may appear to be a sample-mix up, can actually be an analytical artifact. In a clinical setting, it can be critical to distinguish between these two scenarios for three reasons. First, it can be imperative to return correct results to inform clinical decisions. Second, from a population study perspective, samples suspected of mix-up can be dropped from final analyses, resulting in data loss and reduced statistical power. Third, from a discovery perspective, samples that initially present as a mix-up, but have not actually been mixed-up, can be rich in information that ought to be preserved, as its value in deciphering complex biology is unknown.

The methods can be useful to confirm technical replicates, for example, when multiple biological samples from the same individual are processed as unique samples for measuring the same analyte. The methods can be useful to confirm biological replicates, for example, when different biological analytes from the same individual are processed on multiple platforms. Querying the relatedness of genomic data of two samples can identify sample swaps prior to inappropriate inclusion in data analysis. All downstream inferences rely on correct mapping of genomic data with sample identity. Kinship coefficients can directly measure the mapping accuracy and ensure sample integrity.

Kinship coefficients can measure relatedness between two individuals and can have wide usage in genetic applications. Kinship coefficients can be used to directly facilitate sample tracking to identify potential sample swaps. Such sample integrity metrics can be important for the following two scenarios in large-scale clinical studies, for example. In a first example, multiple biological samples from the same individual may be routinely processed as unique samples or technical replicates. Querying the relatedness of genomic data of two samples can identify sample swaps prior to inappropriate inclusion in data analysis. In a second example, different biological analytes from the same samples may be run across multiple platforms and may be important to establish the correct mapping for each individual sample, linking genomic information derived from multiple platforms to the same sample. For both cases, all downstream inferences may rely on such correct mapping. Kinship coefficients can directly measure the mapping accuracy and ensure sample integrity.

Subjects

Disclosed herein are methods for determining sample integrity using kinship coefficients so that a sample from a given subject may be identified, e.g., for identifying and/or resolving sample mix-ups that can occur during collection, transport, processing, or analysis of a plurality of biological samples each obtained from a subject. The plurality of biological samples can contain two or more biological samples; for examples, about 2-1000, 2-500, 2-250, 2-100, 2-75, 2-50, 2-25, 2-10, 10-1000, 10-500, 10-250, 10-100, 10-75, 10-50, 10-25, 25-1000, 25-500, 25-250, 25-100, 25-75, 25-50, 50-1000, 50-500, 50-250, 50-100, 50-75, 60-70, 100-1000, 100-500, 100-250, 250-1000, 250-500, 500-1000, 2, 3, 4, 5, 6, 7, 8, 9, 10, 11, 12, 13, 14, 15, 16, 17, 18, 19, 20, 21, 22, 23, 24, 25, 30, 35, 40, 45, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 90, 95, 100, 110, 120, 130, 140, 150, 160, 170, 180, 190, 200, 210, 220, 230, 240, 250, 275, 300, 325, 350, 375, 400, 425, 450, 475, 500, 550, 600, 650, 700, 750, 800, 850, 900, 950, 1000, or more biological samples. Biological samples can be obtained from a plurality of subjects, giving a plurality of sets of a plurality of samples. Biological samples can be obtained from about 2 to about 1000 subjects, or more; for example, about 2-1000, 2-500, 2-250, 2-100, 2-50, 2-25, 2-20, 2-10, 10-1000, 10-500, 10-250, 10-100, 10-50, 10-25, 10-20, 15-20, 25-1000, 25-500, 25-250, 25-100, 25-50, 50-1000, 50-500, 50-250, 50-100, 100-1000, 100-500, 100-250, 250-1000, 250-500, 500-1000, or at least 2, 3, 4, 5, 6, 7, 8, 9, 10, 11, 12, 13, 14, 15, 16, 17, 18, 19, 20, 21, 22, 23, 24, 25, 30, 35, 40, 45, 50, 55, 60, 65, 68, 70, 75, 80, 85, 90, 95, 100, 110, 120, 130, 140, 150, 160, 170, 180, 190, 200, 210, 220, 230, 240, 250, 275, 300, 325, 350, 375, 400, 425, 450, 475, 500, 550, 600, 650, 700, 750, 800, 850, 900, 950, 1000, or more subjects. A plurality of biological samples can comprise replicate samples, biological or technical, of one subject or a plurality of subjects.

A subject can be any subject that produces RNA that can further be subjected to a sequencing assay, e.g., the subject may be a eukaryotic subject, such as a plant, an animal, and in some cases a mammal, e.g., human.

Biological samples can be obtained from human subjects. Biological samples can be obtained from human subjects at different ages. A human subject can be prenatal (e.g., a fetus), a child (e.g., a neonate, an infant, a toddler, a preadolescent), an adolescent, a pubescent, or an adult (e.g., an early adult, a middle aged adult, a senior citizen). A human subject can be between about 0 months and about 120 years old, or older. A human subject can be between about 0 and about 12 months old; for example, about 1, 2, 3, 4, 5, 6, 7, 8, 9, 10, 11, or 12 months old. A human subject can be between about 0 and 12 years old; for example, between about 0 and 30 days old; between about 1 month and 12 months old; between about 1 year and 3 years old; between about 4 years and 5 years old; between about 4 years and 12 years old; about 1, 2, 3, 4, 5, 6, 7, 8, 9, 10, 11, or 12 years old. A human subject can be between about 13 years and 19 years old; for example, about 13, 14, 15, 16, 17, 18, or 19 years old. The human subject can be between about 20 and about 39 year old; for example, about 20, 21, 22, 23, 24, 25, 26, 27, 28, 29, 30, 31, 32, 33, 34, 35, 36, 37, 38, or 39 years old. A human subject can be between about 40 to about 59 years old; for example, about 40, 41, 42, 43, 44, 45, 46, 47, 48, 49, 50, 51, 52, 53, 54, 55, 56, 57, 58, or 59 years old. A human subject can be greater than 59 years old; for example, about 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, or 120 years old. Human subjects can include living subjects or deceased subjects. Human subjects can include male subjects and/or female subjects.

Biological samples can be obtained from any suitable source that allows determination of RNA sequences for determining variants, e.g., from cells, tissues, bodily fluids or secretions, or a gene expression product derived therefrom (e.g., nucleic acids, such as DNA or RNA; polypeptides, such as protein or protein fragments). The nature of the biological sample can depend upon the nature of the subject. If a biological sample is from a subject that is a unicellular organism or a multicellular organism with undifferentiated tissue, the biological sample can comprise cells, such as a sample of a cell culture, an excision of the organism, or the entire organism. If a biological sample is from a multicellular organism, the biological sample can be a tissue sample, a fluid sample, or a secretion.

Biological samples can be obtained from different tissues. The term tissue is meant to include ensembles of cells that are of a common developmental origin and have similar or identical function. The term tissue is also meant to encompass organs, which can be a functional grouping and organization of cells that can have different origins. A biological sample can be obtained from any tissue. A biological sample can be a plant tissue, such as obtained from vegetative and/or reproductive organs. Vegetative organs can include leaves, stems, roots, for example. Reproductive organs can include flowers, seeds, cones, for example.

Biological samples can be obtained from different tissue samples from one or more humans or non-human animals. Suitable tissues can include connective tissues, muscle tissues, nervous tissues, epithelial tissues or a portion or combination thereof. Suitable tissues can also include all or a portion of a lung, a heart, a blood vessel (e.g., artery, vein, capillary), a salivary gland, a esophagus, a stomach, a liver, a gallbladder, a pancreas, a colon, a rectum, an anus, a hypothalamus, a pituitary gland, a pineal gland, a thyroid, a parathyroid, an adrenal gland, a kidney, a ureter, a bladder, a urethra, a lymph node, a tonsil, an adenoid, a thymus, a spleen, skin, muscle, a brain, a spinal cord, a nerve, an ovary, a fallopian tube, a uterus, vaginal tissue, a mammary gland, a testicle, a vas deferens, a seminal vesicle, a prostate, penile tissue, a pharynx, a larynx, a trachea, a bronchi, a diaphragm, bone marrow, a hair follicle, or a combination thereof. A biological sample from a human or non-human animal can also include a bodily fluid, secretion, or excretion; for example, a biological sample can be a sample of aqueous humour, vitreous humour, bile, blood, blood serum, breast milk, cerebrospinal fluid, endolymph, perilymph, female ejaculate, amniotic fluid, gastric juice, menses, mucus, peritoneal fluid, pleural fluid, saliva, sebum, semen, sweat, tears, vaginal secretion, vomit, urine, feces, or a combination thereof. A biological sample can be from healthy tissue, diseased tissue, tissue suspected of being diseased, or a combination thereof.

In some embodiments, a biological sample is a fluid sample, for example a sample of blood, serum, sputum, urine, semen, or other biological fluid. In certain embodiments, the sample is a blood sample. In some embodiments, the biological sample is a tissue sample, such as a tissue sample taken to determine the presence or absence of disease in the tissue. In certain embodiments, the sample is a sample of thyroid tissue.

Biological samples can be obtained from subjects in different stages of disease progression or different conditions. Different stages of disease progression or different conditions can include healthy, at the onset of primary symptom, at the onset of secondary symptom, at the onset of tertiary symptom, during the course of primary symptom, during the course of secondary symptom, during the course of tertiary symptom, at the end of the primary symptom, at the end of the secondary symptom, at the end of tertiary symptom, after the end of the primary symptom, after the end of the secondary symptom, after the end of the tertiary symptom, or a combination thereof. Different stages of disease progression can be a period of time after being diagnosed or suspected to have a disease; for example, at least about, or at least, 1, 2, 3, 4, 5, 6, 7, 8, 9, 10, 11, 12, 13, 14, 15, 16, 17, 18, 19, 20, 21, 22, 23 or 24 hours; 1, 2, 3, 4, 5, 6, 7, 8, 9, 10, 11, 12, 13, 14, 15, 16, 17, 18, 19, 20, 21, 22, 23, 24, 25, 26, 27 or 28 days; 1, 2, 3, 4, 5, 6, 7, 8, 9, 10, 11, 12, 13, 14, 15, 16, 17, 18, 19 or 20 weeks; 1, 2, 3, 4, 5, 6, 7, 8, 9, 10, 11 or 12 months; 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49 or 50 years after being diagnosed or suspected to have a disease. Different stages of disease progression or different conditions can include before, during or after an action or state; for example, treatment with drugs, treatment with a surgery, treatment with a procedure, performance of a standard of care procedure, resting, sleeping, eating, fasting, walking, running, performing a cognitive task, sexual activity, thinking, jumping, urinating, relaxing, being immobilized, being emotionally traumatized, being shock, and the like.

Obtaining Biological Samples

The methods of the present disclosure provide for analysis of a biological sample from a subject or a set of subjects. Subject(s) may be, e.g., any animal (e.g., a mammal), including but not limited to humans, non-human primates, rodents, dogs, cats, pigs, fish, and the like. The present methods and compositions can apply to biological samples from humans, as described herein.

The methods of obtaining provided herein include methods of biopsy including fine needle aspiration (FNA), core needle biopsy, vacuum assisted biopsy, incisional biopsy, excisional biopsy, punch biopsy, shave biopsy or skin biopsy. In some cases, the methods and compositions provided herein are applied to data only from biological samples obtained by FNA. In some cases, the methods and compositions provided herein are applied to data only from biological samples obtained by FNA or surgical biopsy. In some cases, the methods and compositions provided herein are applied to data only from biological samples obtained by surgical biopsy Biological samples can be obtained from any of the tissues provided herein; including, but not limited to, skin, heart, lung, kidney, breast, pancreas, liver, muscle, smooth muscle, bladder, gall bladder, colon, intestine, brain, prostate, esophagus, or thyroid. Alternatively, the sample can be obtained from any other source; including, but not limited to, blood, sweat, hair follicle, buccal tissue, tears, menses, feces, or saliva. A biological sample can be obtained by a medical professional. The medical professional can refer the subject to a testing center or laboratory for submission of the biological sample. A subject can directly provide the biological sample. In some cases, a molecular profiling business can obtain the sample. In some cases, the molecular profiling business obtains data regarding the biological sample, such as biomarker expression level data, or analysis of such data.

A biological sample can be obtained by various methods such as the biopsy methods provided herein, swabbing, scraping, phlebotomy, or any other suitable method. The biological sample can be obtained, stored, or transported using components of a kit of the present disclosure. In some cases, multiple biological samples, such as multiple thyroid samples, can be obtained for analysis, characterization, or diagnosis according to the methods of the present disclosure. In some cases, multiple biological samples, such as one or more samples from one tissue type (e.g., thyroid) and one or more samples from another tissue type (e.g., buccal) can be obtained for diagnosis or characterization by the methods of the present disclosure. In some cases, multiple samples, such as one or more samples from one tissue type (e.g., thyroid) and one or more samples from another tissue (e.g., buccal) can be obtained at the same or different times. In some cases, the samples obtained at different times are stored and/or analyzed by different methods. For example, a sample can be obtained and analyzed by cytological analysis (e.g., using routine staining). In some cases, a further sample can be obtained from a subject based on the results of a cytological analysis. The diagnosis of cancer or other condition can include an examination of a subject by a physician, nurse or other medical professional. The examination can be part of a routine examination, or the examination can be due to a specific complaint including, but not limited to, one of the following: pain, illness, anticipation of illness, presence of a suspicious lump or mass, a disease, or a condition. The subject may or may not be aware of the disease or condition. The medical professional can obtain a biological sample for testing. In some cases the medical professional can refer the subject to a testing center or laboratory for submission of the biological sample.

In some cases, a subject can be referred to a specialist such as an oncologist, surgeon, or endocrinologist for further diagnosis. The specialist can likewise obtain a biological sample for testing or refer the individual to a testing center or laboratory for submission of the biological sample. In any case, the biological sample can be obtained by a physician, nurse, or other medical professional such as a medical technician, endocrinologist, cytologist, phlebotomist, radiologist, or a pulmonologist. The medical professional can indicate the appropriate test or assay to perform on the sample, or the molecular profiling business of the present disclosure can consult on which assays or tests are most appropriately indicated. The molecular profiling business can bill the individual or medical or insurance provider thereof for consulting work, for sample acquisition and/or storage, for materials, or for all products and services rendered.

A medical professional need not be involved in the initial diagnosis or sample acquisition. An individual can alternatively obtain a sample through the use of an over the counter kit. The kit can contain an instrument for obtaining said sample as described herein, an instrument for storing the sample for inspection, and instructions for proper use of the kit. In some cases, molecular profiling services are included in the price for purchase of the kit. In other cases, the molecular profiling services are billed separately.

A biological sample suitable for use by the molecular profiling business can be any material containing tissues, cells, nucleic acids, genes, gene fragments, expression products, gene expression products, and/or gene expression product fragments of an individual to be tested. Methods for determining sample suitability and/or adequacy are provided. A biological sample can include, but is not limited to, tissue, cells, and/or biological material from cells or derived from cells of an individual. A sample can be a heterogeneous or homogeneous population of cells or tissues. The biological sample can be obtained using any method that can provide a sample suitable for the analytical methods described herein.

A biological sample can be obtained by non-invasive methods, such methods including, but not limited to: scraping of the skin or cervix, swabbing of the cheek, saliva collection, urine collection, feces collection, collection of menses, tears, or semen. The biological sample can be obtained by an invasive procedure, such procedures including, but not limited to: biopsy, alveolar or pulmonary lavage, needle aspiration, or phlebotomy. The method of biopsy can further include incisional biopsy, excisional biopsy, punch biopsy, shave biopsy, or skin biopsy. The method of needle aspiration can further include fine needle aspiration (FNA), core needle biopsy, vacuum assisted biopsy, or large core biopsy.

Multiple biological samples can be obtained by the methods herein to ensure a sufficient amount of biological material. Methods of obtaining suitable samples of thyroid are further described in the ATA Guidelines for thyroid nodule management (Cooper et al. Thyroid Vol. 16 No. 2 2006), herein incorporated by reference in its entirety. Methods for obtaining biological samples are further described in for example Ramzy, Ibrahim Clinical Cytopathology and Aspiration Biopsy 2001 which is herein incorporated by reference in its entirety. A biological sample can be a fine needle aspirate of a thyroid nodule or a suspected thyroid tumor. Fine needle aspiration sampling procedure can be guided by the use of an ultrasound, X-ray, or other imaging device.

A molecular profiling business can obtain a biological sample directly, from a medical professional, from a third party, and/or from a kit provided by the molecular profiling business or a third party. A biological sample can be obtained by the molecular profiling business after the subject, the medical professional, or the third party acquires and sends the biological sample to the molecular profiling business. The molecular profiling business can provide suitable containers and/or excipients for storage and transport of the biological sample to the molecular profiling business.

Obtaining a Biological Sample can be Aided by the Use of a Kit

A kit can be provided containing materials for obtaining, storing, and/or shipping biological samples. A kit can contain, for example, materials and/or instruments for the collection of the biological sample (e.g., sterile swabs, sterile cotton, disinfectant, needles, syringes, scalpels, anesthetic swabs, knives, curette blade, liquid nitrogen, etc.). A kit can contain, for example, materials and/or instruments for the storage and/or preservation of biological samples (e.g., containers; materials for temperature control such as ice, ice packs, cold packs, dry ice, liquid nitrogen; chemical preservatives or buffers such as formaldehyde, formalin, paraformaldehyde, glutaraldehyde, alcohols such as ethanol or methanol, acetone, acetic acid, HOPE fixative (Hepes-glutamic acid buffer-mediated organic solvent protection effect), heparin, saline, phosphate buffered saline, TAPS, bicine, Tris, tricine, TAPSO, HEPES, TES, MOPS, PIPES, cadodylate, SSC, MES, phosphate buffer; protease inhibitors such as aprotinin, bestatin, calpain inhibitor I and II, chymostatin, E-64, leupeptin, alpha-2-macroglobulin, pefabloc SC, pepstatin, phenylmethanesufonyl fluoride, trypsin inhibitors; DNAse inhibitors such as 2-mercaptoethanol, 2-nitro-5-thicyanobenzoic acid, calcium, EGTA, EDTA, sodium dodecyl sulfate, iodoacetate, etc.; RNAse inhibitors such as ribonuclease inhibitor protein; double-distilled water; DEPC (diethyprocarbonate) treated water, etc.). A kit can contain instructions for use. A kit can be provided as, or contain, a suitable container for shipping. The shipping container can be an insulated container. The shipping container can be self-addressed to a collection agent (e.g., laboratory, medical center, genetic testing company, etc.). A kit can be provided to a subject for home use or use by a medical professional. Alternatively, a kit can be provided directly to a medical professional.

One or more biological samples can be obtained from a given subject. In some cases, between about 1 and about 50 biological samples can be obtained from the given subject; for example, about 1-50, 1-40, 1-30, 1-25, 1-20, 1-15, 1-10, 1-7, 1-5, 5-50, 5-40, 5-30, 5-25, 5-15, 5-10, 10-50, 10-40, 10-25, 10-20, 25-50, 25-40, or at least 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50 biological samples can be obtained from the given subject. Multiple biological samples from a given subject can be obtained from the same source (e.g., the same tissue), e.g., multiple blood samples, or multiple tissue samples, or from multiple sources (e.g., multiple tissues). Multiple biological samples from a given subject can be obtained at the same time or at different times. Multiple biological samples from a given subject can be obtained when the subject is experiencing a same (e.g., repeated or stagnant) condition or different condition. Multiple biological samples from a given subject can be obtained at the same disease progression or different disease progression of the subject. If multiple biological samples are collected from the same source (e.g., the same tissue) from the particular subject, the samples can optionally be combined into a single sample. Combining samples in this way can ensure that enough material is obtained for testing and/or analysis.

Transport of Biological Samples

In some cases, the methods of the present disclosure provide for transport of a biological sample. In some cases, a biological sample is transported from a clinic, hospital, doctor's office, or other location to a second location whereupon the sample can be stored and/or analyzed by, for example, cytological analysis or molecular profiling. Biological samples can be transported to a molecular profiling company in order to perform the analyses described herein. In other cases, a biological sample can be transported to a laboratory, such as a laboratory authorized or otherwise capable of performing the methods of the present disclosure, such as a Clinical Laboratory Improvement Amendments (CLIA) laboratory. A biological sample can be transported by the subject from whom the biological sample derives. The transportation by the subject can include the subject appearing at a molecular profiling business or a designated sample receiving point and providing the biological sample. The providing of a biological sample can involve any of the techniques of sample acquisition described herein, or the biological sample can have already have been acquired and stored in a suitable container as described herein. A biological sample can be transported to a molecular profiling business using a courier service, the postal service, a shipping service, or any method capable of transporting the biological sample in a suitable manner. A biological sample can be provided to the molecular profiling business by a third party testing laboratory (e.g., a cytology lab). In other cases, a biological sample can be provided to the molecular profiling business by the subject's primary care physician, endocrinologist or other medical professional. The cost of transport can be billed to the subject, medical provider, or insurance provider. The molecular profiling business can begin analysis of the sample immediately upon receipt, or can store the sample in any manner described herein. The method of storage can optionally be the same as chosen prior to receipt of the sample by the molecular profiling business.

A biological sample can be transported in any medium or excipient, including any medium or excipient provided herein suitable for storing the biological sample such as a cryopreservation medium or a liquid based cytology preparation. A biological sample can be transported frozen or refrigerated, such as at any of the suitable sample storage temperatures provided herein.

Upon receipt of a biological sample by a molecular profiling business, a representative or licensee thereof, a medical professional, researcher, or a third party laboratory or testing center (e.g., a cytology laboratory), a biological sample can be assayed using a variety of analyses, such as cytological assays and genomic analysis. Such assays or tests can be indicative of cancer, a type of cancer, any other disease or condition, the presence of disease markers, the presence of genetic mutations, or the absence of cancer, diseases, conditions, or disease markers. Assays or tests can take the form of cytological examination including microscopic examination. Assays or tests can involve the use of one or more cytological stains. A biological sample can be manipulated or prepared for the test prior to administration of the test by any suitable method for biological sample preparation. Which assay to perform can be determined by the molecular profiling business, the physician who ordered the test, or a third party such as a consulting medical professional, cytology laboratory, the subject from whom the sample derives, and/or an insurance provider. An assay can be chosen based on the likelihood of obtaining a definite diagnosis, the cost of the assay, the speed of the assay, or the suitability of the assay to the type of material provided.

Storage of Biological Samples

Biological samples can be stored for a period of time prior to processing or analysis of the biological samples. The period of time biological samples can be stored can be measured in seconds, minutes, hours, days, weeks, months, years or longer. Biological samples can be subdivided. Subdivided biological samples can be stored, processed, or a combination thereof. Subdivided biological samples can be subject to different downstream processes (e.g., storage, cytological analysis, adequacy tests, nucleic acid extraction, molecular profiling and/or a combination thereof).

A portion of a biological sample can be stored while another portion of the biological sample is further manipulated. Such manipulations can include, but are not limited to, molecular profiling; cytological staining; nucleic acid (RNA and/or DNA) extraction, detection, or quantification; gene expression product (e.g., RNA or protein) extraction, detection, or quantification; fixation (e.g., formalin fixed paraffin embedded samples); and/or examination. A biological sample can be fixed prior to or during storage by any suitable method, such methods including, but not limited to, the use of glutaraldehyde, formaldehyde, and/or methanol. In other cases, a sample is obtained and stored and subdivided after the step of storage for further analysis such that different portions of the sample are subject to different downstream methods or processes including but not limited to storage, cytological analysis, adequacy tests, nucleic acid extraction, molecular profiling or a combination thereof. In some cases, one or more biological samples are obtained and analyzed by cytological analysis, and the resulting sample material is further analyzed by one or more molecular profiling methods of the present disclosure. In such cases, biological samples can be stored between the steps of cytological analysis and the steps of molecular profiling. Biological samples can be stored upon acquisition; for example, to facilitate transport or to wait for the results of other analyses. Biological samples can be stored while awaiting instructions from a physician or other medical professional.

A biological sample can be placed in a suitable medium, excipient, solution, and/or container for short term or long term storage. Storage can involve keeping the biological sample in a refrigerated or frozen environment. A biological sample can be quickly frozen prior to storage in a frozen environment. A biological sample can be contacted with a suitable cryopreservation medium or compound prior to, during, and/or after cooling or freezing the biological sample. A cryopreservation medium or compound can include, but is not limited to: glycerol, ethylene glycol, sucrose, and/or glucose. A suitable medium, excipient, or solution can include, but is not limited to: hanks salt solution; saline; cellular growth medium; an ammonium salt solution, such as ammonium sulphate or ammonium phosphate; and/or water. Suitable concentrations of ammonium salts can include solutions of between about 0.1 g/mL to 2.5 g/L, or higher; for example, about 0.1 g/ml, 0.2 g/ml, 0.3 g/ml, 0.4 g/ml, 0.5 g/ml, 0.6 g/ml, 0.7 g/ml, 0.8 g/ml, 0.9 g/ml, 1.0 g/ml, 1.1 g/ml, 1.2 g/ml, 1.3 g/ml, 1.4 g/ml, 1.5 g/ml, 1.6 g/ml, 1.7 g/ml, 1.8 g/ml, 1.9 g/ml, 2.0 g/ml, 2.2 g/ml, 2.3 g/ml, 2.5 g/ml or higher. The medium, excipient, or solution can optionally be sterile.

A biological sample can be stored at room temperature; at reduced temperatures, such as cold temperatures (e.g., between about 20° C. and about 0° C.); and/or freezing temperatures, including for example about 0° C., −1° C., −2° C., −3° C., −4° C., −5° C., −6° C., −7° C., −8° C., −9° C., −10° C., −12° C., −14° C., −15° C., −16° C., −20° C., −22° C., −25° C., −28° C., −30° C., −35° C., −40° C., −45° C., −50° C., −60° C., −70° C., −80° C., −100° C., −120° C., −140° C., −180° C., −190° C., or −200° C. A biological sample can be stored in a refrigerator, on ice or a frozen gel pack, in a freezer, in a cryogenic freezer, on dry ice, in liquid nitrogen, and/or in a vapor phase equilibrated with liquid nitrogen.

A medium, excipient, or solution for storing a biological sample can contain preservative agents to maintain the sample in an adequate state for subsequent diagnostics or manipulation, or to prevent coagulation. The preservatives can include, but are not limited to, citrate, ethylene diamine tetraacetic acid, sodium azide, and/or thimersol. The medium, excipient or solution can contain suitable buffers or salts such as Tris buffers, phosphate buffers, sodium salts (e.g., NaCl), calcium salts, magnesium salts, and the like. In some cases, a biological sample can be stored in a commercial preparation suitable for storage of cells for subsequent cytological analysis, such preparations including, but not limited to Cytyc ThinPrep, SurePath, and/or Monoprep.

A sample container can be any container suitable for storage and/or transport of a biological sample; such containers including, but not limited to: a cup, a cup with a lid, a tube, a sterile tube, a vacuum tube, a syringe, a bottle, a microscope slide, or any other suitable container. The container can optionally be sterile.

Test for Adequacy of Biological Samples

Subsequent to or during biological sample acquisition, including before or after a step of storing the sample, the biological material can be assessed for adequacy, for example, to assess the suitability of the sample for use in the methods and compositions of the present disclosure. The assessment can be performed by an individual who obtains the sample; a molecular profiling business; an individual using a kit; or a third party, such as a cytological lab, pathologist, endocrinologist, or a researcher. A biological sample can be determined to be adequate or inadequate for further analysis due to many factors, such factors including, but not limited to: insufficient cells; insufficient genetic material; insufficient protein, DNA, or RNA; inappropriate cells for the indicated test; inappropriate material for the indicated test; age of the sample; manner in which the sample was obtained; and/or manner in which the sample was stored or transported. Adequacy can be determined using a variety of methods such as a cell staining procedure, measurement of the number of cells or amount of tissue, measurement of total protein, measurement of nucleic acid levels, visual examination, microscopic examination, or temperature or pH determination. Sample adequacy can be determined from a result of performing a gene expression product level analysis experiment. Sample adequacy can be determined by measuring the content of a marker of sample adequacy. Such markers can include elements such as iodine, calcium, magnesium, phosphorous, carbon, nitrogen, sulfur, iron etc.; proteins such as, but not limited to, thyroglobulin; cellular mass; and cellular components such as proteins, nucleic acids, lipids, or carbohydrate.

Cell and/or Tissue Content Adequacy Test

Methods for determining the amount of a tissue in a biological sample can include, but are not limited to, weighing the sample or measuring the volume of sample. Methods for determining the amount of cells in the biological sample can include, but are not limited to, counting cells, which can in some cases be performed after dis-aggregation of the biological sample (e.g., with an enzyme such as trypsin or collagenase or by physically, such as using a tissue homogenizer). Alternative methods for determining the amount of cells in the biological sample can include, but are not limited to, quantification of dyes that bind to cellular material or measurement of the volume of cell pellet obtained following centrifugation. Methods for determining that an adequate number of a specific type of cell is present in the biological sample can also include PCR, Q-PCR, RT-PCR, immunohistochemical analysis, cytological analysis, microscopic, and/or visual analysis.

Nucleic Acid Content Adequacy Test

Biological samples can be tested for adequacy; for example, by analysis of nucleic acid content after extraction from the biological sample using a variety of methods. Nucleic acids, such as RNA or messenger ribonucleic acid molecules (mRNA), can be extracted from other nucleic acids prior to nucleic acid content analysis. In some cases, mRNA can be purified from the biological sample using one or more purification protocols, such as LiCl precipitation protocol, phenol-chloroform extraction followed by ethanol precipitation, column purification, and/or gel purification. In some cases, specific mRNAs can be enriched by nucleic acid amplification procedures. For example, mRNAs can be enriched by using a probe set with a plurality of probes that specifically can bind to the mRNAs or transcripts to enrich for those mRNAs or transcripts. Probe set may have target-specific sequences. Probe set may not have target-specific sequences, such as probes with oligo-dT sequences. In some cases, probes may comprise ribonucleic acid, synthetic nucleotides or a combination thereof.

Nucleic acid content can be extracted, purified, and measured by ultraviolet absorbance, including but not limited to absorbance at 260 nanometers using a spectrophotometer. Nucleic acid content or adequacy can be measured by fluorometer after contacting the sample with a stain. Nucleic acid content or adequacy can be measured after electrophoresis, or using an instrument such as an Agilent bioanalyzer.

It can be useful to measure the quantity or yield of nucleic acids (e.g., DNA, RNA, etc.). The yield of nucleic acids can be measured immediately after extracting the nucleic acids from the biological sample. The yield of nucleic acids can also be measured after storing the extracted nucleic acids for a period of time. The yield of nucleic acids can be measured following an experimental manipulation or transformation of the extracted nucleic acids. For example, RNA can be extracted and/or purified from a biological sample and subjected to reverse transcriptase PCR after which the cDNA levels can be measured to determine adequacy. If a specific type of nucleic acid is desired (e.g., DNA, RNA, mRNA, etc.), the quantity of yield of the specific type of nucleic acid can be measured after purification. The quantity or yield of nucleic acids can be measured using spectrophotometry. The quantity or yield of nucleic acids (e.g., DNA and/or RNA) from a biological sample can be measured shortly after purification, for example, using a NanoDrop spectrophotometer in a range of nano- to micrograms. The NanoDrop is a cuvette-free spectrophotometer. It can use 1 µL to measure from about 5 ng/µL to about 3,000 ng/µL of sample. Features of the NanoDrop include low volume of sample and no cuvette; large dynamic range 5 ng/4 to 3,000 ng/µL; and it allows quantitation of DNA, RNA and proteins. NanoDrop™ 2000c allows for the analysis of 0.5 µL-2.0 µL samples, without the need for cuvettes or capillaries. The NanoDrop is presented as an example of an instrument to measure nucleic acid quantities or yields; however, other instruments or methods can be used in the methods disclosed herein.

A threshold yield of nucleic acids can be required during adequacy testing of biological samples. The threshold yield of nucleic acids can be between about 1 ng to about 100 µg or more; for example, the threshold yield can be about 1 ng-100 µg, 1 ng-10 µg, 1 ng-5 µg, 1 ng-1 µg, 1 ng-500 ng, 1 ng-250 ng, 1 ng-50 ng, 1 ng-10 ng, 10 ng-100 µg, 10 ng-10 µg, 10 ng-5 µg, 10 ng-1 µg, 10 ng-500 ng, 10 ng-250 ng, 10 ng-50 ng, 50 ng-100 µg, 50 ng-10 µg, 50 ng-5 µg, 50 ng-1 µg, 50 ng-500 ng, 50 ng-250 ng, 250 ng-100 µg, 250 ng-10 µg, 250 ng-5 µg, 250 ng-1 µg, 250 ng-500 ng, 500 ng-100 µg, 500 ng-10 µg, 500 ng-5 µg, 500 ng-1 µg, 1 µg-100 µg, 1 µg-10 µg, 1 µg-5 µg, 5 µg-100 µg, 5 µg-10 µg, 10 µg-100 µg, or any intervening range. The threshold yield of a nucleic acid (e.g., DNA and/or RNA) for an adequate biological can be about 1 ng, 2 ng, 3 ng, 4 ng, 5 ng, 6 ng, 7 ng, 8 ng, 9 ng, 10 ng, 15 ng, 20 ng, 25 ng, 30 ng, 35 ng, 40 ng, 45 ng, 50 ng, 60 ng, 70 ng, 80 ng, 90 ng, 100 ng, 125 ng, 150 ng, 175 ng, 200 ng, 225 ng, 250 ng, 300 ng, 350 ng, 400 ng, 450 ng, 500 ng, 600 ng, 700 ng, 800 ng, 900 ng, 1 µg, 1.5 µg, 2 µg, 2.5 µg, 3 µg, 3.5 µg, 4 µg, 4.5 µg, 5 µg, 6 µg, 7 µg, 8 µg, 9 µg, 10 µg, 15 µg, 20 µg, 25 µg, 30 µg, 35 µg, 40 µg, 45 µg, 50 µg, 60 µg, 70 µg, 80 µg, 90 µg, 100 µg, or any intervening amount, or more. The threshold yield of nucleic acids for adequacy testing of biological samples can vary depending upon the intended method of analysis (e.g., microarray, southern blot, northern blot, sequencing, RT-PCR, serial analysis of gene expression (SAGE), etc.).

It can be useful to measure RNA quality when testing a biological sample for adequacy. RNA quality in a biological sample can be measured by a calculated RNA Integrity Number (RIN). RNA quality can be measured using an Agilent 2100 Bioanalyzer instrument, wherein quality is characterized by a calculated RNA Integrity Number (RIN, 1-10). The RNA integrity number (RIN) is an algorithm for assigning integrity values to RNA measurements. The integrity of RNA can be a major concern for gene expression studies and traditionally has been evaluated using the 28S to 18S rRNA ratio, a method that can be inconsistent. The RIN algorithm is applied to electrophoretic RNA measurements and based on a combination of different features that contribute information about the RNA integrity to provide a more robust universal measure. RNA quality can be measured using an Agilent 2100 Bioanalyzer instrument. Protocols for measuring RNA quality are available commercially, for example, at Agilent website. Briefly, in the first step, researchers deposit total RNA sample into an RNA Nano LabChip. In the second step, the LabChip is inserted into the Agilent bioanalyzer and the analysis is run, generating a digital electropherogram. In the third step, the RIN algorithm then analyzes the entire electrophoretic trace of the RNA sample, including the presence or absence of degradation products, to determine sample integrity. Then, the algorithm assigns a 1 to 10 RIN score, where level 10 RNA is completely intact. Because interpretation of the electropherogram is automatic and not subject to individual interpretation, universal and unbiased comparison of samples can be enabled and repeatability of experiments can be improved. The RIN algorithm was developed using neural networks and adaptive learning in conjunction with a large database of eukaryote total RNA samples, which were obtained mainly from human, rat, and mouse tissues. Advantages of RIN can include obtaining a numerical assessment of the integrity of RNA; directly comparing RNA samples (e.g., before and after archival, between different labs); and ensuring repeatability of experiments (e.g., if RIN shows a given value and is suitable for microarray experiments, then the RIN of the same value can always be used for similar experiments given that the same organism/tissue/extraction method is used (Schroeder A, et al. BMC Molecular Biology 2006, 7:3 (2006)), which is hereby incorporated by reference in its entirety).

The quality of RNA derived, purified, or extracted from a biological sample can be measured on a scale of RIN 1 to 10, with 10 being the highest quality. A biological sample can be determined to be inadequate if the RNA quality is measured to be below a threshold value; for example, the threshold value can be an RIN of about 1, 2, 3, 4, 5, 6, 7, 8, 9, or 10. In some cases, a threshold level of RNA quality is not used in determining the adequacy of a biological sample.

Assaying gene expression in a biological sample can be a complex, dynamic, and expensive process. RNA samples with RIN≤5.0 are typically not used for multi-gene microarray analysis, and can be limited to single-gene RT-PCR and/or TaqMan™ assays. This dichotomy in the usefulness of RNA according to quality can limit the usefulness of samples and hamper research and/or diagnostic efforts. The present disclosure provides methods via which low quality RNA can be used to obtain meaningful multi-gene expression results from samples containing low concentrations of RNA.

In addition, samples having a low and/or un-measurable RNA concentration by NanoDrop normally deemed inadequate for multi-gene expression analysis, can be measured and analyzed using the subject methods and algorithms of the present disclosure. A sensitive apparatus that can be used to measure nucleic acid yield is the NanoDrop spectrophotometer. Like many quantitative instruments of its kind, the accuracy of a NanoDrop measurement can decrease significantly with very low RNA concentration. The minimum amount of RNA necessary for input into a microarray experiment also limits the usefulness of a given sample. In the present disclosure, a sample containing a very low amount of nucleic acid can be estimated using a combination of the measurements from both the NanoDrop and the Bioanalyzer instruments, thereby optimizing the sample for multi-gene expression assays and analysis.

Gene Expression Products

Gene expression experiments may involve the measurement of the activity (or the expression) of a plurality of genes, to create a picture of cellular function. Gene expression data can be used, for example, to distinguish between cells that are actively dividing, or to show how the cells react to a particular treatment. Gene expression experiments may involve amplification of the nucleic acid molecules such as by performing microarray, serial analysis of gene expression (SAGE), reverse transcription polymerase chain reaction (PCR), or quantitative PCR. Nucleic acid molecules, such as RNA, may be amplified by using a probe set with a plurality of probes that specifically can bind to the mRNAs or transcripts. Probe set may have target-specific sequences. Probe set may not have target-specific sequences, such as probes with oligo-dT sequences. In some cases, probes may comprise ribonucleic acid, synthetic nucleotides or a combination thereof. Microarray technology can be used to measure the relative activity of previously identified target genes and other expressed sequences. Sequence based techniques, like serial analysis of gene expression (SAGE, SuperSAGE) are also used for assaying, measuring or obtaining gene expression data. SuperSAGE can measure any active gene, not just a predefined set. In an RNA, mRNA or gene expression profiling microarray, expression levels of thousands of genes can be simultaneously monitored to study the effects of certain treatments, diseases, and developmental stages on gene expression.

Gene expression experiments may involve measuring the relative amount of gene expression products, such as mRNA, expressed in two or more experimental conditions. This is because altered levels of a specific sequence of a gene expression product can suggest a changed need for the protein coded for by the gene expression product, potentially indicating a homeostatic response or a pathological condition.

In some embodiments, the method involves measuring, assaying or obtaining the expression levels of one or more genes. In some cases, the method provides a number, or a range of numbers, of genes that the expression levels of the genes can be used to diagnose, characterize or categorize a biological sample. The number of genes used can be between about 1 and about 500; for example about 1-500, 1-400, 1-300, 1-200, 1-100, 1-50, 1-25, 1-10, 10-500, 10-400, 10-300, 10-200, 10-100, 10-50, 10-25, 25-500, 25-400, 25-300, 25-200, 25-100, 25-50, 50-500, 50-400, 50-300, 50-200, 50-100, 100-500, 100-400, 100-300, 100-200, 200-500, 200-400, 200-300, 300-500, 300-400, 400-500, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 55, 60, 65, 70, 75, 80, 85, 90, 95, 100, 110, 120, 130, 140, 150, 160, 170, 180, 190, 200, 210, 220, 230, 240, 250, 260, 270, 280, 290, 300, 310, 320, 330, 340, 350, 360, 370, 380, 390, 400, 410, 420, 430, 440, 450, 460, 470, 480, 490, 500, or any included range or integer. For example, at least about 1, 2, 3, 4, 5, 6, 7, 8, 9, 10, 15, 20, 25, 30, 33, 35, 38, 40, 43, 45, 48, 50, 53, 58, 63, 65, 68, 100, 120, 140, 142, 145, 147, 150, 152, 157, 160, 162, 167, 175, 180, 185, 190, 195, 200, 300, 400, 500 or more total genes can be used. The number of genes used can be less than or equal to about 1, 2, 3, 4, 5, 6, 7, 8, 9, 10, 15, 20, 25, 30, 33, 35, 38, 40, 43, 45, 48, 50, 53, 58, 63, 65, 68, 100, 120, 140, 142, 145, 147, 150, 152, 157, 160, 162, 167, 175, 180, 185, 190, 195, 200, 300, 400, 500, or more.

Gene expression data may correspond to data of an expression level of one or more biomarkers that are related to a disease or condition. A disease or condition can be cancer; for example, thyroid cancer. Thyroid cancer can include any type of thyroid cancer, including but not limited to, any malignancy of the thyroid gland, e.g., papillary thyroid cancer, follicular thyroid cancer, medullary thyroid cancer and/or anaplastic thyroid cancer. In some cases, the disease or condition is one or more of the following types of thyroid cancer: papillary thyroid carcinoma (PTC), follicular variant of papillary thyroid carcinoma (FVPTC), follicular carcinoma (FC), Hurthle cell carcinoma (HC) or medullary thyroid carcinoma (MTC). In some instances, gene expression data may correspond to data of an expression level of one or more biomarkers that are related to one or more types of cancer; for example, adrenal cortical cancer, anal cancer, aplastic anemia, bile duct cancer, bladder cancer, bone cancer, bone metastasis, central nervous system (CNS) cancers, peripheral nervous system (PNS) cancers, breast cancer, Castleman's disease, cervical cancer, childhood Non-Hodgkin's lymphoma, lymphoma, colon and rectum cancer, endometrial cancer, esophagus cancer, Ewing's family of tumors (e.g. Ewing's sarcoma), eye cancer, gallbladder cancer, gastrointestinal carcinoid tumors, gastrointestinal stromal tumors, gestational trophoblastic disease, hairy cell leukemia, Hodgkin's disease, Kaposi's sarcoma, kidney cancer, laryngeal and hypopharyngeal cancer, acute lymphocytic leukemia, acute myeloid leukemia, children's leukemia, chronic lymphocytic leukemia, chronic myeloid leukemia, liver cancer, lung cancer, lung carcinoid tumors, Non-Hodgkin's lymphoma, male breast cancer, malignant mesothelioma, multiple myeloma, myelodysplastic syndrome, myeloproliferative disorders, nasal cavity and paranasal cancer, nasopharyngeal cancer, neuroblastoma, oral cavity and oropharyngeal cancer, osteosarcoma, ovarian cancer, pancreatic cancer, penile cancer, pituitary tumor, prostate cancer, retinoblastoma, rhabdomyosarcoma, salivary gland cancer, sarcoma (adult soft tissue cancer), melanoma skin cancer, non-melanoma skin cancer, stomach cancer, testicular cancer, thymus cancer, uterine cancer (e.g. uterine sarcoma), vaginal cancer, vulvar cancer, and Waldenstrom's macroglobulinemia.

Measuring Expression Levels of Gene Expression Products

Relative gene expression, as compared to normal cells and/or tissues of the same organ, can be determined by measuring the relative rates of transcription of RNA, such as by production of corresponding cDNAs and then analyzing the resulting DNA using probes developed from the gene sequences as corresponding to a genetic marker. Thus, the levels of cDNA produced by use of reverse transcriptase with the full RNA complement of a cell suspected of being cancerous produces a corresponding amount of cDNA that can then be amplified using polymerase chain reaction, or other methods, such as linear amplification, isothermal amplification, NASB, or rolling circle amplification, to determine the relative levels of resulting cDNA and, thereby, the relative levels of gene expression. Methods for determining gene expression product levels may include but are not limited to one or more of the following: additional cytological assays, assays for specific proteins or enzyme activities, assays for specific expression products including protein or RNA or specific RNA splice variants, in situ hybridization, whole or partial genome expression analysis, microarray hybridization assays, SAGE, enzyme linked immuno-absorbance assays, mass-spectrometry, immunohistochemistry, blotting, microarray, RT-PCR, quantitative PCR, sequencing, RNA sequencing, DNA sequencing (e.g., sequencing of cDNA obtained from RNA); Next-Gen sequencing, nanopore sequencing, pyrosequencing, or Nanostring sequencing.

Gene expression product levels may be normalized to an internal standard such as total mRNA or the expression level of a particular gene including but not limited to glyceraldehyde 3 phosphate dehydrogenase, or tublin.

In accordance with the foregoing, an expression level of a gene, genes, markers, gene expression products, mRNA, miRNAs, or a combination thereof as disclosed herein may be determined using northern blotting and employing the sequences as identified herein to develop probes for this purpose. Such probes may be composed of DNA or RNA or synthetic nucleotides or a combination of these and may advantageously be comprised of a contiguous stretch of nucleotide residues matching, or complementary to, a sequence corresponding to a genetic marker. Such probes will most usefully comprise a contiguous stretch of at least 15-200 residues or more including 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 80, 85, 90, 95, 100, 110, 120, 130, 140, 150, 160, 175, or 200 nucleotides or more. Thus, where a single probe binds multiple times to the transcriptome of experimental cells, whereas binding of the same probe to a similar amount of transcriptome derived from the genome of control cells of the same organ or tissue results in observably more or less binding, this is indicative of differential expression of a gene, multiple genes, markers, or miRNAs comprising, or corresponding to, the sequences corresponding to a genetic marker from which the probe sequence was derived.

In some instances, gene expression may be determined by microarray analysis using, for example, Affymetrix arrays, cDNA microarrays, oligonucleotide microarrays, spotted microarrays, or other microarray products from Biorad, Agilent, or Eppendorf. Microarrays provide may contain a large number of genes or alternative splice variants that may be assayed in a single experiment. In some cases, the microarray device may contain the entire human genome or transcriptome or a substantial fraction thereof allowing a comprehensive evaluation of gene expression patterns, genomic sequence, or alternative splicing. Markers may be found using standard molecular biology and microarray analysis techniques as described in Sambrook Molecular Cloning a Laboratory Manual 2001 and Baldi, P., and Hatfield, W. G., DNA Microarrays and Gene Expression 2002.

Microarray analysis generally begins with extracting and purifying nucleic acids from a biological sample, (e.g. a biopsy or fine needle aspirate). For expression and alternative splicing analysis it may be advantageous to extract and/or purify RNA from DNA. It may further be advantageous to extract and/or purify mRNA from other forms of RNA such as tRNA and rRNA. In some cases, RNA samples with RIN≤5.0 may not be used for multi-gene microarray analysis, and may instead be used for single-gene RT-PCR and/or TaqMan™ assays. TaqMan™ probe-based assays are widely used in real-time PCR including gene expression assays, DNA quantification and SNP genotyping.

Various kits can be used for the amplification of nucleic acid and probe generation of the subject methods. Examples of kit that can be used in the present invention include but are not limited to Nugen WT-Ovation FFPE kit, cDNA amplification kit with Nugen Exon Module and Frag/Label module. The NuGEN WT-Ovation™ FFPE System V2 is a whole transcriptome amplification system that enables conducting global gene expression analysis on the vast archives of small and degraded RNA derived from FFPE samples. The system is comprised of reagents and a protocol for amplification of as little as 50 ng of total FFPE RNA. The protocol can be used for qPCR, sample archiving, fragmentation, and labeling. The amplified cDNA can be fragmented and labeled in less than two hours for GeneChip® 3' expression array analysis using NuGEN's FL-Ovation™ cDNA Biotin Module V2. For analysis using Affymetrix GeneChip® Exon and Gene ST arrays, the amplified cDNA can be used with the WT-Ovation Exon Module, then fragmented and labeled using the FL-Ovation™ cDNA Biotin Module V2. For analysis on Agilent arrays, the amplified cDNA can be fragmented and labeled using NuGEN's FL-Ovation™ cDNA Fluorescent Module. More information on Nugen WT-Ovation FFPE kit can be obtained at www.nugeninc.com/nugen/index.cfm/products/amplification-systems/wt-ovation-ffpe/.

Ambion WT-expression kit can be used. Ambion WT-expression kit allows amplification of total RNA directly without a separate ribosomal RNA (rRNA) depletion step. With the Ambion® WT Expression Kit, samples as small as 50 ng of total RNA can be analyzed on Affymetrix® GeneChip® Human, Mouse, and Rat Exon and Gene 1.0 ST Arrays. In addition to the lower input RNA requirement and high concordance between the Affymetrix® method and TaqMan™ real-time PCR data, the Ambion® WT Expression Kit provides a significant increase in sensitivity. For example, a greater number of probe sets detected above background can be obtained at the exon level with the Ambion® WT Expression Kit as a result of an increased signal-to-noise ratio. Ambion WT-expression kit may be used in combination with additional Affymetrix labeling kit.

AmpTec Trinucleotide Nano mRNA Amplification kit (6299-A15) can be used in the subject methods. The ExpressArt® TRinucleotide mRNA amplification Nano kit is suitable for a wide range, from 1 ng to 700 ng of input total RNA. According to the amount of input total RNA and the required yields of aRNA, it can be used for 1-round (input >300 ng total RNA) or 2-rounds (minimal input amount 1 ng total RNA), with aRNA yields in the range of >10 µg. AmpTec's proprietary TRinucleotide priming technology results in preferential amplification of mRNAs (independent of the universal eukaryotic 3'-poly(A)-sequence), combined with selection against rRNAs. More information on AmpTec Trinucleotide Nano mRNA Amplification kit can be obtained at www.amp-tec.com/products.htm. This kit can be used in combination with cDNA conversion kit and Affymetrix labeling kit.

Gene expression levels can be obtained or measured in an individual without first obtaining a sample. For example, gene expression levels may be determined in vivo, that is in the individual. Methods for determining gene expression levels in vivo can include imaging techniques such as CAT, MRI; NMR; PET; and optical, fluorescence, or biophotonic imaging of protein or RNA levels using antibodies or molecular beacons. Such methods are described in US 2008/0044824, US 2008/0131892, herein incorporated by reference. Additional methods for in vivo molecular profiling are contemplated to be within the scope of the present invention.

Protein Content Adequacy Test

Protein content in a biological sample can be measured using a variety of methods, including, but not limited to: ultraviolet absorbance at 280 nanometers, cell staining, or protein staining (e.g., with Coomassie blue or bichichonic acid). Protein can be extracted from the biological sample prior to measurement of the sample. Multiple tests for adequacy of the sample can be performed in parallel, or one at a time. The biological sample can be divided into aliquots for the purpose of performing multiple diagnostic tests prior to, during, or after assessing adequacy. Any adequacy test can be performed on a portion or aliquot of the biological sample (or materials derived therefrom). The portion or aliquot of the biological sample (or materials derived therefrom) used for an adequacy test may or may not be suitable for further diagnostic testing. The entire sample can be assessed for adequacy. In any case, the test for adequacy can be billed to the subject, medical provider, insurance provider, or government entity.

A biological sample can be tested for adequacy soon or immediately after collection. In some cases, when the sample adequacy test does not indicate a sufficient amount sample or sample of sufficient quality, additional samples can be taken.

Test for Iodine Levels

Iodine can be measured by a chemical method such as described in U.S. Pat. No. 3,645,691 which is incorporated herein by reference in its entirety or other chemical methods such as for measuring iodine content. Chemical methods for iodine measurement include but are not limited to methods based on the Sandell and Kolthoff reaction. Said reaction proceeds according to the following equation:

2Ce4++As3+→2Ce3++As5+I.

Iodine can have a catalytic effect upon the course of the reaction, e.g., the more iodine present in the preparation to be analyzed, the more rapidly the reaction proceeds. The speed of reaction is proportional to the iodine concentration. In some cases, this analytical method can carried out in the following manner: A predetermined amount of a solution of arsenous oxide As2O3 in concentrated sulfuric or nitric acid is added to the biological sample and the temperature of the mixture is adjusted to reaction temperature, i.e., usually to a temperature between 20° C. and 60° C. A predetermined amount of a cerium (IV) sulfate solution in sulfuric or nitric acid is added thereto. Thereupon, the mixture is allowed to react at the predetermined temperature for a definite period of time. Said reaction time is selected in accordance with the order of magnitude of the amount of iodine to be determined and with the respective selected reaction temperature. The reaction time is usually between about 1 minute and about 40 minutes. Thereafter, the content of the test solution of cerium (IV) ions is determined photometrically. The lower the photometrically determined cerium (IV) ion concentration is, the higher is the speed of reaction and, consequently, the amount of catalytic agent, i.e., of iodine. In this manner the iodine of the sample can directly and quantitatively be determined.

Iodine content of a sample of thyroid tissue can also be measured by detecting a specific isotope of iodine such as for example 123I, 124I, 125I, and 131I. In still other cases, the marker can be another radioisotope such as an isotope of carbon, nitrogen, sulfur, oxygen, iron, phosphorous, or hydrogen. The radioisotope in some instances can be administered prior to sample collection. Methods of radioisotope administration suitable for adequacy testing can include injection into a vein or artery, or by ingestion. A suitable period of time between administration of the isotope and acquisition of thyroid nodule sample so as to effect absorption of a portion of the isotope into the thyroid tissue can include any period of time between about a minute and a few days or about one week including about 1 minute, 2 minutes, 5 minutes, 10 minutes, 15 minutes, ½ an hour, an hour, 8 hours, 12 hours, 24 hours, 48 hours, 72 hours, or about one, one and a half, or two weeks, and can readily be determined by one skilled in the art. Alternatively, samples can be measured for natural levels of isotopes such as radioisotopes of iodine, calcium, magnesium, carbon, nitrogen, sulfur, oxygen, iron, phosphorous, or hydrogen.

Variant Selections and Allele Frequencies

To estimate kinship coefficient using detected variants (used interchangeably with "genetic aberrations" throughout) through next generation sequencing (NGS), the first step is to identify a variant set. High quality variants can be identified by the 1000 genome project and ones with sufficient coverage in a sequencing assay. Sufficient coverage can be defined as having read depth of more than 30 in majority of samples, replicates included. Once the variant set is identified, the genotype of each sample on this targeted set may be compiled. This forms the basis for calculating kinship coefficients among any pairs. In many cases, this calculation is based on unrelated samples. When biological and/or technical replicates exist for a given patient, one sample may be randomly selected to be included in the calculation of allele frequencies. See FIG. 1.

One or more genetic aberrations, such as single nucleotide polymorphisms (SNPs), can be selected based on an average coverage for the genetic locus in a sequencing assay in order to determine kinship coefficients. Sequencing coverage can be the average number of reads that align to a known reference sequence, such as human reference sequence. A NGS coverage level can be helpful in determining whether variant calling can be made with a certain degree of confidence at a particular base position. For example, higher levels of coverage where each base is covered by a greater number of aligned sequence reads, the base calls can be made with a higher degree of confidence. In some cases, SNPs with coverage of at least 20×, 30×, 40×, 50×, 60×, 70×, 80×, 90×, 100×, 120×, 140×, 160×, 180×, 200×, 220×, 240×, 260×, 280×, 300×, or more may be selected. SNPs with coverage of at least 20× may be selected. SNPs with an average coverage of about 200× or less may be selected. SNPs with a coverage of about 20× to about 700× may be selected. SNPs with an average coverage of about 40× to about 600× may be selected. SNPs with an average coverage of about 60× to about 500× may be selected. SNPs with an average coverage of about 80× to about 400× may be selected. SNPs with an average coverage of about 100× to about 300× may be selected. SNPs with an average coverage of about 150× to about 200× may be selected.

One or more genetic aberrations, such as SNPs, can be selected based on zygosity, for example, heterozygosity of a given genetic locus in order to determine kinship coefficients. Zygosity can be determined based on whether the two alleles in a diploid organism have identical or different DNA sequences. For example, when the two alleles have identical sequences, it may be homozygous. On the contrary, when the two alleles have different sequences, the locus may be heterozygous. Zygosity of the locus may be useful in selecting SNPs. For example, higher level of heterozygosity may be useful in determining kinship coefficient at a certain degree of confidence. In some cases, a genetic locus with heterozygosity of at least 1%, 2%, 3%, 4%, 5%, 6%, 7%, 8%, 9%, 10%, 11%, 12%, 13%, 14%, 15%, 16%, 17%, 18%, 19%, 20% or more may be selected. A genetic locus with heterozygosity of at least 10% may be selected.

Variant Calling Pipeline

A customized analysis pipeline can be used to process the raw sequencing data from a sequencing assay, such as using NextSeg™ 500 and generate variant calls that can be used for kinship analysis described herein. The first step may include de-multiplexing the raw sequencing reads, and assigning reads to each sample. This can be achieved through publicly available programs, such as Illumina public software, BCL2FASTQ. Before and after the de-multiplexing, customized scripts may be developed to prepare the parameters for de-multiplexing programs, such as BCL2FASTQ, re-organize the FASTQ files and check any contamination and the FASTQ quality before the pipeline can be invoked.

After de-multiplexing, the pipeline may be configured for variant calling on RNA-seq by following the GATK Best Practices. It comprises two sections: pre-process and variant call. The first section can include STAR-based 2-pass alignment against a reference genome, such as the human genome build 37, mark duplicates and sort, detection of fusion by STAR Fusion, expression profiling via HTSeq-count, RNASeQC, and SAMTools QC. The second section, which can be processed via GATK, may include multiple parts. For example, the second section may include of six parts: splitting reads across exons and trimming N's off, indel re-alignment, recalibration to adjust quality scores, variant call, variant filtration, and coverage at known sites.

Determination of Kinship

To identify a biological sample in a plurality of samples as belonging to a subject, a kinship analysis may be performed. A kinship analysis can result in accurately identifying the biological sample as belonging to the subject. For example, a biological sample can be identified as belong to the subject at an accuracy of at least about 70%. A biological sample can be identified as belong to the subject at an accuracy of at least about 75%. A biological sample can be identified as belong to the subject at an accuracy of at least about 80%. A biological sample can be identified as belong to the subject at an accuracy of at least about 85%. A biological sample can be identified as belong to the subject at an accuracy of at least about 90%. A biological sample can be identified as belong to the subject at an accuracy of at least about 95%. A biological sample can be identified as belong to the subject at an accuracy of at least about 99%.

A kinship analysis can comprise determining kinship coefficients based on genetic aberrations in a biological sample. Kinship coefficients can be determined to track technological and/or biological replicates, monitor sample integrity or measure sample quality. Kinship can be determined by estimating identity by descent sharing probabilities, k-coefficients, and/or kinship coefficient.

The three k-coefficients, $k_{0ij}$, $k_{1ij}$ and $k_{2ij}$, may be defined as the probability that a pair of non-inbred individual i and j share 0, 1, and 2 alleles identity by descent respectively at a genetic locus. The kinship coefficient between individual i and j, may be defined to be the probability that an allele selected randomly from individual i and an allele selected randomly from the same autosomal locus of individual j are identity by descent. The relationship between k-coefficients and kinship coefficient is $\phi_{ij}=0.5k_{2ij}+0.25\,k_{1ij}$ and $0 \leq \phi_{ij} \leq 0.5$.

An expectation maximization (EM) algorithm using unlined loci can be used to find maximum-likelihood estimators (MLE) for k-coefficients. The log-likelihood function for k-coefficients is $$l(k_{ij}) = \sum_{s \in S_{ij}} \log\{Pr(G_i^s, G_j^s | k_{0ij}, k_{1ij}, k_{2ij})\}$$

where $G_i^s$ and $G_j^s$ are genotypes at loci s=1, 2, . . . S for individual i and j respectively. The conditional probability of genotypes, $Pr(G_i^s, G_j^s | k_{0ij}, k_{1ij}, k_{2ij})$, is computed under the assumption of Hardy-Weinberg Equilibrium. After finding MLE of k-coefficients, $\hat{k}_{0ij}$, $\hat{k}_{1ij}$ and $\hat{k}_{2ij}$, the kinship coefficient can be estimated by $\hat{\phi}_{ij}^{MLE} = 0.5 \hat{k}_{2ij} + 0.25 \hat{k}_{1ij}$.

Comparison of Kinship Coefficients

The MLEs of kinship coefficients may be compared to other methods including the method of moment (MOM) and shared genotypes ratio (SGR) over total genotypes may be observed. The MOM may be used to estimate kinship coefficients directly from genotype data and used widely in genetic studies. The MOM estimator of kinship coefficient may be defined as $$\hat{\phi}_{ij}^{MOM} = \frac{1}{2} \frac{1}{|S_{ij}|} \sum_{s \in S_{ij}} \frac{(g_i^s - \hat{p}_s)(g_j^s - \hat{p}_s)}{\frac{1}{2}\hat{p}_s(1-\hat{p}_s)}$$

where $g_i^s = 0$, 0.5, or 1 for genotype AA, Aa and aa respectively at loci $s \in S_{ij}=1, 2, \ldots$ S and a is the alternative allele. $\hat{p}_s$ is defined as the mean of observed frequency of alternative allele a at a locus s. Since the MOM does not restrict the parameter space for $\phi_{ij}^{MOM}$, it sometimes results in estimated values outside of the defined range [0, 0.5] of the kinship coefficient. The estimated kinship coefficients are truncated to [0, 0.5].

Distinguishing Replicates from Non-Replicates

The pairs of technological or biological replicates from non-replicates can be distinguished by computing the proportion of shared heterozygous (Aa) and homozygous genotypes (aa) of alternative allele between two samples over total unique genotypes (either Aa or aa) observed in two samples as $$\hat{\phi}_{ij}^{SGR} = \frac{1}{2} \frac{1}{|T_{ij}|} \sum_{s \in T_{ij}} |G_i^s = G_j^s|$$

where $T_{ij}$ is a set of locus where at least one individual has either heterozygote or homozygous genotype of alternate allele and $|T_{ij}|$ indicates the number of element of $T_{ij}$. Note that $T_{ij}$ can be different for each pair of individual i and j.

When a range of values is indicated herein, and the range begins with a modifier such as "greater than", "at least", "more than", "about", etc., the modifier is meant to be included for every value in the range, unless where otherwise indicated. For example, "at least 1, 2, or 3" means "at least 1, at least 2, or at least 3," as used herein. Ranges can be expressed herein as from "about" one particular value, and/or to "about" another particular value. When such a range is expressed, another embodiment includes from the one particular value and/or to the other particular value. Similarly, when values are expressed as approximations, by use of the antecedent "about," it will be understood that the particular value forms another embodiment. It will be further understood that the endpoints of each of the ranges are significant both in relation to the other endpoint, and independently of the other endpoint. "About" means a referenced numeric indication plus or minus 10% of that referenced numeric indication. For example, the term about 4 may include a range of 3.6 to 4.4.

Data Analysis

Processing of expression profile may be improved through the application of algorithms designed to normalize and/or improve the reliability of the data. In some embodiments of the present invention the data analysis requires a computer or other device, machine or apparatus for application of the various algorithms described herein due to the large number of individual data points that are processed. A "machine learning algorithm" refers to a computational-based prediction methodology, also referred to as a "classifier", employed for characterizing a gene expression profile. The signals corresponding to certain expression levels, which are obtained by, e.g., microarray-based hybridization assays, are typically subjected to the algorithm in order to classify the expression profile. Supervised learning generally involves "training" a classifier to recognize the distinctions among classes and then "testing" the accuracy of the classifier on an independent test set. For new, unknown samples the classifier can be used to predict the class in which the samples belong.

Methods of data analysis of gene expression levels and/or of kinship analysis may further include the use of a pre-classifier algorithm. For example, fine needle aspirates (FNAs) of thyroid nodules contain several cell types, including thyroid follicular cells, thyroid medullary cells, blood cells (RBCs, WBCs, platelets), smooth muscle cells and infiltrating macrophages and lymphocytes. Diagnostic classification of FNAs involves primarily follicular cells (for cancers derived from the follicular cell such as papillary carcinoma, follicular carcinoma, and anaplastic thyroid carcinoma) and medullary cells (for medullary cancer). Since medullary and anaplastic thyroid cancers are rarely present in the indeterminate class, the diagnosis of indeterminate FNAs mainly concerns the distinction of follicular adenoma versus follicular carcinoma. The gene expression signal of the follicular cell is thus diluted out and possibly confounded by other cell types present in the FNA. An upfront method of determining the cellular make-up of a particular FNA may allow the resulting gene expression signatures to be calibrated against the dilution effect. A combination of known cell-specific genes may be used as an upfront mini-classifier for each cell component of the FNA. An algorithm may then use this cell-specific molecular fingerprint, pre-classify the samples according to their composition and then apply a correction/normalization factor. This data/information may then be fed in to a final classification algorithm which may incorporate that information to aid in the final conclusion of replicates vs non-replicates. In some embodiments of the present invention, results are classified using a trained algorithm. Trained algorithms of the present invention include algorithms that have been developed using a reference set of known technical/biological replicates and non-replicates.

Computer Systems

Figure 6:
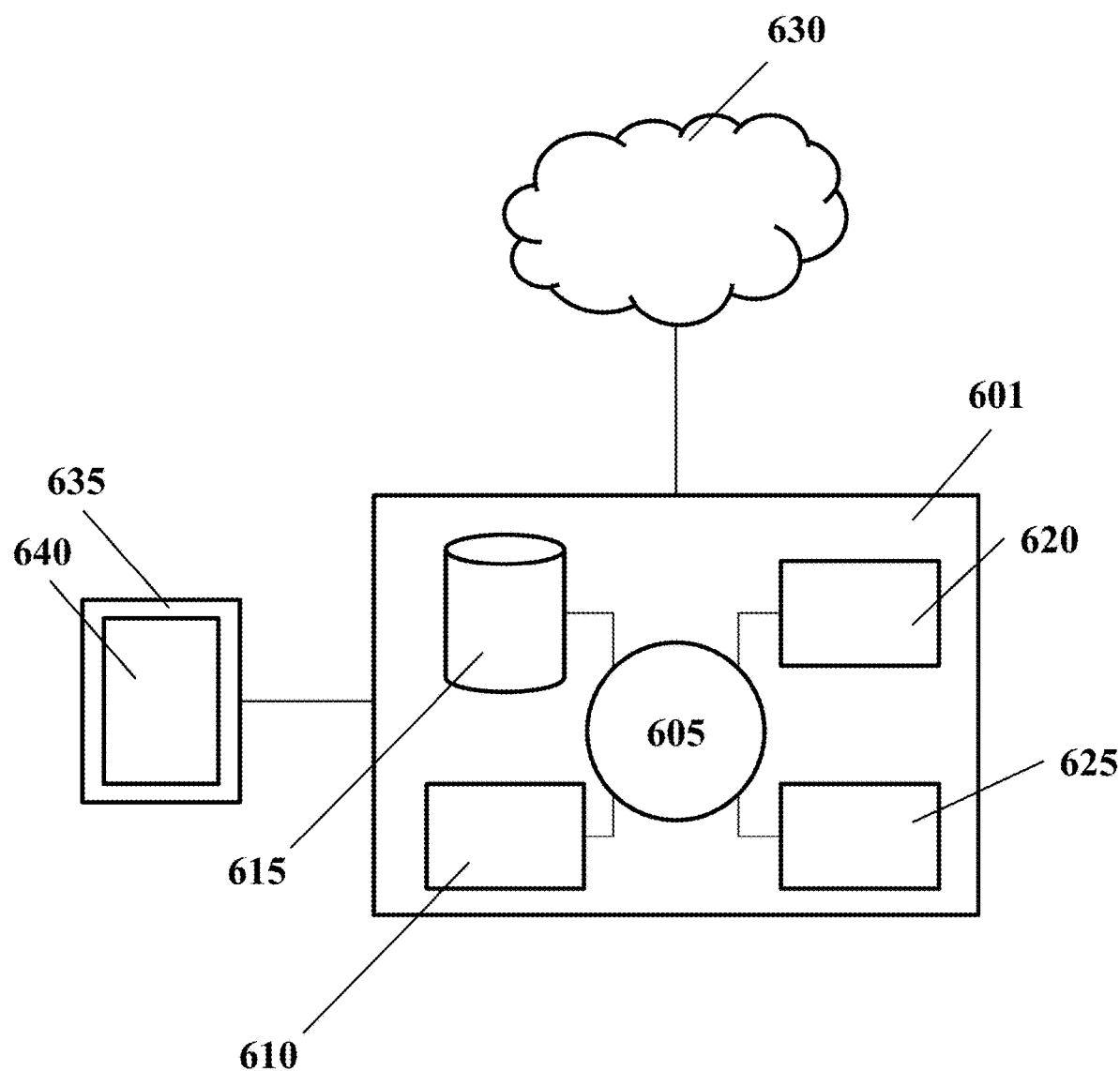
FIG. 6 shows a computer system that is programmed or otherwise configured to implement methods provided herein.

The present disclosure provides computer systems that are programmed or otherwise configured to implement methods of the disclosure. FIG. 6 shows a computer system 601 that is programmed or otherwise configured to process raw sequencing data from a sequencing assay and generate variant calls, to assess variants for coverage and heterzygosity, to employ kinship metrics on the sequencing data and to report kinship between a sample pair. The computer system 601 can regulate various aspects of kinship analysis of the present disclosure, such as, for example, employing kinship metrics and reporting kinship between samples based on a set threshold. The computer system 601 can be an electronic device of a user or a computer system that is remotely located with respect to the electronic device. The electronic device can be a mobile electronic device.

The computer system 601 includes a central processing unit (CPU, also "processor" and "computer processor" herein) 605, which can be a single core or multi core processor, or a plurality of processors for parallel processing. The computer system 601 also includes memory or memory location 610 (e.g., random-access memory, read-only memory, flash memory), electronic storage unit 615 (e.g., hard disk), communication interface 620 (e.g., network adapter) for communicating with one or more other systems, and peripheral devices 625, such as cache, other memory, data storage and/or electronic display adapters. The memory 610, storage unit 615, interface 620 and peripheral devices 625 are in communication with the CPU 605 through a communication bus (solid lines), such as a motherboard. The storage unit 615 can be a data storage unit (or data repository) for storing data. The computer system 601 can be operatively coupled to a computer network ("network") 630 with the aid of the communication interface 620. The network 630 can be the Internet, an internet and/or extranet, or an intranet and/or extranet that is in communication with the Internet. The network 630 in some cases is a telecommunication and/or data network. The network 630 can include one or more computer servers, which can enable distributed computing, such as cloud computing. The network 630, in some cases with the aid of the computer system 601, can implement a peer-to-peer network, which may enable devices coupled to the computer system 601 to behave as a client or a server.

The CPU 605 can execute a sequence of machine-readable instructions, which can be embodied in a program or software. The instructions may be stored in a memory location, such as the memory 610. The instructions can be directed to the CPU 605, which can subsequently program or otherwise configure the CPU 605 to implement methods of the present disclosure. Examples of operations performed by the CPU 605 can include fetch, decode, execute, and writeback.

The CPU 605 can be part of a circuit, such as an integrated circuit. One or more other components of the system 601 can be included in the circuit. In some cases, the circuit is an application specific integrated circuit (ASIC).

The storage unit 615 can store files, such as drivers, libraries and saved programs. The storage unit 615 can store user data, e.g., user preferences and user programs. The computer system 601 in some cases can include one or more additional data storage units that are external to the computer system 601, such as located on a remote server that is in communication with the computer system 601 through an intranet or the Internet.

The computer system 601 can communicate with one or more remote computer systems through the network 630. For instance, the computer system 601 can communicate with a remote computer system of a user (e.g., clinician). Examples of remote computer systems include personal computers (e.g., portable PC), slate or tablet PC's (e.g., Apple® iPad, Samsung® Galaxy Tab), telephones, Smart phones (e.g., Apple® iPhone, Android-enabled device, Blackberry®), or personal digital assistants. The user can access the computer system 601 via the network 630.

Methods as described herein can be implemented by way of machine (e.g., computer processor) executable code stored on an electronic storage location of the computer system 601, such as, for example, on the memory 610 or electronic storage unit 615. The machine executable or machine readable code can be provided in the form of software. During use, the code can be executed by the processor 605. In some cases, the code can be retrieved from the storage unit 615 and stored on the memory 610 for ready access by the processor 605. In some situations, the electronic storage unit 615 can be precluded, and machine-executable instructions are stored on memory 610.

The code can be pre-compiled and configured for use with a machine having a processer adapted to execute the code, or can be compiled during runtime. The code can be supplied in a programming language that can be selected to enable the code to execute in a pre-compiled or as-compiled fashion.

Aspects of the systems and methods provided herein, such as the computer system 601, can be embodied in programming. Various aspects of the technology may be thought of as "products" or "articles of manufacture" typically in the form of machine (or processor) executable code and/or associated data that is carried on or embodied in a type of machine readable medium. Machine-executable code can be stored on an electronic storage unit, such as memory (e.g., read-only memory, random-access memory, flash memory) or a hard disk. "Storage" type media can include any or all of the tangible memory of the computers, processors or the like, or associated modules thereof, such as various semiconductor memories, tape drives, disk drives and the like, which may provide non-transitory storage at any time for the software programming. All or portions of the software may at times be communicated through the Internet or various other telecommunication networks. Such communications, for example, may enable loading of the software from one computer or processor into another, for example, from a management server or host computer into the computer platform of an application server. Thus, another type of media that may bear the software elements includes optical, electrical and electromagnetic waves, such as used across physical interfaces between local devices, through wired and optical landline networks and over various air-links. The physical elements that carry such waves, such as wired or wireless links, optical links or the like, also may be considered as media bearing the software. As used herein, unless restricted to non-transitory, tangible "storage" media, terms such as computer or machine "readable medium" refer to any medium that participates in providing instructions to a processor for execution.

Hence, a machine readable medium, such as computer-executable code, may take many forms, including but not limited to, a tangible storage medium, a carrier wave medium or physical transmission medium. Non-volatile storage media include, for example, optical or magnetic disks, such as any of the storage devices in any computer(s) or the like, such as may be used to implement the databases, etc. shown in the drawings. Volatile storage media include dynamic memory, such as main memory of such a computer platform. Tangible transmission media include coaxial cables; copper wire and fiber optics, including the wires that comprise a bus within a computer system. Carrier-wave transmission media may take the form of electric or electromagnetic signals, or acoustic or µght waves such as those generated during radio frequency (RF) and infrared (IR) data communications. Common forms of computer-readable media therefore include for example: a floppy disk, a flexible disk, hard disk, magnetic tape, any other magnetic medium, a CD-ROM, DVD or DVD-ROM, any other optical medium, punch cards paper tape, any other physical storage medium with patterns of holes, a RAM, a ROM, a PROM and EPROM, a FLASH-EPROM, any other memory chip or cartridge, a carrier wave transporting data or instructions, cables or links transporting such a carrier wave, or any other medium from which a computer may read programming code and/or data. Many of these forms of computer readable media may be involved in carrying one or more sequences of one or more instructions to a processor for execution.

The computer system 601 can include or be in communication with an electronic display 635 that comprises a user interface (UI) 640 for providing, for example, results of the kinship analysis, such as if a pair of samples is related or non-related. Examples of UI's include, without limitation, a graphical user interface (GUI) and web-based user interface.

Methods and systems of the present disclosure can be implemented by way of one or more algorithms. An algorithm can be implemented by way of software upon execution by the central processing unit 605. The algorithm can, for example, process the raw sequencing data from a sequencing assay and generate variant calls.

EXAMPLES

Materials

RNA-seq: 15 ng of total RNA was input into the Illumina RNA Access kit (Illumina, San Diego Calif.) and performed according to the manufacturer's instructions on a Hamilton STAR robot. Pools of 16 samples were sequenced on the NextSeq™ 500 with a NextSeq™ v2 chemistry 150 cycle kit (Illumina, San Diego, Calif.) using paired-end 76 cycle sequencing chemistry.

Targeted DNA-seq: 96 SNPs informative SNPs were chosen based on RNA-seq data for common dbSNPs that had heterozygotes in >10% of the sequencing population, and average coverage >200×. 87 SNPs gave functional amplicons in the ion torrent assay. 10 ng of genomic DNA extracted from fine-needle aspirated biopsies of thyroid nodules was used as the input for the ThermoFisher Ion AmpliSeq™ DNA assay according to manufacturer's instructions. The library inputs were quantitated with the ThermoFisher Taqman™ Quantitation kit. The libraries were pooled together to a final concentration of 50 pM for loading onto the Ion540™ chip in the ThermoFisher Ion Chef™ and sequenced on the ThermoFisher Ion S5™ XL. The Torrent Server Suite generated base calls, reads, aligned reads, and vcf files relative to the hg19 build of the human genome.

Lung transbronchial biopsy (TBB) samples: RNA-seq data were generated from 699 lung transbronchial biopsy (TBB) samples of 112 patients (Pankratz, D. G. et al., 2017). Each patient has 3-5 different samples that are called as biological replicates. Eight lung samples were chosen for quality control and sequenced repeatedly across 8 different batches, which are referred to as technical replicates. Among 243,951 pairs, there are 1,893 pairs of biological replicates and 563 pairs of technical replicates.

Thyroid tissue samples: RNA-seq data were generated for 2,053 samples over 26 batches and with a total of 2,106,159 pairs of independent samples, 49 pairs of biological replicates and 170 pairs of technical replicates. Additionally, DNA-seq data were generated for 609 samples and matched with 2,047 RNA-seq samples after removing low quality samples. There were 589 matched pairs between DNA-seq and RNA-seq data and 1,246,034 pairs of different samples.

Example 1

Determining Quality of Variant/SNP Calls from RNA-Seq Data

Figure 2:
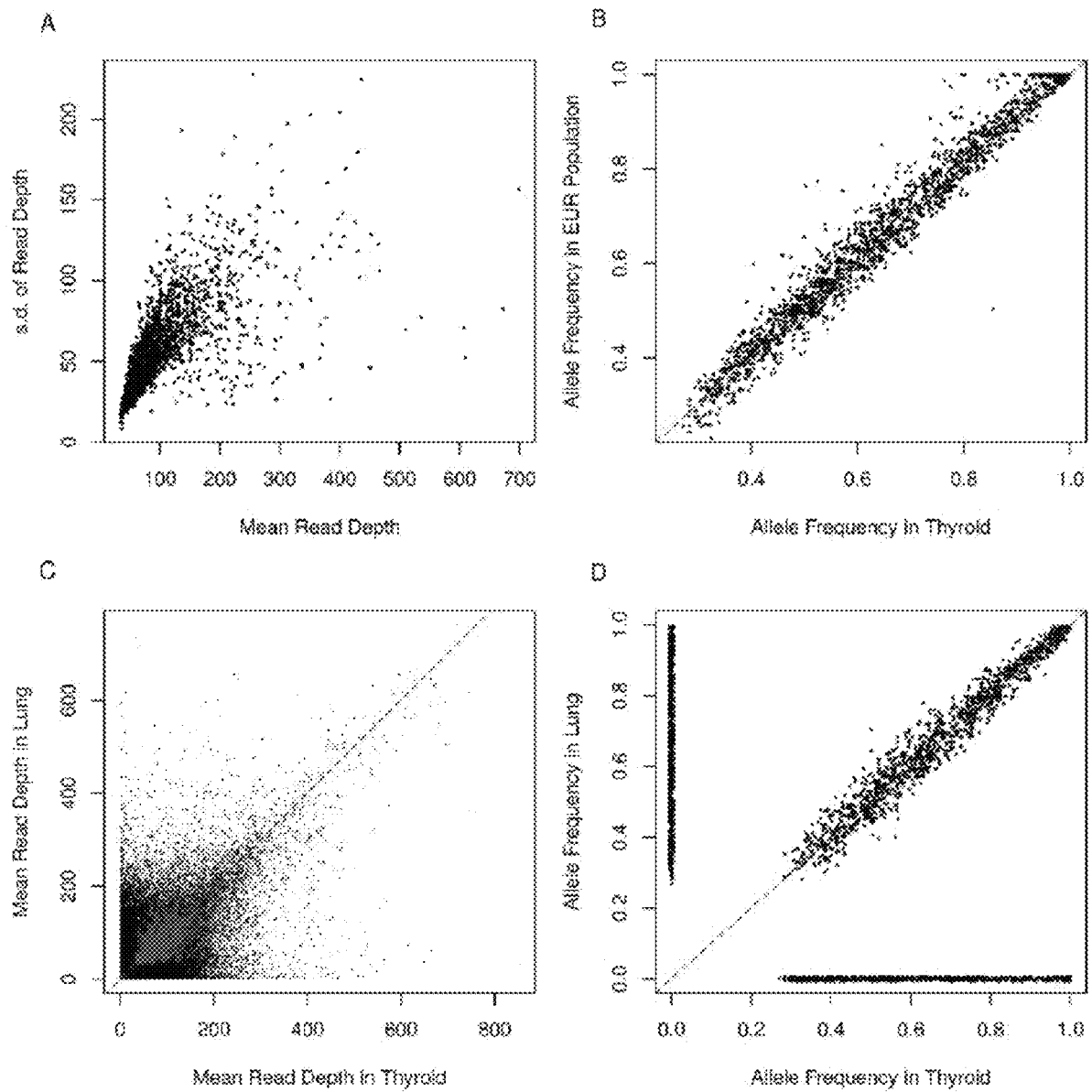
FIG. 2 shows (A) Mean vs standard deviation of read depth of 2,054 variants in thyroid samples after filtering (B) Observed allele frequencies for alternative allele in thyroid samples vs allele frequencies of the 2,021 matched variants in European population from Phase 3 1000 Genomes data (C) Mean read depth of 222,974 commonly detected variants on autosomal chromosomes in thyroid samples and lung TBB samples. Red points are the ones selected after filtering (D) Allele frequencies of 2,736 variants detected either in thyroid samples or lung samples after filtering. 1,332 variants are in common and 722 variants are detected in thyroid samples only and 682 variants are detected in lung samples only.

The coverage of RNA-seq data may be dependent on expression levels, and different sample types may have different expression signatures. FIG. 2 illustrates uneven coverage on RNA-seq and how both variant coverage and allele-frequency can be highly sample-set dependent. Panel A displays the mean versus standard deviation of read depth of 2,054 variants across 2,053 thyroid samples after variant filtering. The averaged read depth for most of variants is below 200× (90%) and covers a wide range from about 30× to more than about 700×. The correlation between the mean and standard deviation is moderate (cor=0.677) and the relationship may be highly variant dependent. Panel B displays observed alternative allele frequencies estimated using in-house thyroid sample set versus the European population from Phase 3 1000 Genomes Project. The overall correlation is high (cor=0.985), and a substantial proportion of variants shows moderate difference: 15% of variants have more than 5% difference in allele frequency and 2% of variants have more than 10% difference in allele frequency. Any deviations caused by discrepancy in allele frequency may be avoided by deriving estimates directly using the sample set of interest. Panel C and D show the read depth and the alternative allele frequency calculated using the thyroid sample set versus the lung sample set. Panel C and D suggest that different sample types may result in differences in these two metrics. The overall correlation on read depth is 0.669 (Panel C) and among the 2736 variants detected in either thyroid or lung samples after filtering, 1332 variants (48.7%) are in common while 722 (26.4%) are detected in thyroid samples and 682 (24.9%) are detected in lung samples. This may suggest that customized variant selection may be important to ensure sufficient coverage. Sample-type specific allele-frequency estimation may also be important when calculating kinship coefficients.

Example 2

Figure 3:
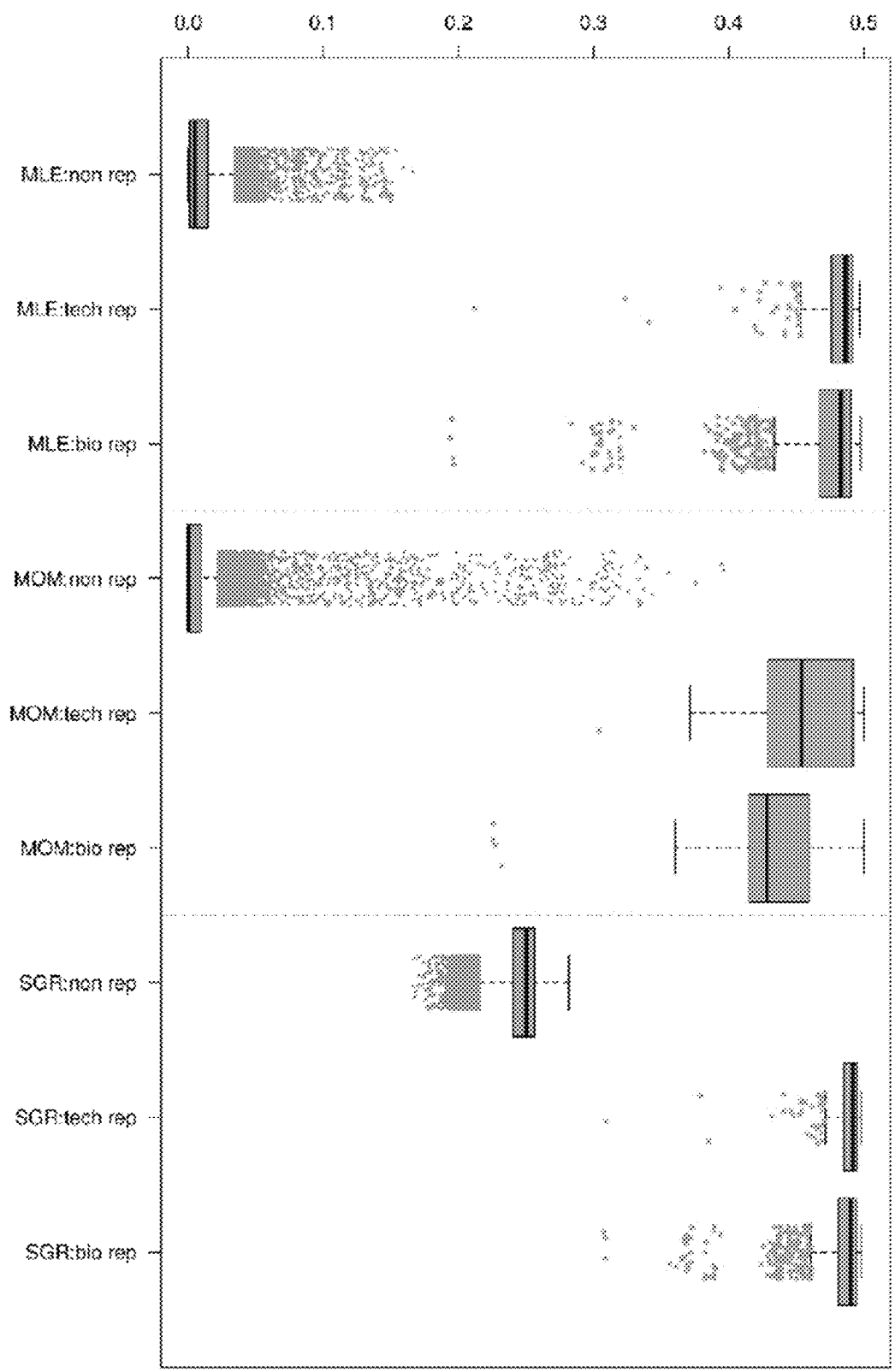
FIG. 3 shows boxplots of pairwise estimated kinship coefficients in lung samples using maximum likelihood estimation (MLE), method of moment (MOM) and shared genotype ratio (SGR). In total, 2,014 variants and 699 samples are used to estimate kinship coefficients for 241,495 unrelated pairs, 563 technical replicates and 1,893 biological replicates.

Kinship Coefficient for Distinguishing Biological/Technical Replicates from Non-Replicates After filtering (as described in FIG. 1), the kinship is estimated using 2,014 detected variants on autosomal chromosomes for all pairs of 699 lung samples. Estimated kinship coefficients using three different methods (MLE, MOM, SGR) are compared and the result is shown in FIG. 3. The MOM kinship coefficients of several technical/biological replicates overlap with those of independent pairs since estimated values of independent pairs are ranged from 0 to 0.496. Both MLE and SGR also can separate biological/technical replicates from independent pairs. The maximum of MLE kinship coefficients for independent pairs is 0.166 and the minimum values for biological and technical replicates are 0.194 and 0.212 respectively. The maximum of SGR for independent pairs is 0.282 and the minimum values for biological and technical replicates are 0.308 and 0.309 respectively.

Example 3

Kinship Coefficient for Detecting Experimental Errors

Figure 4A:
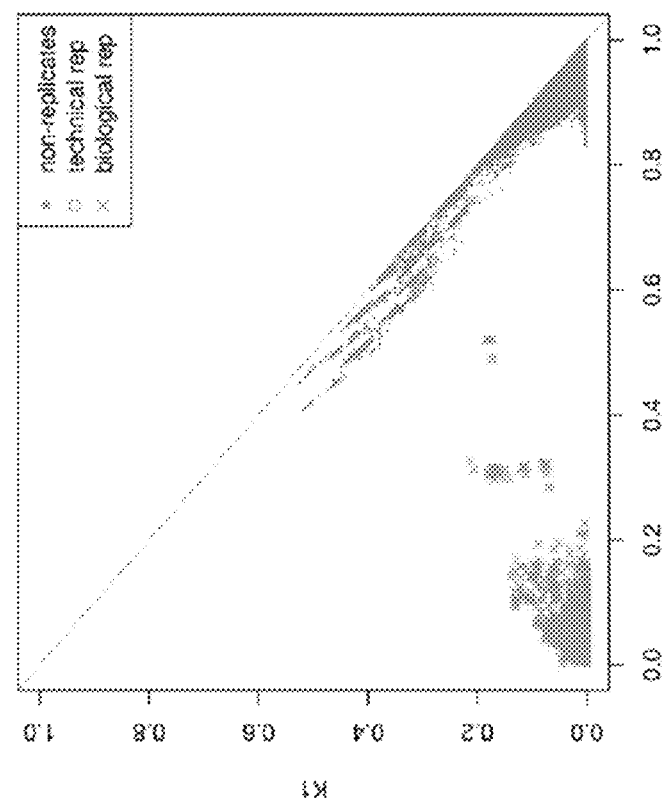
FIG. 4 shows an estimated k0 vs. k1 for Thyroid (Panel A) and Lung (Panel B) samples.
Figure 4B:
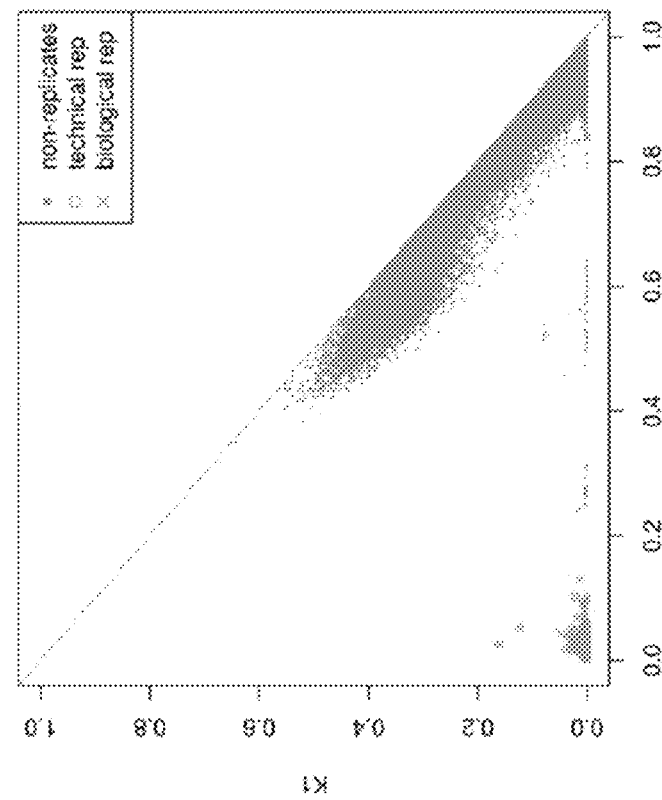

In addition to kinship coefficients, the MLE method may allow to estimate k-coefficients and to categorize pairs into more specific relationship. Unexpected patterns may help to detect issues in experimental procedures and/or pipeline steps. For example, while the expected kinship coefficient is 0.25 for both full siblings and parent-offspring, the underlying value of $(k_{0ij}, k_{1ij}, k_{2ij})$ is different; k-coefficients are (0.25, 0.5, 0.25) for full siblings and (0, 1, 0) for parent-offspring. In our application, the expected value for k-coefficient is $(k_{0ij}, k_{1ij}, k_{2ij})=(1, 0, 0)$ for independent pairs and $(k_{0ij}, k_{1ij}, k_{2ij})=(0, 0, 1)$ for biological or technical replicates. The estimated k-coefficients for lung and thyroid samples are shown in FIG. 4. In thyroid samples, several unusual independent pairs with $\hat{k}_{2ij} > \sim 0.35$ can be identified since the expected of $\hat{k}_{2ij}$ is 0 and since they are expected to be independent (FIG. 4A). Further investigation revealed that for each pair, at least one sample is missing several chromosomes due to mapping pipeline failure. In lung TBB samples, there are several pairs of technical/biological replicates clustered around $0.25<\hat{k}_{0ij}<0.55$ while the expected value of $k_{0ij}$ is 0 (FIG. 4B). The samples of those pairs are low-quality sequence data due to low total read or high duplicate rate and they are also matched the ones in the lower tail in FIG. 3 for technical/biological replicates.

Example 4

Figure 5:
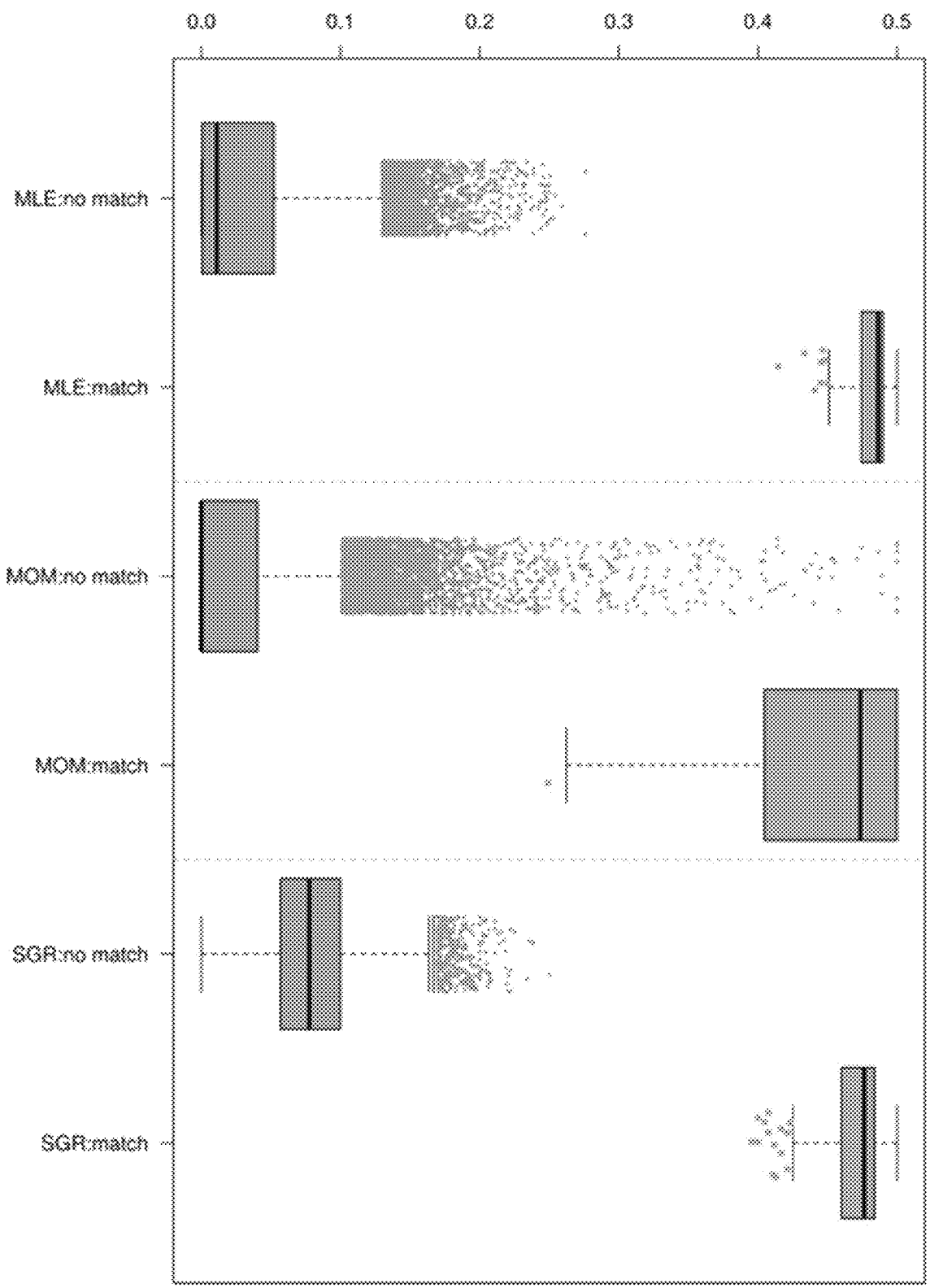
FIG. 5 shows boxplots of pairwise estimated kinship coefficients using 87 SNPs between 609 DNA-seq and 2,047 RNA-seq data of thyroid samples using maximum likelihood estimation (MLE), method of moment (MOM) and shared genotype ratio (SGR).

Kinship Coefficient for Distinguishing Biological Replicates from Non-Replicates FIG. 5 presents the estimated kinship coefficients by three models, MLE, MOM, and SGR for pairs of 2,047 RNA-seq and 609 DNA-seq data of thyroid samples from the same patient, i.e. biological replicates. The non-matched pairs indicate RNA-seq and DNA-seq data are from the different patients and matched pairs indicate both RNA-seq and DNA-seq data are from the same patient. For the matched pairs, all three models result in estimated kinship coefficients close to the expected value, 0.5, with mean (s.d.) of 0.482 (0.013), 0.448 (0.060) and 0.472 (0.021) for MLE, MOM and SGR, respectively. Similarly, for the non-matched pairs, the estimated kinship coefficients are closed to the expected value, 0 with mean (s.d) of 0.031 (0.041), 0.026 (0.044) and 0.080 (0.032) for MLE, MOM and SGR, respectively. The MLE may provide higher values for unrelated pairs and lower values for technical/biological replicates. The MOM kinship coefficients may be truncated to [0, 0.5] to remove outliers. The estimated kinship coefficients can distinguish technical/biological replicates from unrelated pairs, the results from both lung and thyroid data set may show over-estimated values in unrelated pairs and under-estimated values in replicated pairs. The result demonstrates that the estimated kinship coefficients successfully matched RNA-seq data with DNA-seq data of the same patient.

Example 5

Kinship Coefficient for Detecting Sample-to-Sample Contamination

In addition to using SNPs for confirming sample identity, common SNPs may be useful for other critical QC functions, detecting sample-to-sample contamination, in the clinical setting. SNP-based contamination metrics is helpful for eliminating samples that are above a critical threshold. The critical threshold is set on the metrics employed (e.g., MOM). Once the metrics is employed, kinship coefficients are used to detect sample mix-ups, such as by other samples.

While preferred embodiments of the present invention have been shown and described herein, it will be obvious to those skilled in the art that such embodiments are provided by way of example only. It is not intended that the invention be limited by the specific examples provided within the specification. While the invention has been described with reference to the aforementioned specification, the descriptions and illustrations of the embodiments herein are not meant to be construed in a limiting sense. Numerous variations, changes, and substitutions will now occur to those skilled in the art without departing from the invention. Furthermore, it shall be understood that all aspects of the invention are not limited to the specific depictions, configurations or relative proportions set forth herein which depend upon a variety of conditions and variables. It should be understood that various alternatives to the embodiments of the invention described herein may be employed in practicing the invention. It is therefore contemplated that the invention shall also cover any such alternatives, modifications, variations or equivalents. It is intended that the following claims define the scope of the invention and that methods and structures within the scope of these claims and their equivalents be covered thereby.

What is claimed is:

1. A method for biological sample processing, comprising:
   (a) obtaining a biological sample, wherein said biological sample comprises a plurality of transcripts corresponding to at least one gene having one or more genetic aberrations;

(b) subjecting said plurality of transcripts to nucleic acid amplification under conditions sufficient to amplify said plurality of transcripts, thereby generating amplification products;

(c) subjecting said amplification products of (b) to a sequencing assay to generate an expression profile of said plurality of transcripts corresponding to said at least one gene having said one or more genetic aberrations; and (d) using a computer classifier to process said expression profile generated in (c) to identify said biological sample as belonging to a subject, wherein said computer classifier performs a kinship analysis of said expression profile against one or more other expression profiles of one or more other biological samples of said subject or one or more other subjects.

2. The method of claim 1, further comprising, prior to (a), selecting said one or more genetic aberrations.

3. The method of claim 2, wherein said sequencing assay of (c) comprises sequencing said amplification products at a sequencing coverage of 20× or more for said one or more genetic aberrations.

4. The method of claim 2, wherein said sequencing assay of (c) comprises sequencing said amplification products at a sequencing coverage of from about 30× to about 700× for said one or more genetic aberrations.

5. The method of claim 2, wherein said one or more genetic aberrations have at least 10% heterozygosity.

6. The method of claim 1, wherein (d) comprises determining kinship coefficients based on at least a subset of said one or more genetic aberrations in said biological sample corresponding to genetic aberrations in one or more different biological samples.

7. The method of claim 6, wherein said kinship coefficients are determined using a method of moment, a shared genotypes ratio, a maximum-likelihood estimator, or any of identity by descent sharing probabilities.

8. The method of claim 1, wherein said sequencing assay of (c) comprises performing microarray, and serial analysis of gene expression (SAGE), and wherein said nucleic acid amplification comprises reverse transcription polymerase chain reaction (PCR), or quantitative PCR.

9. The method of claim 1, further comprising using a probe set with a plurality of probes that specifically binds to said plurality of transcripts or sequences derived from said plurality of transcripts to thereby enrich for said plurality of transcripts.

10. The method of claim 9, wherein said plurality of probes comprises ribonucleic acid, synthetic nucleotides or a combination thereof.

11. The method of claim 1, further comprising extracting ribonucleic acid molecules from said biological sample.

12. The method of claim 11, further comprising purifying messenger ribonucleic acid molecules from said biological sample.

13. The method of claim 1, wherein when said biological sample is identified as belonging to said subject, repeating (a)-(d) with an additional biological sample that is suspected of being from said subject.

14. The method of claim 1, further comprising, upon identifying said biological sample as belonging to said subject, classifying said biological sample as being malignant, benign or normal for a disease.

15. The method of claim 14, wherein said disease is thyroid cancer or lung cancer.

16. The method of claim 1, wherein said biological sample is selected from a plurality of samples suspected as being from said subject.

17. The method of claim 1, wherein said biological sample is among two or more biological samples being or suspected of being from said subject.

18. The method of claim 17, wherein identifying in (d) comprises identifying whether said biological sample is a biological replicate or a technical replicate.

19. The method of claim 1, wherein said one or more genetic aberrations comprise one or more single nucleotide polymorphisms.

* * * * *